(12) United States Patent
Waern

(10) Patent No.: US 11,254,937 B2
(45) Date of Patent: Feb. 22, 2022

(54) NUCLEIC ACID MOLECULES AND THEIR USE IN THERAPY

(71) Applicant: HEPGENE MEDICAL AB, Torslanda (SE)

(72) Inventor: Johan Waern, Torslanda (SE)

(73) Assignee: HEPGENE MEDICAL AB, Torslanda (SE)

( * ) Notice: Subject to any disclaimer, the term of this patent is extended or adjusted under 35 U.S.C. 154(b) by 0 days.

(21) Appl. No.: 16/608,227

(22) PCT Filed: Jun. 18, 2018

(86) PCT No.: PCT/SE2018/050641
§ 371 (c)(1),
(2) Date: Oct. 25, 2019

(87) PCT Pub. No.: WO2018/236273
PCT Pub. Date: Dec. 27, 2018

(65) Prior Publication Data
US 2020/0190512 A1  Jun. 18, 2020

(30) Foreign Application Priority Data

Jun. 19, 2017 (SE) .................................. 1750774-0

(51) Int. Cl.
*C12N 15/113* (2010.01)
*C12N 15/86* (2006.01)

(52) U.S. Cl.
CPC ............ *C12N 15/113* (2013.01); *C12N 15/86* (2013.01); *C12N 2310/14* (2013.01); *C12N 2310/315* (2013.01); *C12N 2320/30* (2013.01); *C12N 2800/107* (2013.01)

(58) Field of Classification Search
CPC .. C12N 15/113; C12N 15/86; C12N 2310/14; C12N 2310/315; C12N 2310/531; C12N 2320/30; C12N 2800/107; C10C 1/04; C07K 14/8125
USPC ....................... 514/44 A; 536/24.5
See application file for complete search history.

(56) References Cited

U.S. PATENT DOCUMENTS

| 2005/0137153 | A1 | 6/2005 | McSwiggen et al. | |
| 2009/0253583 | A1* | 10/2009 | Yoganathan | ......... C12Q 1/6886 506/9 |
| 2015/0011607 | A1* | 1/2015 | Brown | ............... A61P 1/16 514/44 A |
| 2016/0193242 | A1* | 7/2016 | Khvorova | ......... C12N 15/1135 514/44 A |
| 2016/0326524 | A1 | 11/2016 | Flotte et al. | |
| 2019/0010490 | A1* | 1/2019 | Cowan | ............. A61K 31/7088 |

FOREIGN PATENT DOCUMENTS

| EP | 0155188 A2 | 9/1985 | |
| KR | 20170115029 A | * 10/2017 | |
| WO | WO-2006034573 A1 | * 4/2006 | ........... C12Q 1/6886 |
| WO | 2012/145624 A2 | 10/2012 | |
| WO | 2015/195628 A2 | 12/2015 | |

OTHER PUBLICATIONS

NM_000295 (sequence published in 1975, 1976, 1992, 1993 & 2020) GenBank, sequence last updated_Jan. 17, 2021 (Year: 2021).*
Hasan et al. European Respiratory Journal 2011 38: p. 702. (Year: 2011).*
Zhang Y. (2013) Pre-miRNA. In: Dubitzky W., Wolkenhauer O., Cho KH., Yokota H. (eds) Encyclopedia of Systems Biology. Springer, New York, NY. https://doi.org/10.1007/978-1-4419-9863-7_323. (Year: 2013).*
International Search Report, dated Aug. 23, 2018, from corresponding PCT application No. PCT/SE2018/050641.
Written Opinion, dated Aug. 23, 2018, from corresponding PCT application No. PCT/SE2018/050641.
Li et al.; Combination therapy utilizing shRNA knockdown and an optimized resistant transgene for rescue of diseases caused by misfolded proteins; PNAS; Aug. 23, 2011; pp. 14258-14263; vol. 108, No. 34.
Barnett et al., "Wegener's Granulomatosis and $\alpha_1$-Antitrypsin-Deficiency Emphysema* Proteinase-Related Diseases," Chest 116, Jul. 1999, pp. 253-255.
Baum et al., "Retrovirus Vectors: Toward the Plentivirus?" Molecular Therapy, vol. 13, No. 6, Jun. 2006, pp. 1050-1063.
Bessis et al., "Immune responses to gene therapy vectors: influence on vector function and effector mechanisms," Gene Therapy (2004) 11, S10-S17.
Brummelkamp et al., "A System for Stable Expression of Short Interfering RNAs in Mammalian Cells," Science, vol. 296, Apr. 19, 2002, pp. 550-553.
Burrows et al., "Chemical chaperones mediate increased secretion of mutant $\alpha_1$-antitrypsin ($\alpha_1$-AT) Z: A potential pharmacological strategy for prevention of liver injury and emphysema in $\alpha_1$-AT deficiency," PNAS, vol. 97, No. 4, Feb. 15, 2000, pp. 1796-1801.
Carrell et al., "$\alpha_1$-Antitrypsin Deficiency: A Conformational Diseases," Chest 110, Dec. 1996 Supplement, pp. 243S-247S.
Cox et al., "Risk for Liver Disease in Adults with Alpha1-Antitrypsin Deficiency," The American Journal of Medicine, vol. 74, Feb. 1989, pp. 221-227.
Cox et al., "$\alpha_1$-Antitrypsin: A Guardian of Vascular Tissue," Mayo Clin Proc 1994; 69:1123-1124.
Cruz et al., "In vivo post-transcriptional gene silencing of $\alpha_1$-Antitrypsin by adeno-associated virus vectors expressing siRNA," Laboratory Investigation (2007) 87, 893-902.
Dull et al., "A Third-Generation Lentivirus Vector with a Conditional Packaging System," Journal of Virology, Nov. 1998, p. 8463-8471, vol. 72, No. 11.

(Continued)

*Primary Examiner* — Janet L Epps-Smith
(74) *Attorney, Agent, or Firm* — Nixon & Vanderhye

(57) ABSTRACT

Disclosed are products and methods for therapy using nucleic acid molecules, and in particular in relation to treatment of alpha-1-antitrypsin deficiency. Also disclosed are pharmaceutical compositions including the nucleic acids and/or delivery vehicles including the nucleic acids, and their use in manufacture of pharmaceutical compositions for use in therapy, such as treatment of alpha-1-antitrypsin deficiency.

13 Claims, 11 Drawing Sheets

Specification includes a Sequence Listing.

(56) References Cited

OTHER PUBLICATIONS

Elzouki et al., "Increased PiZ gene frequency for α1-Antitrypsin in patients with genetic haemochromatosis," Gut 1995; 36:922-926.
Fearnley et al., "α1-Antitrypsin phenotypes in acute anterior uveitis," British Journal of Ophthalmology, 1988, 72, 636-639.
Hidvegi et al., "Accumulation of Mutant α1-Antitrypsin Z in the Endoplasmic Reticulum Activates Caspases-4 and -12, NfkB, and BAP31 but Not the Unfolded Protein Response," The Journal of Biological Chemistry, vol. 280, No. 47, pp. 39002-39015, Nov. 25, 2005.
Hidvegi et al., "An Autophagy-Enhancing Drug Promotes Degradation of Mutant α1-Antitrypsin Z and Reduces Hepatic Fibrosis," Science, vol. 329, Jul. 9, 2010, pp. 229-223.
Hubbard et al., "Strategies for Aerosol Therapy of α1-Antitrypsin Deficiency by the Aerosol Route," Lung (1990) Suppl:565-578.
Karnaukhova et al., "Recombinant human alpha-1 proteinase inhibitor: towards therapeutic use," Amino Acids (2006) 30:317-332.
Lawless et al., "Activation of Endoplasmic Reticulum-Specific Stress Responses Associated with the Conformational Disease Z α1-Antitrypsin Deficiency," J Immunol 2004; 172:5722-5726.
Livak et al.,"Analysis of Relative Gene Expression Data Using Real-Time Quantitative PCR and the 2-ΔΔCt Method," Methods 25, 402-408 (2001).
Mahadeva et al., "6-mer Peptide Selectively Anneals to a Pathogenic Serpin Conformation and Blocks Polymerization," The Journal of Biological Chemistry, vol. 277, No. 9, Mar. 1, 2002, pp. 6771-6774.
Mazodier et al., "Systemic necrotizing vasculitides in severe alpha1-Antitrypsin Deficiency," QJ Med 1996; 89:599-611.
McBean et al., "α1-Antitrypsin Deficiency Panniculitis," Continuing Medical Education, vol. 71, Mar. 2003, p. 205-209.
Parfrey et al., "Inhibiting Polymerization: New Therapeutic Strategies for Z α1-Antitrypsin-Related Emphysema," American Journal of Respiratory Cell and Molecular Biology, vol. 31, 2004, p. 133-139.
Petrache et al., "Safety and efficacy of alpha-1-Antitrypsin Deficiency augmentation therapy in the treatment of patients with alpha-1-Antitrypsin Deficiency," Biologies: Targets & Therapy, Apr. 30, 2009.
Ramamoorth et al., "Non Viral Vectors in Gene Therapy—An Overview," Journal of Clinical and Diagnostic Research, Jan. 2015, vol. 9(1).
Riedel et al., "An Extended ΔCT-Method Facilitating Normalisation with Multiple Reference Genes Suited for Quantitative RT-PCR Analyses of Human Hepatocyte-Like Cells," PLOS One, Mar. 2014, vol. 9, issue 3.
Sandhaus, "α1-Antitrypsin Deficiency: 6 New and emerging treatments for α1-Antitrypsin Deficiency," Thorax 2004I 69:904-909.
De Serres et al., "Role of alpha-1 Antitrypsin in human health and disease," Journal of Internal Medicine, 2014, 276; 311-335.
Spencer et al., "Antibody Response to Aerosolized Transgenic Human Alpha1-Antitrypsin," The New England Journal of Medicine, 352;19, May 12, 2005, pp. 2030-2031.
Stove et al., "Multiple gene knock-down by a single lentiviral vector expressing an array of short hairpin RNAs," Electronic Journal of Biotechnology, vol. 9, No. 5, Oct. 15, 2006.
Sveger et al., "The Liver in Adolescents with α1-Antitrypsin Deficiency," Hepatology, vol. 22, No. 2, 1995, pp. 514-517.
Teckman, "Liver Disease in Alpha-1 Antitrypsin Deficiency: Current Understanding and Future Therapy," Journal of Chronic Obstructive Pulmonary Disease, 10(S1):35-43, 2013.
Ter Brake et al., "Lentiviral Vector Design for Multiple shRNA Expression and Durable HIV-1 Inhibition," The American Society of Gene Therapy, vol. 16, No. 3, 557-567, Mar. 2008.
Vannucci et al., "Viral vectors: a look back and ahead on gene transfer therapy," New Microbiologica, 36, 1-22, 2013.
Wiznerowicz et al., "Conditional Suppression of Cellular Genes: Lentivirus Vector-Mediated Drug-Inducible RNA Interference," Journal of Virology, Aug. 2003, pp. 8957-8961.
Yin et al., "Non-viral vectors for gene based therapy," Nature Reviews Genetics, vol. 15, Aug. 2014, pp. 541-555.
Extended European Search Report issued in European Patent Application No. 18 82 0787 dated Feb. 12, 2021.
Cruz et al., "In vivo post-transcriptional gene silencing of alpha-1 antitrypsin by adeno-associated virus vectors expressing siRNA", Laboratory Investigation, Jun. 25, 2007, vol. 87, No. 9, pp. 893-902.

* cited by examiner

Fig 2

NUCLEIC ACID MOLECULES AND THEIR USE IN THERAPY

CROSS-REFERENCE TO RELATED APPLICATIONS

This application claims priority from Swedish application 1750774-0 filed on 19 Jun. 2017, which is incorporated herein by reference in its entirety.

TECHNICAL FIELD

The present invention relates to products and methods for therapy using nucleic acid molecules, and in particular in relation to treatment of alpha-1-antitrypsin deficiency. The invention also relates to pharmaceutical compositions comprising the nucleic acids and/or delivery vehicles comprising the nucleic acids, and their use in manufacture of pharmaceutical compositions for use in therapy, such as treatment of alpha-1-antitrypsin deficiency.

BACKGROUND

Alpha-1-antitrypsin (AAT) is a 52 kDa glycoprotein with a half-life of 4-5 days in the serum. In the lungs, wild-type AAT inactivates the neutrophil elastase that, if active, would degrade lung parenchyma proteins and connective tissue. The function of AAT is not limited to the inhibition of the elastase from neutrophils, pancreas or bacteria. AAT also neutralises proteinase-3, myeloperoxidase, cathepsin G, α-defensins from neutrophils, chymases and trypsinases, granzyme-B from T lymphocytes, specific kallikreins and the coagulation cascade serine proteinases plasmin, thrombin, urokinase and factor Xa. It has been suggested that AAT may have several anti-inflammatory and tissue-protective properties by reducing the expression of leukotriene B4 and pro-inflammatory cytokines tumor necrosis factor-α (TNF-α), interleukin (IL)-1β, IL-6, IL-8, IL-32 and monocyte chemoattractant protein-1. AAT inhibits caspases 1 and 3 protecting lung alveolar and endothelial cells, pancreas β cells, cardiomyocytes and skin fibroblasts from apoptosis (Serres and Blanco, 2014). 80% of AAT is synthesised in the liver and additional amounts are synthesised in monocytes, macrophages, pancreas, lung alveolar cells, enterocytes, endothelium and some cancers. The total amount produced per day is 34 mg per kg bodyweight per day. Only 0.5-10% of AAT reaches the biological fluids, e.g. the alveolar fluid.

Mutations of the AAT-gene are linked to the hereditary disorder, alpha-1-antitryspin deficiency (AATD). AATD is an inherited condition affecting both lungs and the liver. The disease is caused by deficient variants of alpha-1-antitrypsin (AAT), thereby limiting their protective and regulatory activity against tissue modifying enzymes and inflammation.

In the lungs, wild-type AAT inactivates the neutrophil elastase that, if active, would degrade lung parenchyma proteins and connective tissue. In patients with AATD, the protective function of AAT in the lungs against neutrophil elastase has been lost and patients may develop emphysema of the lungs by middle adulthood resulting in a marked decline in lung function (Kramps et al, 1980). The patients are severely limited in their quality of life and need life-long inhalation therapy to control their respiratory disease. Ultimately, the patients require lung transplantation to survive.

The liver-associated variant of AATD affects a minority of disease-carrying individuals and may exhibit elevated liver enzymes and hyperbilirubinemia in newborns (Sveger 1988). 15-19% of patients over age of 50 with a history neonatal jaundice will develop severe liver disease (Cox and Smyth, 1983).

AATD has a high prevalence in Northern European countries occurring at one per 1:1500-1:3000 individuals (Eriksson, 1965). Once AATD is suspected it can easily be diagnosed by serum blood samples and genetic testing. The most common deficient variant of alpha-1-antitryspin (AAT) is the protease inhibitor PI type Z (Pi*ZZ or Z-AAT, where both wild-type Pi*M alleles are exchanged with two Z alleles) containing a Gly342.Lys amino acid exchange. The mutation causes conformational change leading to abnormal interaction between Z-AAT monomers that can aggregate to polymers in the hepatocyte's cytoplasm (Carrell et al., 1996). Non-degraded accumulated Z-AAT polymers not only activate the proteosomal and autophagy degradative pathways (Lawless et al., 2004; Hidvegi et al., 2005; Teckman et al., 2000), but also inflammatory pathways, leading to chronic hepatitis, fibrotic remodelling of the liver and finally end-stage liver disease (Sveger and Eriksson, 1995).

The inability of hepatocytes to secrete Z-AAT dimers further results in lowered AAT serum levels and diminished activity against neutrophil elastase in the lung parenchyma, thereby greatly increasing the risk for the development of lung emphysema. The main function of M-AAT is to inhibit tissue modifying enzymes such as neutrophil elastases in the lung parenchyma. In absence of sufficient levels of active AAT, neutrophil elastase is allowed to breakdown lung parenchyma, thereby triggering the events that cause lung emphysema with time. In addition, Z-AAT lacks inhibitory ability compared to M-AAT contributing to the failing inhibitory effect of the minute levels of secreted Z-AAT.

The most-prevalent AAT mutant alleles are Pi*S and Pi*Z with a prevalence of 5 to 10% and 1 to 3%, respectively. Their combined phenotypes differ from wild-type Pi*MM by significantly reduced serum levels of circulating AAT resulting in vanishing inhibitory effect in the lungs. Pi*Z aggregates to polymers in hepatocytes, is inaccessible to proteasomal breakdown and leads to liver disease. A homozygous Pi*ZZ patient has a decrease of serum levels to 10-20% of normal and has a greatly increased life-time risk of developing lung emphysema.

In patients with two SS alleles (PiSS phenotype) AAT levels are decreased to 40% of normal levels, but their ability to inhibit neutrophil elastases is not impaired. AAT in patients with PiF phenotype has a severely impaired ability to inhibit neutrophil elastases and may develop lung emphysema.

The most severe cases of AATD are caused by the rare Pi null-null phenotype, where AAT production is completely abolished by frame shift mutation, mutations leading to an early termination codon, splicing errors or deletions in coding regions of the gene.

AATD is not only associated with lung and liver disease, but also with necrotising panniculitis (McBean et al., 2003). It has also been suggested that intracranial aneurysms, fibromuscular dysplasia, bleeding disorders, anterior uveitis, systemic necrotizing vasculitis and Wegener granulomatosis (Cox 1994; Fearnley et al., 1988; Mazodier et al., 1996; Barnett et al., 1999). Penetrance is rare and symptoms can be efficiently treated with augmentation therapy which is used off-label in regards to panniculitis. In Pi*ZZ, pi*SZ and Pi*MZ phenotypes some cases of AATD related systemic vasculitis have been described. AAT inhibited proteinase 3 is suggested to play an important role in the onset in this systemic inflammation.

State-of-the-art treatment of AATD consists of routine therapy in obstructive pulmonary disease and the augmentation therapy. In augmentation therapy, alpha-1-antitrypsin from healthy donors is purified, pooled and injected into the diseased AATD patient. Unfortunately, the augmentation therapy is costly, non-curative and is limited to patients without strong impairment of their lung function (Petrache et al., 2009). Furthermore, the augmentation therapy does not improve or cure AATD related liver failure and liver transplantation remains until today the only known curative method to resolve AATD-induced progressive liver disease.

Novel therapies are becoming available with the development of gene therapeutical approaches to eliminate genetic disorders. Examples of novel therapies are the administration of aerosols containing purified alpha-1-antitrypsin (Hubbard & Crystal, 1990). The application of synthetic inhibitors of neutrophil elastase, of chemical chaperones, of synthetic polypeptides that block Z-AAT and antioxidant therapies have also been proposed to inhibit progression of emphysema development, however, efficacy have not been evaluated in trials (Mahadeva et al., 2002; Parfrey et al. 2004, Burrows et al., 2000; Sandhaus 2004). Promising in vitro results have been achieved showing the accelerated autophagy degradation of Z-AAT polymers induced by carbamazepine (Hidvegi et al., 2010). The development of recombinant AAT has been proposed to meet the need for AAT substitute. However, the lack of or improper glycosylation of the recombination protein by using host species other than humans contributes to inacceptable half-life and immunogenicity of the synthetic AAT (Karnaukhova et al., 2006; Spencer et al., 2005).

Gene therapy is one of the most promising opportunities to favourably modulate gene expression and to cure genetic disease. In common, gene therapy is defined as the delivery of DNA, mRNA, siRNA, microRNA or antisense oligonucleotides into the cells as a therapeutic drug to treat diseases, and it can be performed using various viral and non-viral delivery vehicles.

RNA Interference

RNA interference (RNAi) is a naturally occurring gene regulatory mechanism endogenous for all cells. In nature, it is mediated by small non-coding micro RNA molecules that target and regulate the expression of a specific set of genes. Researches have learned to utilise this tool with the aim to downregulate distinct target genes. Various methods have been developed to introduce RNAi mediators. In general, the introduced RNA molecules have to be complimentary and specific to the aimed target gene sequence to achieve effective downregulation and to minimise the risk of off-target downregulation of genes that share highly similar targeted nucleotide sequences.

Most commonly, scientist transfect target cells with synthetic double stranded RNA (dsRNA). The endoribonuclease Dicer degrades the dsRNA into short interfering RNA (siRNA) of ~22 bp in length and siRNAs are loaded into the effector complex RNA-induced silencing complex (RISC). Within the RISC, siRNAs are unwound and hybridize with complementary mRNA sequences of the target gene. The mRNA molecules are subsequently cleaved by the argonaute proteins and rendered useless for protein translation, thereby reducing protein synthesis of this specific gene.

RNAi has become an important tool in gene therapeutical approaches to correct the expression of misfolded genes in conformational diseases. Lentiviral delivery allow the long-lived expression of short hairpin RNAs (shRNAs) from a lentiviral complex integrated into the genome as used in this application. Lentiviral transduction can also be achieved in hard-to-transfect and non-dividing cells making RNAi accessible in all sorts of target cells. In the case of shRNAs. shRNA molecules are transcribed as pri-microRNA, processed into pre-microRNA by the Drosha complex and exported from the nucleus by Exportin-5. Pre-microRNA is translocated to the Dicer complex and degraded in siRNA and subsequently integrated into the RISC to degrade target gene mRNA (Brummelkamp et al., 2002).

siRNA oligonucleotide transfer describes a method in which chemically synthesised 19-21 bp oligonucleotides are delivered into target cells by delivery vectors and incorporated into the RNA interference (RNAi) machinery. In vivo, siRNA oligonucleotides are prone to elimination by endonucleases and immune responses, mechanisms that can be overcome by chemical modification of the introduced siRNA oligonucleotides such as the exchange by 2'-OH groups of ribose with O-methyl or 2'-fluoro groups. In contrast, interaction of siRNA conjugates can facilitate interaction with serum proteins and delivery into specific target cells such as hepatocytes. However, such conjugates can also activate clearing by the mononuclear phagocyte system. In addition, siRNA are small particles that can easily pass through the glomerular filtration barrier. Some siRNA nanoparticle delivery systems may also undergo degradation at the glomerular filtration barrier through electrostatic interaction. Promising siRNA nanoparticles such as Dynamic PolyConjugates (DPCs) and triantennary N-acetylgalactosamine (GalNAc) conjugates deliver the therapeutic siRNA in the first pass through the liver and are favourable application in liver directed gene therapy. Cyclodextrin polymers (CDPs) have been developed as non-viral delivery vehicles due to their low toxicity and Lipid based siRNA nanoparticles, namely stable nucleic acid-lipid particle (SNALP), are efficiently incorporated into the liver involving an apolipoprotein E (APOE)-dependant internalisation. Liver parenchyma cells are normally accessed by nanoparticles through the miniature fenestrations within the sinusoidal barrier. To enhance cellular entry conjugates can be coupled to adequate ligands that attach to target cell receptors mediating endocytosis and facilitating release from endosomes.

Non-Viral Vehicles:

Non-viral gene therapy vehicles have been reviewed in detail by Ramarmooth and Narvekar and by Yin and co-workers, and are summarised in the following sections:

Non-viral vehicles address some of the limitations associated with viral gene vectors. Particularly, immune responses are normally not triggered as introduced nucleotides are coated with synthetic coating material that represents an unknown antigen to the human immune system. There is also the possibility that non-viral vectors may deliver larger payloads to target cells than do viral vectors (Pack et al, 2005). However, development of non-viral vectors as clinically applicable tools has been restricted due to their greatly reduced delivery efficiency (Putnam et al., 2006).

Various methods of non-viral vehicles may not be applicable in humans because of the size and the constitution of the human body. Such methods include a) gene gun/ballistic DNA where DNA particles coupled to heavy metals are translocated at high speeds through cellular membranes by using electric or helium gas discharge; b) electroporation, where cell membrane pores are formed by applying an electrical field allowing nucleotides to enter the target cell; c) sonoporation, where externally applied ultrasound waves temporarily render the target cell's membranes permeable to oligonucleotides that are trapped with micro-bubbles, latter being composed of an inert gas and a biological compound such as lipids; d) hydroporation, in which large volumes of DNA solution are injected within a specific time frame leading to permeabilisation of capillary endothelium and pores in the membrane of parenchymal cells; e) magnetofection, where DNA molecules are coupled to magnetic nanoparticles, injected into the body, translocated to the target site by external magnets, where DNA is subsequently released by enzymatic cleavage from the nanoparticle, charge interaction or degradation; f) needle injection, where DNA material in directly injected into the target cell. Other methods such as mechanic massage or photoporation, i.e. the use of a pulsed laser to generate cell membrane pores for transgene entry, have never been published (Yin et al., 2014; Ramarmooth and Narvekar, 2015).

In recent years, many biological, chemical and synthetic compounds have been modified to overcome the barriers of non-viral gene delivery. Entrapment of therapeutic DNA is obligatory to evade degradation by endonucleases and to improve in vivo half-life. The vectors have to ensure translocation to the correct target tissue, extravasation from the blood vessel through the endothelium, uptake by the target cell and endosomal escape to avoid intracellular degradation. Once delivered into the cytosol, transgenic DNA has to penetrate the nuclear complex to exert its transcription activity. Moreover, expression of the transgene should be continuous. Normally plasmid DNA is used as expression vectors as they do not integrate into the genome, thereby minimising the risk of insertional mutagenesis. Expressional activity is controlled by promoters such as promoters derived from cytomegalovirus (CMV), respiratory syncytial virus (RSV) and simian virus (SV40) although these are transient. The use of mammalian promoters such as the human ubiquitin C (UBC) and the eukaryotic translation elongation factor 1 alpha 1 (EEF1A1) promoters demonstrate constitutive expression and are the preferred choice for enduring transgene expression in targeted tissue cells. Off-target transgene expression can be restricted by using tissue specific promoters such as liver specific alpha fetoprotein promoter albumin enhancer-promoter promoter (AFP-ALB). Introduced siRNA, miRNA and shRNA have to be able to integrate into the RISC machinery for effective knockdown of target genes. mRNA molecules delivery by gene therapy vehicles have to be effectively forwarded to the translational machinery in the cytosol for transgene expression (Yin et al., 2014)

Lipid-based DNA vectors represent the oldest form of non-viral vectors. Phospholipids and cationic lipids such as 1,2-di-O-octadecenyl-3-trimethylammonium propane (DOTMA), 2,3-dioleyloxy-N-[2-(sperminecarboxamido) ethyl]-N,N-dimethyl-1-propanaminium trifluoroacetate; N-(2-{[N(2),N(5)-bis(3-aminopropyl)ornithyl] amino}ethyl)-N,N-dimethyl-2,3-bis[(9Z)-octadec-9-en-1-yloxy]propan-1-aminium trifluoroacetate (DOSPA), N-[1-(2,3-Dioleoyloxy)propyl]-N,N,N-trimethylammonium methyl-sulfate (DOTAP) and 1,2-dimyristyloxy-propyl-3-dimethyl-hydroxy ethyl ammonium bromide DMRIE efficiently engulf negatively charged plasmid DNA and mediate transgene delivery. Neutral helper lipids such as cholesterol and dioleoyl phosphatidylethanolamine (DOPE) have enhanced transfection activity and DNA-lipid hybrid stability. However, the usefulness of lipid-based DNA vectors is greatly questioned because of low efficacy in transgene delivery, immune responses, relatively poor stability and rapid clearance from the blood stream. Synthetic cation lipids can be fabricated also as emulsion or as solid lipid nanoparticles. Peptides can also be attached to lipid based-vehicles in order to selectively direct the vehicles to specific target genes.

Polymeric vectors such as poly (L-Lysine) (PLL)-based vehicles condensate DNA and can be used for liver-targeted gene therapy. Cell translocation through the membrane is mediated by the interaction of positively charged moieties of PLL with negatively charged glycoproteins of the cell membrane. However, they are marked by poor transfection efficiency because of their inability to overcome intracellular endosomes and their proven cytotoxicity. The hydrophilic polymer polyethylene glycol (PEG) has been demonstrated to increase circulation times of PLL-based vehicles by minimising interaction with serum components. Polyethyleineimine (PEI) vectors are proposed to increase endosomal escape by the buffering capacity of the large amount of amine groups, reducing the acidification of endosomes and their rupture, thereby releasing the endocytosed gene therapy vehicle. Co-polymers of PEG-PEI have been demonstrated to improve vehicle stability and cytotoxicity.

Although mRNA molecules are less stable than DNA as gene therapeutical candidates, they are characterised by their reduced immunogenicity. Their point of action is localised in the cytosol, making the barrier of nuclear translocation obsolete. Specific modifications such as the incorporation of 2-thiouridine, 5-methylcytidine or pseudouridine reduce immune stimulation or degradation. mRNA can also be encapsulated with polymer-lipid formulations and have been described in successful experiments using intramuscular and intranasal gene transfer.

Virus-Based Vehicles

Viral gene delivery vectors have been broadly investigated and optimised to become promising and efficient tools of gene delivery. Viruses represent an ideal tool to manipulate genetic expression of eukaryotic cells as they naturally possess the ability to enter the cells, escape the endosomal degradation and release the incorporated genetic information into sites of replication within the target cells. Viral gene therapy uses this unique ability and simultaneously modifies viral vehicles in a way that prohibits them from producing replicating viruses. Viral vectors have been successfully used in a number of clinical trials where genetic disorders were corrected. Nevertheless, there have also been misfortunes in which treated patients have died. Various viral vectors vehicles—each derived from distinct virus strains—have been developed with the aim to find the ideal candidate for viral gene therapy ensuring they meet the hard safety criteria imposed in human trials. The ability to infect specific types of target cells is called tropism. Tropism of viral vectors can be limited or extended by modifying the genetic constituents of the virus that are responsible for the interaction with the target upon cell entry. Modern viral vectors are made replication-deficient by deletion of genetic elements and their production rely on the presence of helper viruses or DNA acting in trans providing the missing genes. This DNA can be supplemented either as plasmid DNA that is co-transfected with vector DNA or by using producer cell lines that have been stably transfected with DNA containing the missing information for viral production. Vannucci and co-workers have in detail reviewed some viral vectors suited for gene therapy.

Adenoviral vectors (AdV) are derived from Adenoviruses, naturally causing mild respiratory and gastroenteric disease. Their prime advantages are their low pathogenicity, wide tropism, the high level of expression and favourable features in terms in efficient gene therapy. However, because of their natural abundance, there is a high level of pre-existing immunity against adenoviruses with common serotypes (Bessis et al., 2004). Therefore, AdV in gene therapy are derived from rare serotypes minimising the risk of immune reactions upon application. Nowadays, third generation AdV allow the incorporation of 8 kb of heterogenic DNA and ensure the production of vectors particles at high titers. However, the expression of transgenes is transient and AdV demonstrate high immunogenicity, exemplified by one fatality caused by a cytokine storm against the injected AdV.

Adeno-associated viruses (AAV) belong to the Parvoviridae family and are dependent on co-infection of helper viruses. When helper viruses are absent, AAV integrate into chromosome 19 and remain silent until the co-infection with a helper virus that ensures completion of replication. On the virus parental strain, the structural proteins rep and cap are flanked by inverted terminal repeats (ITRs). When producing AAV vectors, the structural proteins are provided in trans as separate plasmids while a eukaryotic promoter and a transgene replace the rep and cap sequences between the ITRs. The advantages of AAV vectors are their low pathogenicity, the possibility to infect dividing and non-dividing cells, the site specific integration in the host genome, the low immunogenicity and their wide cellular tropism. However, the size of the promoter-transgene sequence is limited to only 5 kb and initiation of expression is delayed. The need for a helper virus has until recently been an obstacle, however, necessary genes from the helper virus can efficiently be provided by a separate helper plasmid.

Herpes simplex viruses (HSV) are large viruses that mainly infects skin, mucosa, neurons and B lymphoid cells. Vectors particles are produced in large quantities ($1*10^{12}$ plaque forming units/ml) and cloned transgenic constructs can be as large as 50 kb due to the deletion of several unnecessary herpes virus genes from the parental strain. Unfortunately, prevalence of HSV in humans is 70% and may trigger immune reaction and degradation of HSV-derived vectors in most patients upon exposure. The cytotoxic effect in vitro of HSV derived vectors may be a limiting factor in advancing to clinical application. There is also a risk that HSV-derived vectors may recombine with quiescent HSV endogenous to the host to create a new virus strain that is uncontrollable.

Retroviruses consists of a genome encoding for capsid protein (gag), the replication enzymes (pol) and the envelope glycoprotein (env). They are flanked by long terminal repeats (LTRs) that act as expression promoters. When retrovirus infect the host cell, the capsid is released into the cytoplasm where reverse transcriptase (RT) converts the viral RNA genome into a double stranded DNA that migrates to the nucleus and randomly integrates into the host genome, allowing constituent transgene expression. The structural proteins gag, pol, and env can be deleted, making room for eukaryotic-transgene inserts with a size of 9 kb. Structural plasmids provide the necessary structural genes in trans, minimising the risk of recombination and the spontaneous generation of retroviral particles. The env glycoprotein can be exchanged with different envelope protein derived from various viral strains, thereby modifying its tropism. This approach is called pseudotyping and allows viruses to be redirected to specific target cells. Retroviruses are produced in high titers and are normally not degraded by the host immune system as there is no pre-existing immunity. Unfortunately, retrovirus do integrate randomly, leading to insertional mutagenesis and leukaemia (Baum et al., 2006). They are also unsuitable to infect non-dividing cells, greatly limiting their tropism and clinical application. Researches have tried to overcome the problem of insertional mutagenesis by integrating insulator sequences inserted downstream of the LTRs and thereby almost eliminating the promotional activity of LTRs. The use of self-inactivating vectors disrupts the promotional activity of the 5' LTR by truncating the LTR during the reverse transcription. Expression of transgenes located between the LTRs is then solely dependent on heterogenic promoters such as CMV promoter, EF promoter and SFFV promoter.

Lentiviruses share some of the genetic information of retroviruses. In addition, their genome contains some regulatory genes to regulate virus replication and to evade the host immune system. The use of lentiviral vectors allows the infection of dividing and non-dividing cells with heterogenic DNA with a size up to 9 kb. In the third generation vector, all regulatory genes are deleted from the lentiviral vector. However, the regulatory gene rev is provided in trans on a separate plasmid. The rev responsive element were retained on the lentiviral transfer vector and packaging vector. Vectors are self-inactivating minimising the risk of off-target promotional activity of LTRs. Pseudotypization can be achieved by exchanging the env plasmid provided in trans. Most commonly used is vesicular stomatitis virus glycoprotein (VSV-G) that uses membrane phospholipid for cell entry. VSV-G is characterised by a broad tropism and high transduction efficiency. Cell-specific expression of transgenes can be achieved either by different pseudotypization or be using a tissue-specific transgene promoter. US 2015/0011607 A1 discloses compounds, compositions and methods useful for reducing α-1 antitrypsin target RNA and protein levels via use of dsRNAs, e.g., Dicer substrate siRNA (DsiRNA) agents. One DsiRNA disclosed therein is referred to as SEQ ID NO 3279, and corresponds to shRNA2 (SEQ ID NO: 41) in the present disclosure.

SUMMARY OF THE INVENTION

The present invention aims to provide an effective treatment of alpha-1-antitrypsin deficiency by decreasing production of misfolded alpha-1-antitrypsin protein, thereby decreasing the amount of aggregated Z-AAT in hepatocytes.

The present invention also aims to provide an effective treatment of alpha-1-antitrypsin deficiency by providing a functional alpha-1-antitrypsin protein, i.e. alpha-1-antitrypsin protein having an inhibitory activity on tissue-modifying enzymes comparable to human wild-type alpha-1-antitrypsin protein, in combination with decreased production of misfolded alpha-1-antitrypsin protein.

The present invention also aims to increase levels of circulating alpha-1-antitrypsin above the threshold needed to ensure anti-inflammatory systemic activity of alpha-1-antitrypsin and to subsequently decrease the incidence of lung emphysema, panniculitis, aneurysms, fibromuscular dysplasia, bleeding disorders, anterior uveitis, systemic necrotizing vasculitis and Wegener granulomatosis The invention fulfils its aims by providing nucleic acid molecules, viral and non-viral delivery vehicles, and methods as disclosed herein.

In a first aspect, the invention relates to a ribonucleic acid molecule consisting of 19, 20, or 21 nucleotides and comprising a sequence selected from SEQ ID NO: 39, 40, 43 and 44.

In a further aspect, the invention relates to a chemically modified ribonucleic acid consisting of 19, 20, or 21 nucleotides and comprising a sequence selected from SEQ ID NO: 39, and 43.

In one embodiment of this aspect, the chemically modified ribonucleic acid is modified in the phosphodiester backbone, such as by incorporation of phosphorothioate, boranophosphate, or methylphosphonate; or in the sugar backbone such as at the 2'-position of the ribose unit, such as by substitution of the 2'-OH group for —O—CH$_3$, —CH$_2$CH$_2$OCH$_3$, or —F or by incorporation of 2-thiouridine, 5-methylcytidine or pseudouridine.

In a further aspect, the invention relates to an RNA molecule consisting of 40-100 nucleotides, comprising two sequences spaced 4-10 nucleotides apart, wherein the two sequences are selected from the sequence pairs: SEQ ID NO: 39 and 40; and SEQ ID NO: 43 and 44.

In a further aspect, the invention relates to a DNA molecule comprising at least one nucleotide sequence complementary to at least one RNA molecule according to the invention such as one or two RNA molecules according to the invention.

In one embodiment of this aspect, the nucleotide sequence complementary to an RNA molecule according to the invention is operably linked to a single RNA polymerase promoter sequence.

In one embodiment of this aspect, the DNA molecule comprises at least two nucleotide sequences complementary to at least two different RNA molecule according to the invention, wherein each nucleotide sequence complementary to an RNA molecule according to the invention is independently operably linked to an RNA polymerase promoter sequence and wherein the RNA polymerase promoter sequence is the same for each nucleotide sequence complementary to an RNA molecule according to the invention.

In one embodiment of this aspect, the DNA molecule comprises at least two nucleotide sequences complementary to at least two different RNA molecule according to the invention, wherein each nucleotide sequence complementary to an RNA molecule according to the invention is independently operably linked to an RNA polymerase promoter sequence and wherein the RNA polymerase promoter sequence is different for each nucleotide sequence complementary to an RNA molecule according to the invention.

In one embodiment of this aspect, each RNA polymerase promoter sequence present in the DNA molecule is selected from RNA polymerase promoters H1, 7SK, and U1.

In a further aspect, the invention relates to a DNA molecule comprising a sequence encoding a functional human alpha-1-antitrypsin and having at least 90% identity to SEQ ID NO: 1, characterized in that said sequence comprises a plurality of point mutations in relation to SEQ ID NO: 1, said point mutations rendering an RNA-transcript of said DNA molecule resistant to gene silencing by RNA interference mediated by an RNA molecule according to the invention.

In one embodiment of this aspect, the point mutations in relation to SEQ ID NO: 1 are selected from the group: T919A, C920G, T921C, C924A, A925T, G926C, C927T, T928C, A930G, T933C, T934C, A936C, T984C, A987G, C988T, G990A, C993T, C996T, T999A.

In one embodiment of this aspect, the DNA molecule comprises the following point mutations in relation to SEQ ID NO: 1: T919A, C920G, T921C, C924A, A925T, G926C, C927T, T928C, A930G, T933C, T934C, A936C.

In one embodiment of this aspect, the DNA molecule comprises the following point mutations in relation to SEQ ID NO: 1: T984C, A987G, C988T, G990A, C993T, C996T, T999A.

In one embodiment of this aspect, the DNA molecule comprises the following point mutations in relation to SEQ ID NO: 1: T919A, C920G, T921C, C924A, A925T, G926C, C927T, T928C, A930G, T933C, T934C, A936C, T984C, A987G, C988T, G990A, C993T, C996T, T999A.

In one embodiment of this aspect, the DNA molecule comprises a point mutation G75A in relation to SEQ ID NO: 1.

In one embodiment of this aspect, the DNA molecule encodes a protein comprising an amino acid sequence according to positions 25-418 of SEQ ID NO: 45.

In a further aspect, the invention relates to an RNA molecule comprising a nucleotide sequence complementary to a DNA molecule according to the invention.

In a further aspect, the invention relates to a virus particle comprising a recombinant viral genome, characterized in that said genome comprises a DNA molecule comprising the sequence of a DNA molecule according to the invention In a further aspect, the invention relates to a virus particle comprising a recombinant viral genome, characterized in that said genome comprises an RNA molecule comprising a nucleotide sequence complementary to a DNA molecule according to the invention.

In a further aspect, the invention relates to a vehicle for delivery of nucleic acid material to a human cell in vivo, characterized in that said vehicle comprises a DNA molecule comprising the sequence of a DNA molecule according to the invention, and/or an RNA molecule according to the invention.

In one embodiment of this aspect, the vehicle is selected from the group plasmid DNA, lipid-based vectors, and polymeric vectors.

In a further aspect, the invention relates to a method for treatment of a subject comprising administering a nucleic acid molecule according to the invention, a virus particle according to the invention, or a vehicle according to the invention, to said subject.

In one embodiment of this aspect, a vehicle according to the invention is delivered to the subject by way of gene gun/ballistic DNA, electroporation, sonoporation, hydroporation, magnetofection, needle injection and/or other methods facilitating the incorporation of DNA or RNA into the cell leading to a modified transcription and expression of target genes.

In one embodiment of this aspect, the subject has alpha-1-antitrypsin deficiency In one embodiment of this aspect, the subject's genome is heterozygous or homozygous for a G342K mutation in a gene encoding alpha-1-antitrypsin.

In one embodiment of this aspect, the alpha-1-antitrypsin deficiency manifests as liver cirrhosis, pulmonary emphysema, necrotising panniculitis, systemic vasculitis, (intracranial) aneurysms, fibromuscular dysplasia, bleeding disorders, anterior uveitis, systemic necrotizing vasculitis and Wegener granulomatosis.

In a further aspect, the invention relates to a nucleic acid molecule according to the invention, a virus particle according to the invention, or a vehicle according to the invention, for use in a method for treatment according to the invention.

In one embodiment of this aspect, a vehicle according to the invention is delivered to the subject by way of gene gun/ballistic DNA, electroporation, sonoporation, hydroporation, magnetofection, needle injection and/or other methods facilitating the incorporation of DNA or RNA into the cell leading to a modified transcription and expression of target genes.

In one embodiment of this aspect, the subject has alpha-1-antitrypsin deficiency.

In one embodiment of this aspect, the subject's genome is heterozygous or homozygous for a G342K mutation in a gene encoding alpha-1-antitrypsin.

In one embodiment of this aspect, the alpha-1-antitrypsin deficiency manifests as liver cirrhosis, pulmonary emphysema, necrotising panniculitis, systemic vasculitis, (intracranial) aneurysms, fibromuscular dysplasia, bleeding disorders, anterior uveitis, systemic necrotizing vasculitis and Wegener granulomatosis.

In a further aspect, the invention relates to the use of a nucleic acid molecule according to the invention, a virus particle according to the invention, or a vehicle according to the invention, in the manufacture of a pharmaceutical composition.

In one embodiment of this aspect, the pharmaceutical composition is for use in a method of treatment according to the invention.

DESCRIPTION OF THE DRAWINGS

FIG. 2: Insertion of shNRA into pLVTHM: Paired shRNA oligonucleotides were annealed and cloned into pLVTHM using the MluI and ClaI restriction sites to yield pLVTHM.shRNA1, pLVTHM.shRNA2 or pLVTHM.shRNA3. The H1 promoter regulating the RNA Polymerase III-mediated expression of shRNA is located upstream of the MluI/ClaI shRNA insertion site. The EcoRI site at the 5'-end of the H1 promoter was used to generate the multicistronic lentiviral transfer vector such as pLVTHM.shRNAx3.sAAT2 allowing combinational expression of multiple shRNAs and the recombinant sAAT/sAAT2 protein simultaneously. The sequence in FIG. 2 is provides as SEQ ID NO: 46 in the appended sequence listing.

SEQUENCES

Figure 1:
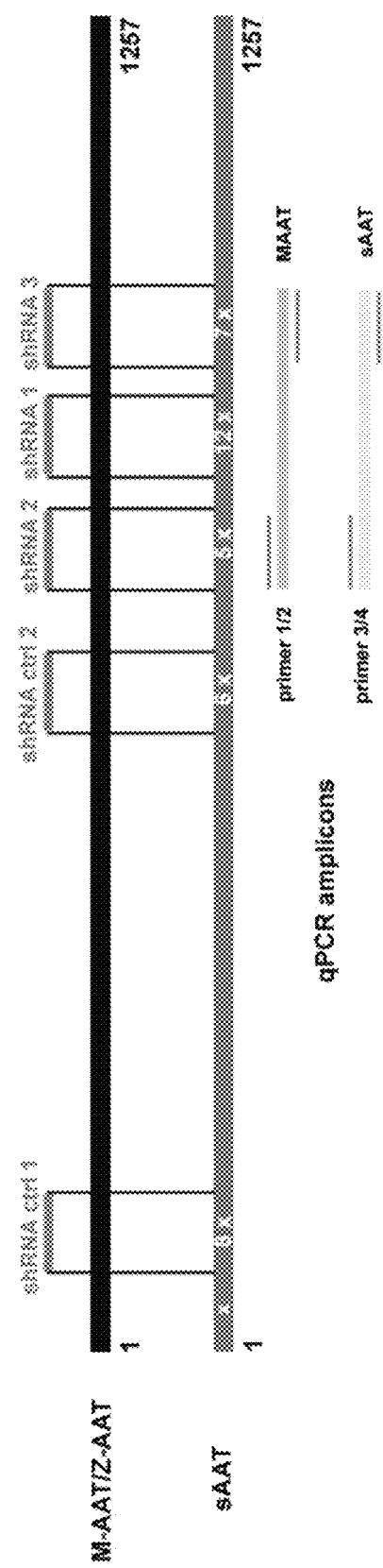
FIG. 1: shRNA targets and synthetic alpha-1-anitrypsin: The shRNA target sites are marked schematically within the wild-type M-AAT and the defective Z-AAT sequence bars (black gene bar). In sAAT and sAAT2, the silent point mutations have been incorporated at the sites targeted by shRNAs to render sAAT/sAAT2 resistant to shRNAs and to delete the in-frame BamHI site (the x at the 5'-end of sAAT). sAAT2 does not have incorporated the silent point mutations at the sRNA ctrl 1 and shRNA ctrl 2 target sites. However, the silent point mutations at the shRNA 1, 2 and 3 target sites are still incorporated. shRNA ctrl 1 and shRNA ctrl 2 are positive control shRNAs for knock-down of alpha-1-antitrypsin expression by the means of RNA interference. shRNAs 1, 2, and 3 are newly designed shRNAs that aim at previously untargeted sites of M-AAT and Z-AAT. The number of point mutations has been defined in the sAAT/sAAT2 gene bars (grey gene bars). E.g. at the site for shRNA1, 12 point mutations were introduced to acquire resistance against shRNA1 in sAAT/sAAT2. Specifically designed qPCR primers targeting the mutated sites of sAAT (primers 1/2) allowed the synthesis of sAAT-specific qPCR amplicons to discriminate against qPCR amplicons derived solely from M-AAT using M-AAT specific primers 3/4. The sAAT recombinant protein sequence was cloned into unicistronic pSFFV.IRES.dTom to yield pSFFV.sAAT.IRES.dTom. The sAAT2 was cloned into pLVTHM.shRNA1 to yield a multicistronic lentiviral transfer vector allowing co-expression of multiple shRNAs and a recombinational protein. sAAT was cloned into pSFFV.sAAT.IRES.dTomato to yield LV-sAAT upon lentiviral transduction. sAAT2 was cloned into pLVTHM.sHRNA1x3 to yield pLVTHM.shRNA1x3.sAAT2 where the genetic elements needed for the expression of shRNA and sAAT2 are combined within one lentiviral transfer vector.

The following sequences are relevant to the present disclosure and included in the appended sequence listing.

Alpha-1-antitrypsin sequences
Open reading frame of native alpha-1-antitrypsin
(M-AAT), NM_000295.4 (SEQ ID NO: 1):
ATGCCGTCTTCTGTCTCGTGGGGCATCCTCCTGCTGGCAGGCCTGTGCTG

CCTGGTCCCTGTCTCCCTGGCTGAGGATCCCCAGGGAGATGCTGCCCAGA

A<u>GACAGATACATCCCACCATG</u>ATCAGGATCACCCAACCTTCAACAAGATC

ACCCCCAACCTGGCTGAGTTCGCCTTCAGCCTATACCGCCAGCTGGCACA

CCAGTCCAACAGCACCAATATCTTCTTCTCCCCAGTGAGCATCGCTACAG

CCTTTGCAATGCTCTCCCTGGGGACCAAGGCTGACACTCACGATGAAATC

CTGGAGGGCCTGAATTTCAACCTCACGGAGATTCCGGAGGCTCAGATCCA

TGAAGGCTTCCAGGAACTCCTCCGTACCCTCAACCAGCCAGACAGCCAGC

TCCAGCTGACCACCGGCAATGGCCTGTTCCTCAGCGAGGGCCTGAAGCTA

GTGGATAAGTTTTTGGAGGATGTTAAAAAGTTGTACCACTCAGAAGCCTT

CACTGTCAACTTCGGGGACACCGAAGAGGCCAAGAAACAGATCAACGATT

ACGTGGAGAAGGGTACTCAAGGGAAAATTGTGGATTTGGTCAAGGAGCTT

GACAGAGACACAGTTTTTGCTCTGGTGAATTACATCTTCTTTAAAGGCAA

ATGGGAGAGACCCTTTGAAGTCAAGGACACCGAGGAAGAGGACTTCCACG

TGGACCAGGTGACCACCGTGAAGGTGCCTAT<u>GATGAAGCGTTTAGGCATG</u>

TTTAACATCCAGCACTGTAAGAAGCTGTCCAGCT<u>GGGTGCTGCTGATGAA</u>

<u>ATA</u>CCTGGGCAATGCCACCGCCATCTTCTTCCTGCCTGATGAGGGGAAAC

TACAGCACCTGGAAAATGAACTCACCCACGATATCATCACCAAGTTCCTG

GAAAATGAAGACAGAA<u>GGTCTGCCAGCTTACATTTAC</u>CCAAACTGTCCAT

TACTGGAACCTATGATCTGAAGAGCGTCCT<u>GGGTCAACTGGGCATCACTA</u>

<u>AGG</u>TCTTCAGCAATGGGGCTGACCTCTCCGGGGTCACAGAGGAGGCACCC

CTGAAGCTCTCCAAGGCCGTGCATAAGGCTGTGCTGACCATCGACGAGAA

AGGGACTGAAGCTGCTGGGGCCATGTTTTTAGAGGCCATACCCATGTCTA

TCCCCCCCGAGGTCAAGTTCAACAAACCCTTTGTCTTCTTAATGATTGAA

CAAAATACCAAGTCTCCCCTCTTCATGGGAAAAGTGGTGAATCCCACCCA

AAAATAA

Open reading frame of synthetic alpha-1-
antitrypsin (sAAT) (SEQ NO: 2):
ATGCCGTCTTCTGTCTCGTGGGGCATCCTCCTGCTGGCAGGCCTGTGCTG

CCTGGTCCCTGTCTCCCTGGCTGAAGATCCCCAGGGAGATGCTGCCCAG

AA<u>GACCGACACTAGTCATCAC</u>GATCAGGATCACCCAACCTTCAACAAGAT

CACCCCCAACCTGGCTGAGTTCGCCTTCAGCCTATACCGCCAGCTGGCAC

ACCAGTCCAACAGCACCAATATCTTCTTCTCCCCAGTGAGCATCGCTACA

GCCTTTGCAATGCTCTCCCTGGGGACCAAGGCTGACACTCACGATGAAAT

CCTGGAGGGCCTGAATTTCAACCTCACGGAGATTCCGGAGGCTCAGATCC

ATGAAGGCTTCCAGGAACTCCTCCGTACCCTCAACCAGCCAGACAGCCAG

CTCCAGCTGACCACCGGCAATGGCCTGTTCCTCAGCGAGGGCCTGAAGCT

-continued
AGTGGATAAGTTTTTGGAGGATGTTAAAAAGTTGTACCACTCAGAAGCCT
TCACTGTCAACTTCGGGGACACCGAAGAGGCCAAGAAACAGATCAACGAT
TACGTGGAGAAGGGTACTCAAGGGAAAATTGTGGATTTGGTCAAGGAGCT
TGACAGAGACACAGTTTTTGCTCTGGTGAATTACATCTTCTTTAAAGGCA
AATGGGAGAGACCCTTTGAAGTCAAGGACACCGAGGAAGAGGACTTCCAC
GTGGACCAGGTGACCACCGTGAAGGTGCCTATGATGAAAAGACTTGGTAT
GTTTAACATCCAGCACTGTAAGAAGCTGTCCAGCTGGGTTTTATTGATGA
AGTACCTGGGCAATGCCACCGCCATCTTCTTCCTGCCTGATGAGGGGAAA
CTACAGCACCTGGAAAATGAACTCACCCACGATATCATCACCAAGTTCCT
GGAAAATGAAGACAGAAGGAGCGCATCTCTGCACCTCCCCAAACTGTCCA
TTACTGGAACCTATGATCTGAAGAGCGTCCTGGGCCAGTTAGGTATTACA
AAGGTCTTCAGCAATGGGGCTGACCTCTCCGGGGTCACAGAGGAGGCACC
CCTGAAGCTCTCCAAGGCCGTGCATAAGGCTGTGCTGACCATCGACGAGA
AAGGGACTGAAGCTGCTGGGGCCATGTTTTTAGAGGCCATACCCATGTCT
ATCCCCCCCGAGGTCAAGTTCAACAAACCCTTTGTCTTCTTAATGATTGA
ACAAAATACCAAGTCTCCCCTCTTCATGGGAAAAGTGGTGAATCCCACCC
AAAAATAA

AGATCC = BamHI restriction site of the native
M-AAT has been deleted by introducing a silent
point mutation (bold) at nucleotide 75 of the
M-AAT cDNA transcript (G75A)
GACCGACACTAGTCATCAC = Target sequence of silencing
RNA/shRNA in M-AAT, resistant in sAAT because of
point mutations (bold)
Open reading frame of synthetic alpha-1-
antitrypsin (sAAT2) (SEQ ID NO: 3):
ATGCCGTCTTCTGTCTCGTGGGCATCCTCCTGCTGGCAGGCCTGTGCTG
CCTGGTCCCTGTCTCCCTGGCTGA AGATCCCCAGGGAGATGCTGCCCAG
AAGACAGATACATCCCACCATGATCAGGATCACCCAACCTTCAACAAGAT
CACCCCCAACCTGGCTGAGTTCGCCTTCAGCCTATACCGCCAGCTGGCAC
ACCAGTCCAACAGCACCAATATCTTCTTCTCCCCAGTGAGCATCGCTACA
GCCTTTGCAATGCTCTCCCTGGGGACCAAGGCTGACACTCACGATGAAAT
CCTGGAGGGCCTGAATTTCAACCTCACGGAGATTCCGGAGGCTCAGATCC
ATGAAGGCTTCCAGGAACTCCTCCGTACCCTCAACCAGCCAGACAGCCAG
CTCCAGCTGACCACCGGCAATGGCCTGTTCCTCAGCGAGGGCCTGAAGCT
AGTGGATAAGTTTTTGGAGGATGTTAAAAAGTTGTACCACTCAGAAGCCT
TCACTGTCAACTTCGGGGACACCGAAGAGGCCAAGAAACAGATCAACGAT
TACGTGGAGAAGGGTACTCAAGGGAAAATTGTGGATTTGGTCAAGGAGCT
TGACAGAGACACAGTTTTTGCTCTGGTGAATTACATCTTCTTTAAAGGCA
AATGGGAGAGACCCTTTGAAGTCAAGGACACCGAGGAAGAGGACTTCCAC
GTGGACCAGGTGACCACCGTGAAGGTGCCTATGATGAAGCGTTTAGGCAT
GTTTAACATCCAGCACTGTAAGAAGCTGTCCAGCTGGGTTTTATTGATGA
AGTACCTGGGCAATGCCACCGCCATCTTCTTCCTGCCTGATGAGGGGAAA
CTACAGCACCTGGAAAATGAACTCACCCACGATATCATCACCAAGTTCCT
GGAAAATGAAGACAGAAGGAGCGCATCTCTGCACCTCCCCAAACTGTCCA
TTACTGGAACCTATGATCTGAAGAGCGTCCTGGGCCAGTTAGGTATTACA
AAGGTCTTCAGCAATGGGGCTGACCTCTCCGGGGTCACAGAGGAGGCACC
CCTGAAGCTCTCCAAGGCCGTGCATAAGGCTGTGCTGACCATCGACGAGA
AAGGGACTGAAGCTGCTGGGGCCATGTTTTTAGAGGCCATACCCATGTCT
ATCCCCCCCGAGGTCAAGTTCAACAAACCCTTTGTCTTCTTAATGATTGA
ACAAAATACCAAGTCTCCCCTCTTCATGGGAAAAGTGGTGAATCCCACCC
AAAAATAA

AGATCC = the BamHI restriction site of the native
M-AAT has been deleted by introducing a point
mutation (bold)
GACCGACACTAGTCATCAC Target sequence of silencing
RNA/shRNA in M-AAT, resistant in sAAT2 because
of point mutations (bold)

Open reading frame of PiZZ alpha-1-antitrypsin
(Z-AAT) (SEQ ID NO: 4):
ATGCCGTCTTCTGTCTCGTGGGCATCCTCCTGCTGGCAGGCCTGTGCTG
CCTGGTCCCTGTCTCCCTGGCTGAGGATCCCCAGGGAGATGCTGCCCAGA
AGACAGATACATCCCACCATGATCAGGATCACCCAACCTTCAACAAGATC
ACCCCCAACCTGGCTGAGTTCGCCTTCAGCCTATACCGCCAGCTGGCACA
CCAGTCCAACAGCACCAATATCTTCTTCTCCCCAGTGAGCATCGCTACAG
CCTTTGCAATGCTCTCCCTGGGGACCAAGGCTGACACTCACGATGAAATC
CTGGAGGGCCTGAATTTCAACCTCACGGAGATTCCGGAGGCTCAGATCCA
TGAAGGCTTCCAGGAACTCCTCCGTACCCTCAACCAGCCAGACAGCCAGC
TCCAGCTGACCACCGGCAATGGCCTGTTCCTCAGCGAGGGCCTGAAGCTA
GTGGATAAATTTTTGGAGGATGTTAAAAAGTTGTACCACTCAGAAGCCTT
CACTGTCAACTTCGGGGACACCGAAGAGGCCAAGAAACAGATCAACGATT
ACGTGGAGAAGGGTACTCAAGGGAAAATTGTGGATTTGGTCAAGGAGCTT
GACAGAGACACAGTTTTTGCTCTGGTGAATTACATCTTCTTTAAAGGCAA
ATGGGAGAGACCCTTTGAAGTCAAGGACACCGAGGAAGAGGACTTCCACG
TGGACCAGGCGACCACCGTGAAGGTGCCTATGATGAAGCGTTTAGGCATG
TTTAACATCCAGCACTGTAAGAAGCTGTCCAGCTGGGTGCTGCTGATGAA
ATACCTGGGCAATGCCACCGCCATCTTCTTCCTGCCTGATGAGGGGAAAC
TACAGCACCTGGAAAATGAACTCACCCACGATATCATCACCAAGTTCCTG
GAAAATGAAGACAGAAGGTCTGCCAGCTTACATTTACCCAAACTGTCCAT
TACTGGAACCTATGATCTGAAGAGCGTCCTGGGTCAACTGGGCATCACTA
AGGTCTTCAGCAATGGGGCTGACCTCTCCGGGGTCACAGAGGAGGCACCC
CTGAAGCTCTCCAAGGCCGTGCATAAGGCTGTGCTGACCATCGACAAGAA
AGGGACTGAAGCTGCTGGGGCATGTTTTTAGAGGCCATACCCATGTCTA
TCCCCCCCGAGGTCAAGTTCAACAAACCCTTTGTCTTCTTAATGATTGAA
CAAAATACCAAGTCTCCCCTCTTCATGGGAAAAGTGGTGAATCCCACCCA
AAAATAA

A = point mutation in Z-AAT

Interfering RNA Sequences

Silencing RNA sequences are initially constructed as oligonucleotides that are annealed and cloned into shRNA expressing lentiviral transfer vector pLVTHM. The shRNA is designed as depicted below following the instructions from the original publication (Wiznerowicz and Trono, 2003). The original TTCAAGAGA-loop has been exchanged for an ACTCGAGA-loop.

MluI+linker: CGCGT CCCC
19-21 nt sense siRNA:
Loop: ACTCGAGA
19-21 nt anti-sense siRNA
Termination: TTTTT
Linker+ClaI: GGAA AT Specific sequences were constructed as follows.

shRNA ctrl1: 102-120 bp of ORF NM000295.4 (positive control shRNA published in Cruz et al., 2007)

```
sense siRNA:
                                    (SEQ ID NO: 5)
GACAGATACATCCCACCAT anti-sense siRNA:
                                    (SEQ ID NO: 6)
GACAGATACATCCCACCAT
```

Oligonucleotide for Annealing and Cloning:

```
oligo 1:
                                    (SEQ ID NO: 7)
5'- CGCGT CCCC GACAGATACATCCCACCAT ACTCGAGA
ATGGTGGGATGTATCTGTC TTTTT GGAA AT-3' oligo 2:
                                    (SEQ ID NO: 8)
5'- CGAT TTCC AAAAA GACAGATACATCCCACCAT TCTCGAGT
ATGGTGGGATGTATCTGTC GGGG A-3'
``` shRNA ctrl2: 732-752 bp of ORF NM000295.4 (positive control shRNA published in Li et al., 2011)

```
sense siRNA:
                                    (SEQ ID NO: 9)
GATGAAGCGTTTAGGCATG anti-sense siRNA:
                                    (SEQ ID NO: 10)
CATGCCTAAACGCTTCATC
```

Oligonucleotide for Annealing and Cloning:

```
Oligo 3:
                                    (SEQ ID NO: 11)
5'-CGCGT CCCC GATGAAGCGTTTAGGCATG ACTCGAGA
CATGCCTAAACGCTTCATC TTTTT GGAA AT-3'

Oligo 4:
                                    (SEQ ID NO: 12)
5'-CGAT TTCC AAAAA GATGAAGCGTTTAGGCATG TCTCGAGT
CATGCCTAAACGCTTCATC GGGG-3'
``` shRNA 1: 917 bp-937 bp of ORF NM000295.4

```
sense siRNA:
                                    (SEQ ID NO: 13)
GGTCTGCCAGCTTACATTTAC
The corresponding RNA sequence is provided as
SEQ ID NO: 39.

anti-sense siRNA:
                                    (SEQ ID NO: 14)
GTAAATGTAAGCTGGCAGACC
The corresponding RNA sequence is provided as
SEQ ID NO: 40.
```

Oligonucleotide for Annealing and Cloning:

```
Oligo 5:
                                    (SEQ ID NO: 15)
5'-CGCGT CCCC GGTCTGCCAGCTTACATTTAC ACTCGAGA
GTAAATGTAAGCTGGCAGACC TTTTT GGAA AT-3'

Oligo 6:
                                    (SEQ ID NO: 16)
5'-CGAT TTCC AAAAA GGTCTGCCAGCTTACATTTAC ACTCGAGA
GTAAATGTAAGCTGGCAGACC GGGG A-3'
``` shRNA 2 (prior art): 785-803 of ORF NM000295.4

```
sense siRNA:
                                    (SEQ ID NO: 17)
GGGTGCTGCTGATGAAATA
The corresponding RNA sequence is provided as
SEQ ID NO: 41.

anti-sense siRNA:
                                    (SEQ ID NO: 18)
TATTTCATCAGCAGCACCC
The corresponding RNA sequence is provided as
SEQ ID NO: 42.
```

Oligonucleotide for Annealing and Cloning:

```
Oligo 7:
                                    (SEQ ID NO: 19)
5'-CGCGT CCCC GGGTGCTGCTGATGAAATA ACTCGAGA
TATTTCATCAGCAGCACCC TTTTT GGAA AT-3'

Oligo 8:
                                    (SEQ ID NO: 20)
5'-CGAT TTCC AAAAA GGGTGCTGCTGATGAAATA ACTCGAGA
TATTTCATCAGCAGCACCC GGGG A-3'
``` shRNA3: 981-1001 of ORF NM000295.4

```
sense siRNA:
                                    (SEQ ID NO: 21)
GGGTCAACTGGGCATCACTAA
The corresponding RNA sequence is provided as
SEQ ID NO: 43.

anti-sense siRNA:
                                    (SEQ ID NO: 22)
TTAGTGATGCCCAGTTGACCC
The corresponding RNA sequence is provided as
SEQ ID NO: 44.
```

Oligonucleotide for Annealing and Cloning:

```
Oligo 9:
                                    (SEQ ID NO: 23)
5'-CGCGT CCCC GGGTCAACTGGGCATCACTAA ACTCGAGA
TTAGTGATGCCCAGTTGACCC TTTTT GGAA AT-3'

Oligo 10:
                                    (SEQ ID NO: 24)
5'-CGAT TTCC AAAAA GGGTCAACTGGGCATCACTAA ACTCGAGA
TTAGTGATGCCCAGTTGACCC GGGG-3'
```

Scramble shRNA:

```
sense siRNA:
                                (SEQ ID NO: 25)
GTGATCGCGTCAACGACTAGA anti-sense siRNA:
                                (SEQ ID NO: 26)
TCTAGTCGTTGACGCGATCAC
```

Oligonucleotide for Annealing and Cloning:

```
Oligo 11:
                                (SEQ ID NO: 27)
5'-CGCGT CCCC GTGATCGCGTCAACGACTAGA ACTCGAGA
TCTAGTCGTTGACGCGATCAC TTTTT GGAA AT-3'

Oligo 12:
                                (SEQ ID NO: 28)
5'-CGAT TTCC AAAAA GTGATCGCGTCAACGACTAGA ACTCGAGA
TCTAGTCGTTGACGCGATCAC GGGG A-3'
```

Primers qPCR Primers

| # | SEQ ID | Sequence | Description |
|---|---|---|---|
| 1 | SEQ ID NO: 29 | GGGTGCTGCTGATGAAATAC | Forward primer M-AAT |
| 2 | SEQ ID NO: 30 | TTAGTGATGCCCAGTTGACC | Reverse primer M-AAT |
| 3 | SEQ ID NO: 31 | GGGTTTTATTGATGAAGTACCTGG | Forward primer sAAT/sAAT2 |
| 4 | SEQ ID NO: 32 | TTTGTAATACCTAACTGGCCCA | Reverse primer sAAT/sAAT2 |
| 5 | SEQ ID NO: 33 | GTCACGACTGTGCAGCAGCGT | Forward primer MDH |
| 6 | SEQ ID NO: 34 | TGGGGTTCCAAACCAGATGTCCCTG | Reverse primer MDH |

Sequencing Primers

| # | SEQ ID | Sequence | Description |
|---|---|---|---|
| 100 | SEQ ID NO: 35 | TGATAGAGAAAAGTGAAAGTCGGGG | Forward sequencing primer on pLVTHM to check shRNA insertion of the cloning olignonucleotide |
| 101 | SEQ ID NO: 36 | GACCCAGTACAAGCAAAAAGCAGCA | reverse sequencing primer on pLVTHM to check shRNA insertion of the cloning olignonucleotide |

Sequence for Multiple shRNA

```
Sequence of insert for shRNA 1 x 3 (SEQ ID NO: 37):
GCGCG↓AATTCC↓GTACGCTGCAGTATTTAGCATGCCCCACCCATCTGCAAGG
CATTCTGGATAGTGTCAAAACAGCCGGAAATCAAGTCCGTTTATCTCAAACT
TTAGCATTTTGGGAATAAATGATATTTGCTATGCTGGTTAAATTAGATTTTAG
TTAAATTTCCTGCTGAAGCTCTAGTACGATAAGTAACTTGACCTAAGTGTAA
AGTTGAGATTTCCTTCAGGTTTATATAGCTTGTGCGCCGCCTGGGTACCTCC
GCGTCCCCGGTCTGCCAGCTTACATTTACACTCGAGAGTAAATGTAAGCTGGCAGACC
GGTCTTCACCTGAGGTTTTTGCGCGCGCCTAAGGACCAGCTTCTTTGGGAGAGA
ACAGACGCAGGGGCGGGAGGGAAAAAGGGAGAGGCAGACGTCACTTCCCCT
TGGCGGCTCTGGCAGCAGATTGGTCGGTTGAGTGGCAGAAAGGCAGACGGG
GACTGGGCAAGGCACTGTCGGTGACATCACGGACAGGGCGACTTCTATGTA
GATGAGGCAGCGCAGAGGCTGCTGCTTCGCCACTTGCTGCTTCACCACGAA
GGAGTTCCCGTGCCCTGGGAGCGGGTTCAGGACCGCTGATCGGAAGTGAGA
ATCCCAGCTGTGTGTCAGGGCTGGAAAGGGCTCGGGAGTGCGCGGGGCAAG
TGACCGTGTGTGTAAAGAGTGAGGCGTATGAGGCTGTGTCGGGGCAGAGGC
CCAAGATCTCCGCGTCCCCGGTCTGCCAGCTTACATTTACACTCGAGAGTAAATGTA
AGCTGGCAGACCGCAGTCTGGAGTTTCAAAAGTAGACTGG↓AATTCGCGC
```

Bold = promoter

Bold italique = promoter termination sequence

Italique = shRNA sense and anti-sense

-continued

Underlined = loop

↓ = restriction site

Sequence of insert for shRNA 1 x 3 containing sAAT2 (SEQ ID NO: 38):
GCGCG↓AATTCC↓GTACG**AGCTAGCTGCAGTAACGCCATTTTGCAAGGCATGG
AAAAATACCAAACCAAGAATAGAGAAGTTCAGATCAAGGGCGGGTACATGA
AAATAGCTAACGTTGGGCCAAACAGGATATCTGCGGTGAGCAGTTTCGGCCC
CGGCCCGGGGCCAAGAACAGATGGTCACCGCAGTTTCGGCCCCGGCCCGAG
GCCAAGAACAGATGGTCCCCAGATATGGCCCAACCCTCAGCAGTTTCTTAAG
ACCCATCAGATGTTTCCAGGCTCCCCAAGGACCTGAAATGACCCTGCGCCT
TATTTGAATTAACCAATCAGCCTGCTTCTCGCTTCTGTTCGCGCGCTTCTGCT
TCCCGAGCTCTATAAAAGAGCTCACAACCCCTCACTCGGCGCGCCAGTCCTC
CGA**CAGACTGAGTCGGCCGGTG*ATGCCGTCTTCTGTCTCGTGGGGCATCCTCCTGCT
GGCAGGCCTGTGCTGCCTGGTCCCTGTCTCCCTGGCTGAAGATCCCAGGGAGATGC
TGCCCAGAAGCAGATACATCCCACCATGATCAGGATCACCCAACCTTCAACAAGATCA
CCCCCAACCTGGCTGAGTTCGCCTTCAGCCTATACCGCCAGCTGGCACACCAGTCCAA
CAGCACCAATATCTTCTTCTCCCCAGTGAGCATCGCTACAGCCTTTGCAATGCTCTCC
TGGGGACCAAGGCTGACACTCACGATGAAATCCTGGAGGGCCTGAATTTCAACCTCAC
GGAGATTCCGGAGGCTCAGATCCATGAAGGCTTCCAGGAACTCCTCCGTACCCTCAAC
CAGCCAGACAGCCAGCTCCAGCTGACCACCGGCAATGGCCTGTTCCTCAGCGAGGGC
CTGAAGCTAGTGGATAAGTTTTTTGGAGGATGTTAAAAAGTTGTACCACTCAGAAGCCTT
CACTGTCAACTTCGGGGACACCGAAGAGGCCAAGAAACAGATCAACGATTACGTGGAG
AAGGGTACTCAAGGGAAATTGTGGATTTGGTCAAGGAGCTTGACAGAGACACAGTTTT
TGCTCTGGTGAATTACATCTTCTTTAAAGGCAAATGGGAGAGACCCTTTGAAGTCAAGG
ACACCGAGGAAGAGGACTTCCACGTGGACCAGGTGACCACCGTGAAGGTGCCTATGAT
GAAGCGTTTAGGCATGTTTAACATCCAGCACTGTAAGAAGCTGTCCAGCTGGGTTTTAT
TGATGAAGTACCTGGGCAATGCCACCGCCATCTTCTTCCTGCCTGATGAGGGGAAACT
ACAGCACCTGGAAAATGAACTCACCCACGATATCATCACCAAGTTCCTGGAAAATGAAG
ACAGAAGGAGCGCATCTCTGCACCTCCCCAAACTGTCCATTACTGGAACCTATGATCTG
AAGAGCGTCCTGGGCCAGTTAGGTATTACAAAGGTCTTCAGCAATGGGGCTGACCTCT
CCGGGGTCACAGAGGAGGCACCCCTGAAGCTCTCCAAGGCCGTGCATAAGGCTGTGC
TGACCATCGACGAGAAAGGGACTGAAGCTGCTGGGGCCATGTTTTTAGAGGCCATACC
CATGTCTATCCCCCCCGAGGTCAAGTTCAACAAACCCTTTGTCTTCTTAATGATTGAACA
AAATACCAAGTCTCCCCTCTTCATGGGAAAAGTGGTGAATCCCACCCAAAAA*TAAC↓GT*
ACGCTGCAGTATTTAGCATGCCCCACCCATCTGCAAGGCATTCTGGATAGTG
TCAAAACAGCCGGAAATCAAGTCCGTTTATCTCAAACTTTAGCATTTTGGGA
ATAAATGATATTTGCTATGCTGGTTAAATTAGATTTTAGTTAAATTTCCTGCT
GAAGCTCTAGTACGATAAGTAACTTGACCTAAGTGTAAAGTTGAGATTTCCT
TCAGGTTTATATAGCTTGTGCGCCGCCTGGGTACCT*CCGCGTCCCCGGTCTGC
CAGCTTACATTTAC*ACTCGAG*AGTAAATGTAAGCTGGCAGACCGGTCTTCACCTGAG
GTTTTTGCGCGCGCCTAAGGACCAGCTTCTTTGGGAGAGAACAGACGCAGGG
GCGGGAGGGAAAAAGGGAGAGGCAGACGTCACTTCCCCTTGGCGGCTCTGG
CAGCAGATTGGTCGGTTGAGTGGCAGAAAGGCAGACGGGGACTGGGCAAGG
CACTGTCGGTGACATCACGGACAGGGCGACTTCTATGTAGATGAGGCAGCG
CAGAGGCTGCTGCTTCGCCACTTGCTGCTTCACCACGAAGGAGTTCCCGTGC
CCTGGGAGCGGGTTCAGGACCGCTGATCGGAAGTGAGAATCCCAGCTGTGT
GTCAGGGCTGGAAAGGGCTCGGGAGTGCGCGGGGCAAGTGACCGTGTGTGT
AAAGAGTGAGGCGTATGAGGCTGTGTCGGGGCAGAGGCCCAAGATCTCCGC
GTCCCCGGTCTGCCAGCTTACATTTAC*ACTCGAG*AGTAAATGTAAGCTGGCAGACCGC
AGTCTGGA*TTTCAAAAGTAGACTG*G↓AATTCGCGC Bold = promoter (5'-3' order: SFFV, 7SK, U1)

Bold italique = promoter termination sequence

Bold italiaue underlined = stop codon of sAAT2

Italique = shRNA sense and anti-sense

Italique underlined = ORF of sAAT2

Underlined = loop

↓ = restriction site

The amino acid sequence of human alpha-1-antitrypsin protein is provided as SEQ ID NO: 45:

```
MPSSVSWGIL LLAGLCCLVP VSLAEDPQGD AAQKTDTSHH DQDHPTFNKI TPNLAEFAFS    60

LYRQLAHQSN STNIFFSPVS IATAFAMLSL GTKADTHDEI LEGLNFNLTE IPEAQIHEGF   120

QELLRTLNQP DSQLQLTTGN GLFLSEGLKL VDKFLEDVKK LYHSEAFTVN FGDTEEAKKQ   180

INDYVEKGTQ GKIVDLVKEL DRDTVFALVN YIFFKGKWER PFEVKDTEEE DFHVDQVTTV   240

KVPMMKRLGM FNIQHCKKLS SWVLLMKYLG NATAIFFLPD EGKLQHLENE LTHDIITKFL   300
```

-continued

ENEDRRSASL HLPKLSITGT YDLKSVLGQL GITKVFSNGA DLSGVTEEAP LKLSKAVHKA 360

VLTIDEKGTE AAGAMFLEAI PMSIPPEVKF NKPFVFLMIE QNTKSPLFMG KVVNPTQK

Positions 5281-5760 of pLVTHM.shRNA1 is disclosed in FIG. 2 and included in the sequence listing as SEQ ID NO: 46.

ABBREVIATIONS AND DEFINITIONS

The abbreviation "AAT" means alpha-1-antitrypsin protein. Human AAT protein is the gene product of the gene SERPINAL GenBank accession number NM_000295. It has a wild-type sequence as disclosed in the GenPept database accession number NP_000286. The gene product is a 418 amino acid precursor protein with an amino acid sequence according to SEQ ID NO: 45, comprising a 24 amino acid signal peptide. The mature protein comprises amino acid residues 25-418 of SEQ ID NO: 45. Allelic variants of wild-type AAT that do not confer AAT deficiency are known and include e.g. variants called M1, M1V, M1A, M2, M3, M4, B(Alhambra), F, P(St. Albans), and Christchurch, see e.g. the Online Mendelian Inheritance in Man database, available online at www.omim org, entry 107400. Allelic variants of human AAT that do not confer AAT deficiency when present in a human subject are denoted "functional AAT" in the context of this description.

DETAILED DESCRIPTION

In a first aspect, the present invention relates to ribonucleic acid molecules useful as small interfering RNA molecules (siRNAs). Such RNA molecules are useful in therapeutic methods using RNA interference to target and regulate the expression of AAT variants causing or contributing to AAT deficiency. The ribonucleic acid molecules useful as siRNAs according to the invention are typically 19, 20, or 21 nucleotides in length and comprise a sequence selected from SEQ ID NO: 39, 40, 43 and 44.

The siRNA molecules may be chemically modified in order to improve their therapeutic effect in vivo, i.a. by overcoming immune responses and elimination by endonucleases. Such chemical modifications may be modifications in the phosphodiester backbone, such as by incorporation of phosphorothioate, boranophosphate, or methylphosphonate; or in the sugar backbone such as at the 2'-position of the ribose unit, such as by substitution of the 2'-OH group for —O—$CH_3$, —$CH_2CH_2OCH_3$, or —F or by incorporation of 2-thiouridine, 5-methylcytidine or pseudouridine.

In a further aspect, the present invention relates to ribonucleic acid molecules useful as short hairpin RNA molecules (shRNAs). Such RNA molecules are useful in therapeutic methods using RNA interference to target and regulate the expression of AAT variants causing or contributing to AAT deficiency. The ribonucleic acid molecules useful as shRNAs according to the invention typically consists of 40-100 nucleotides, and comprises two sequences separated by a loop region of 4-10 nucleotides, wherein the two sequences are selected from the sequence pairs: SEQ ID NO: 39 and 40; and SEQ ID NO: 43 and 44.

The invention also relates to DNA molecules useful in producing shRNAs in vivo or ex vivo. Such DNA molecules comprise at least one nucleotide sequence complementary to at least one shRNA molecule as described above. A DNA molecule suitable for use in producing shRNAs according to the invention may also comprise two or three, or more, sequences complementary to shRNAs according to the invention. The sequences comprised in the DNA molecule may be complementary to one and the same, or different, shRNAs.

In a preferred embodiment, any nucleotide sequence complementary to a shRNA molecule according to the invention is operably linked to a RNA polymerase promoter sequence. Each nucleotide sequence complementary to a shRNA molecule according to the invention could be operably linked to a separate RNA polymerase promoter sequence. Alternatively, more than one nucleotide sequence complementary to a shRNA molecule according to the invention are operably linked to a single RNA polymerase promoter sequence. In one embodiment, all nucleotide sequences complementary to shRNA molecules according to the invention are operably linked to a single RNA polymerase promoter sequence.

In one embodiment, the RNA polymerase promoter sequence or RNA polymerase promoter sequences are selected from the group consisting of RNA polymerase promoters H1, 7SK, and U1.

In one aspect, the invention relates to a DNA molecule comprising a sequence encoding a functional human alpha-1-antitrypsin and having at least 90% identity to SEQ ID NO: 1, wherein said sequence comprises a plurality of point mutations in relation to SEQ ID NO: 1, said point mutations rendering an RNA-transcript of said DNA molecule resistant to gene silencing by RNA interference mediated by an RNA molecule according to the above mentioned aspects of the invention.

Preferred point mutations and their effect on resistance to gene silencing by RNA interference are disclosed in Table 1.

TABLE 1

| Mutations in synthetic alpha-1-antitrypsin | | | |
|---|---|---|---|
| Location of silent point mutation on the M-AAT cDNA transcript | sAAT | sAAT2 | Resistance against shRNA |
| G75A | Yes | Yes | No, only deletes BamHI site |
| A105C | Yes | No | shRNA ctrl 1 |
| T108C | Yes | No | |
| 111T | Yes | No | |
| 112A | Yes | No | |
| 113G | Yes | No | |
| 114T | Yes | No | |
| C117T | Yes | No | |
| T120C | Yes | No | |
| G738A | Yes | No | shRNA ctrl 2 |
| C739A | Yes | No | |
| T741A | Yes | No | |
| T742C | Yes | No | |
| A744T | Yes | No | |
| C747T | Yes | No | |
| G789T | Yes | Yes | shRNA2 (prior art) |
| C790T | Yes | Yes | |
| G792A | Yes | Yes | |
| C793T | Yes | Yes | |
| A801G | Yes | Yes | |
| T919A | Yes | Yes | shRNA1 |
| C920G | Yes | Yes | |
| T921C | Yes | Yes | |
| C924A | Yes | Yes | |

TABLE 1-continued

Mutations in synthetic alpha-1-antitrypsin

Location of silent point
mutation on the M-
AAT cDNA transcript | sAAT | sAAT2 | Resistance against shRNA
--- | --- | --- | ---
A925T | Yes | Yes |
G926C | Yes | Yes |
C927T | Yes | Yes |
T928C | Yes | Yes |
A930G | Yes | Yes |
T933C | Yes | Yes |
T934C | Yes | Yes |
A936C | Yes | Yes |
T984C | Yes | Yes | shRNA3
A987G | Yes | Yes |
C988T | Yes | Yes |
G990A | Yes | Yes |
C993T | Yes | Yes |
C996T | Yes | Yes |
T999A | Yes | Yes |

In one embodiment, the DNA molecule comprising a sequence encoding a functional human alpha-1-antitrypsin also comprises the G75A mutation in relation to SEQ ID NO: 1, which mutation renders a BamH1 site in SEQ ID NO: 1 inoperative.

In a preferred embodiment of the above aspect, the functional human alpha-1-antitrypsin encoded by the DNA molecule comprises or consists of an amino acid sequence according to positions 25-418 of SEQ ID NO: 45. In one embodiment, the functional human alpha-1-antitrypsin encoded by the DNA molecule comprises or consists of an amino acid sequence according to SEQ ID NO: 45.

In one aspect, the invention relates to an RNA molecule useful as a synthetic retroviral gene for use in a gene delivery based on a retrovirus. Such RNA molecules should comprise sequences that, when used in an appropriate retroviral vector, serves to express the shRNA molecules according to the above mentioned aspects of the invention and/or mRNA for functional alpha-1-antitrypsin, that is resistant to gene silencing by said shRNA molecules or the siRNA molecules according to the invention. Such RNA molecules typically comprise a nucleotide sequence complementary to DNA molecules according to the above mentioned aspects.

In one aspect, the invention relates to virus particles comprising a recombinant viral genome, wherein said genome comprises a DNA molecule comprising the sequence of a DNA molecule according to the above aspects, encoding shRNA molecules and/or functional human alpha-1-antitrypsin resistant to gene silencing by said shRNA molecules or the siRNA molecules according to the invention.

In one aspect, the invention relates to virus particles comprising a recombinant viral genome, wherein said genome comprises an RNA molecule comprising the sequence of an RNA molecule according to the above aspects, encoding shRNA molecules and/or functional human alpha-1-antitrypsin resistant to gene silencing by said shRNA molecules or the siRNA molecules according to the invention. Such virus particles are useful as viral delivery vehicles of the nucleic acid materials according to the invention.

In one aspect, the invention relates to non-viral delivery vehicles for nucleic acid material to a human cell in vivo, wherein said vehicle comprises a DNA molecule according to the above aspects, encoding shRNA molecules and/or functional human alpha-1-antitrypsin resistant to gene silencing by said shRNA molecules or the siRNA molecules according to the invention. Alternatively or additionally, the non-viral delivery vehicle may comprise an RNA molecule according to the above aspects, encoding shRNA molecules and/or functional human alpha-1-antitrypsin resistant to gene silencing by said shRNA molecules or the siRNA molecules according to the invention.

The non-viral delivery vehicle may be selected from the group plasmid DNA, lipid-based vectors, and polymeric vectors.

In a further aspect, the invention relates to a method for treatment of a subject comprising administering a nucleic acid molecule according to the invention to a subject in need thereof. In embodiments of this aspect, the nucleic acid material is administered by the viral or non-viral delivery vehicles discussed above. The non-viral delivery vehicles may be administered by e.g. gene gun/ballistic DNA, electroporation, sonoporation, hydroporation, magnetofection, or needle injection.

In a preferred embodiment, the condition to be treated by the method of treatment is alpha-1-antitrypsin deficiency. In one embodiment, the subject to be treated carries the G342K mutation in a gene encoding alpha-1-antitrypsin, and may be homozygous or heterozygous for this mutation. Thus, in one aspect the method further comprises analysis of the genome of a potential subject to be treated with respect to mutation status of a gene encoding alpha-1-antitrypsin and determination of whether the subject carries the G342K mutation in a gene encoding alpha-1-antitrypsin. A subject carrying the G342K mutation in at least one allele is particularly amenable to treatment with the method according to the invention.

In one embodiment, the alpha-1-antitrypsin deficiency manifests as liver cirrhosis, pulmonary emphysema, necrotising panniculitis, systemic vasculitis, aneurysms (such as intracranial aneurysms), fibromuscular dysplasia, bleeding disorders, anterior uveitis, systemic necrotizing vasculitis or Wegener granulomatosis.

In one aspect, the invention relates to the nucleic acids, and viral and non-viral delivery vehicles according to the invention for use in methods for treatment of the human or animal body, preferably the human body, even more preferably in the methods of treatment according to the above mentioned aspects of the invention.

In one aspect, the invention relates to the use of the nucleic acids, and viral and non-viral delivery vehicles according to the invention for use in the manufacture of a pharmaceutical composition for use in methods for treatment of the human or animal body, preferably the human body, even more preferably in the methods of treatment according to the above mentioned aspects of the invention.

The various aspects and embodiments of the invention are further explained and described below. Detailed background knowledge and information relevant to the invention are also discussed in the background section of the present disclosure and in the references discussed throughout this disclosure, which are all explicitly incorporated by reference herein.

Elimination of the Misfolded AAT Protein:

The technique of RNA interference was used to decrease the synthesis of endogenous and potentially hazardous AAT. RNA interference was mediated by short-hairpin RNA, although the functionality of the specific RNA sequences used for knockdown of the endogenous AAT gene are not limited to shRNA molecules but can also be exploited to other RNA interfering molecules such as siRNA and miRNA.

Figure 4:
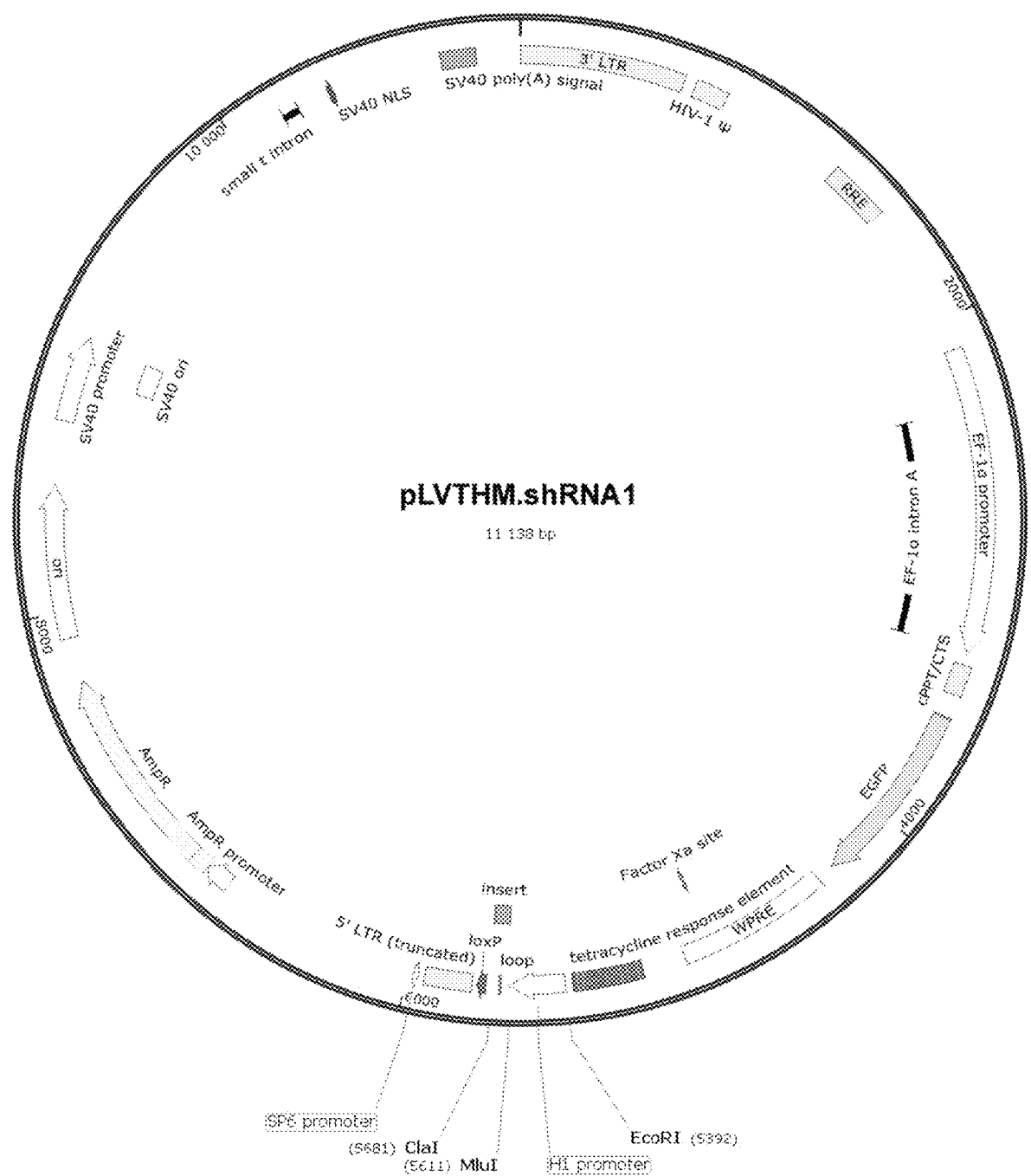
FIG. 4: pLVTHM.shRNA1: Paired shRNA oligonucleotides were annealed and cloned into pLVTHM by MluI and ClaI. The H1 shRNA promoter regulating the RNA Polymerase III is located upstream of the shRNA insertion site. eGFP is co-expressed under the control of an EF-1α promoter to easily identify transduced cells. Lentiviral production using the lentiviral transfer vector pLVTHM.shRNA1/2/3 along with structural lentiviral plasmids yielded LV-shRNA1, LV-shRNA2 or LV-shRNA3, respectively.
Figure 5:
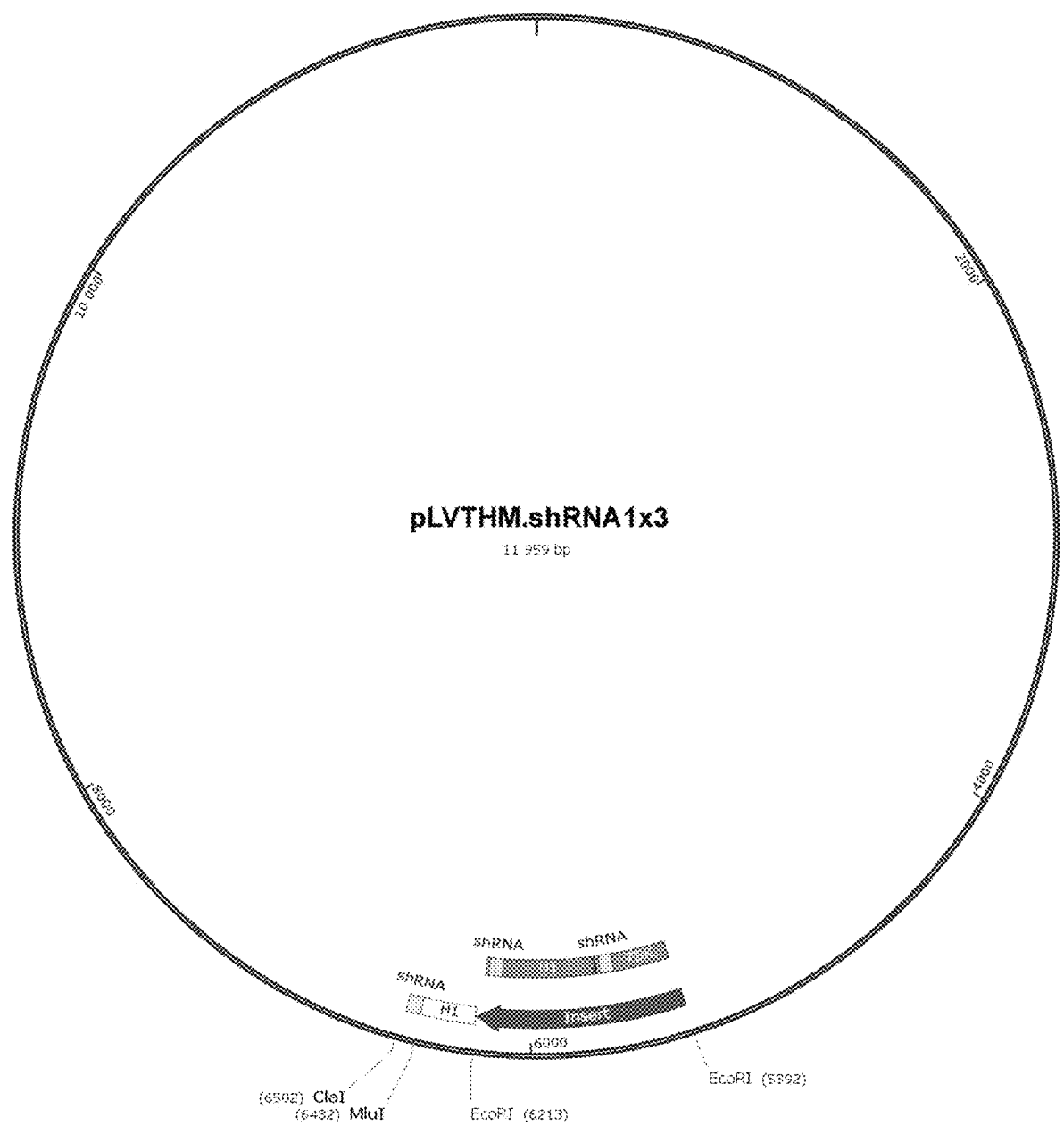
FIG. 5: pLVTHM.shRNA1x3: A newly designed insert containing two shRNAs each individually under the control of one RNA polymerase promoter (7SK and U1) were synthesized and cloned into the EcoRI cloning site of pLVTHM.shRNA1 to generate pLVTHM.shRNA1x3. pLVTHM.shRNA1x3 allowed expression of multiple shRNAs from different promoters (multicistronic expression), thereby maximizing knock-down by RNA interference and minimizing the risk of recombinational events leading to loss of shRNA activity. For reasons of clarity, only shRNA promoters and shRNA sequences are shown in this figure. All other genetic elements of pLVTHM are still integrated in the pLVTHM.shRNA1x3 transfer vector as depicted in FIG. 4. Lentiviral production using the lentiviral transfer vector pLVTHM.shRNA1x3 along with structural lentiviral plasmids yielded LV-shRNA1x3.
Figure 6:
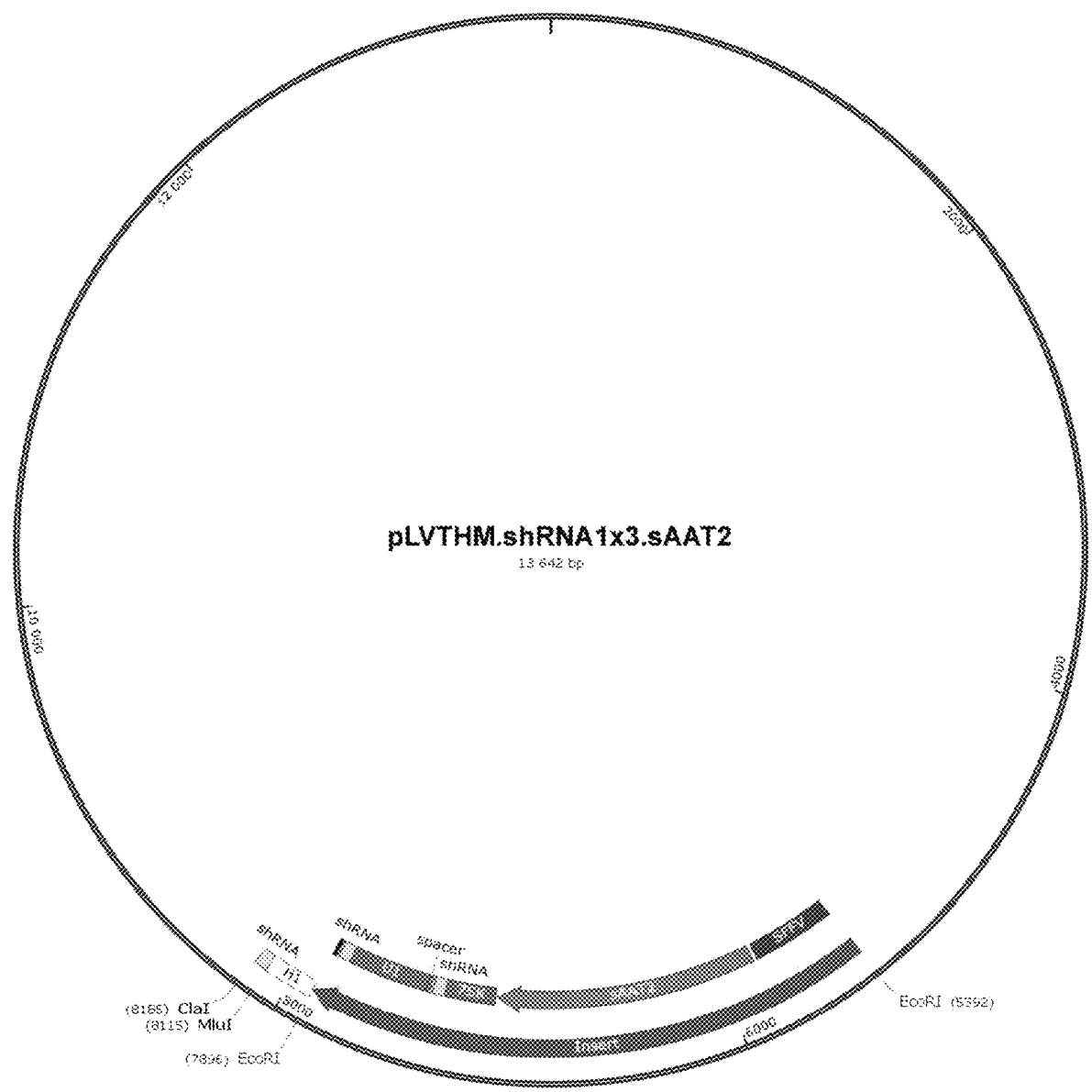
FIG. 6: A newly designed insert containing sAAT2 and two shRNAs, each individually under the control of the RNA polymerase promoter 7SK and U1, were synthesized and cloned into the EcoRI cloning site of pLVTHM.shRNA1 to generate pLVTHM.shRNA1x3.sAAT2. pLVTHM.shRNA1x3.sAAT2 allowed expression of multiple shRNAs thereby maximizing knock-down by RNA interference and minimizing the risk of recombinational events leading to loss of shRNA activity. Simultaneously, one recombinant protein sAAT2 was expressed along with shRNAs to replace the knocked-down and defective M-AAT/Z-AAT. For reasons of clarity, only the SFFV, promoter, the sAAT2 transgene, the shRNA promoters and shRNA sequences are shown in this figure. All other genetic elements of pLVTHM are still integrated in the pLVTHM.shRNA1x3.sAAT2 transfer vector as depicted in FIG. 4. Lentiviral production using the lentiviral transfer vector pLVTHM.shRNA1x3.sAAT2 along with structural lentiviral plasmids yielded LV-shRNA1sAAT2.

In the experiments described in this invention, shRNA expression was mediated by lentiviral vectors that had integrated into the cell genome. Expressional activity was controlled by the RNA polymerase III promoter H1, the RNA polymerase promoter III 7SK, or the RNA polymerase II promoter U1. Expression of shRNA was either unicistronic from one H1 promoter, or multicistronic from multiple RNA polymerase promoters. Unicistronic expression was accomplished by cloning of the shRNA oligonucleotides (SEQ ID NO: 7, SEQ ID NO: 8, SEQ ID NO: 11, SEQ ID NO: 12, SEQ ID NO: 15, SEQ ID NO: 16, SEQ ID NO: 19, SEQ ID NO: 20, SEQ ID NO: 21, SEQ ID NO: 22, scramble SEQ ID NO: 25, scramble SEQ ID NO: 26) into the lentiviral transfer vector pLVTHM using the MluI and ClaI restriction sites as suggested by the original work (FIG. 2, FIG. 4). Multicistronic expression of several shRNAs was accomplished by cloning of the respective promoter sequences combined with downstream shRNA oligonucleotides into the EcoRI cloning site upstream of the H1 promoter of the original pLVTHM transfer vector (FIG. 5). The synthesis and cloning of oligonucleotides for multicistronic shRNA expression was performed by commercially available services and sub-cloned into a cloning vector by commercially available cloning services. In case of pLVTHM.shRNA1x3 the synthesized cloning oligonucleotide (SEQ ID NO: 37) consisted of restriction sites, promoter sequences, promoter termination sequences, shRNA sense and loop and anti-sense sequences. In case of pLVTHM.shRNA1x3.sAAT2, the synthesized oligonucleotide included also the SFFV promoter sequence and the sAAT2 recombinant protein sequence (SEQ ID NO: 38).

HEK293T producer cell lines were transfected with lentiviral vectors along with structural plasmids psPAX2 and pMD2.G in order to produce viral particles. Viral particles were used to infect target cells, to release and to integrate the genetic information into the cell genome provided by the transfer vector. Normally, the gene sequence inserted into the target cell genome upon target cell transduction is framed by the 5'LTR and the self-inactivating of the transfer vector. In these experiments, variants of pLVTHM were used to integrate single or multiple shRNAs, combined with recombinant protein (sAAT2) or not.

The insertion order of the following genetic elements is presented in a 5'-3' directional manner.

(i) For the viral particles produced with transfer vector with unicistronic (expression of one single shRNA from one promoter) shRNA expression, the 5'LTR was integrated followed by the psi-packaging signal, the Rev responsive element (RRE), the EF-1α promoter, the (cPPT), the eGFP coding sequence, the Woodchuck Hepatitis Virus (WHP) Posttranscriptional Regulatory Element (WPRE), the tetracycline responsive element (TetO), the EcoRI cloning site, the H1 promoter, the MluI cloning site, the cloned shRNA oligonucleotide, the ClaI restriction site and the self-inactivating 3' LTR (FIG. 4).

(ii) For lentiviral particles produced with a transfer vector with multicistronic shRNA expression (multiple shRNA are expressed from individual promoters H1, 7SK or U1), 5'LTR was integrated followed by the psi-packaging signal, the Rev responsive element (RRE), the EF-1α promoter, the (cPPT), the eGFP coding sequence, the Woodchuck Hepatitis Virus (WHP) Posttranscriptional Regulatory Element (WPRE), the tetracycline responsive element (TetO), the 5' EcoRI restriction site (generated by splitting the original EcoRI site by the cloning procedure), the BsiWI site, the 7SK promoter sequence, the shRNA sense-loop-antisense sequence, a spacer, the 7SK termination sequence, a second spacer, the U1 promoter sequence, a second shRNA sense-loop-antisense sequence, a spacer, the U1 termination sequence, the 3' EcoRI restriction site, the H1 promoter, the MluI cloning site, the cloned shRNA oligonucleotide, the ClaI restriction site and the self-inactivating 3'LTR (FIG. 5).

(iii) For the lentiviral particles produced with a transfer vector with combined expression ore recombinant protein and multicistronic shRNA expression, 5'LTR was integrated followed by the psi-packaging signal, the Rev responsive element (RRE), the EF-1α promoter, the (cPPT), the eGFP coding sequence, the Woodchuck Hepatitis Virus (WHP) Posttranscriptional Regulatory Element (WPRE), the tetracycline responsive element (TetO), the 5' EcoRI restriction site (generated by splitting the original EcoRI site by the cloning procedure), the 5' BsiWI site (added in during the oligonucleotide synthesis step), the SFFV promoter, the sAAT2 ORF, the 7SK promoter sequence, the shRNA sense-loop-antisense sequence, a spacer, the 7SK termination sequence, a second spacer, the U1 promoter sequence, a second shRNA sense-loop-antisense sequence, a spacer, the U1 termination sequence, the 3' EcoRI restriction site, the H1 promoter, the MluI cloning site, the cloned shRNA oligonucleotide, the ClaI restriction site and the self-inactivating 3'LTR.

It is essential to note that in the mentioned multicistronic transfer vectors, the shRNA sequences are interchangeable, i.e. in one vector shRNA expression is not confined to one type of shRNA (e.g. shRNA1). Each promoter individually controls the expression of its succeeding shRNA, meaning that in the presence of three different promoters there is the possibility to express two different shRNA (shRNA1 plus shRNA 3) using one single lentiviral vector.

Some publications suggest that using one and the same RNA polymerase promoter in multicistronic shRNA expression has no influence on the efficiency of shRNA expression (Stove et al., 2006). However, it has been demonstrated that recombinational events may occur between homology sequences when using promoters of the same type (ter Brake O et al., 2008). Therefore, distinct RNA polymerase promoters were chosen to mediate individual shRNA expression from one lentiviral vector to achieve highly efficient knock-down of the target gene. In this invention these were the 7SK promoter, the U1 promoter and the H1 promoter already integrated into the pLVTHM transfer vector.

The interfering RNA sequences were designed by the means of online RNAi design web tools made available by Invitrogen, Thermo Scientific and Invivogen. In this specific application, the described experiments implement the calculated RNA sequences as short-hairpin RNAs expressed with the help of RNA polymerase promoters delivered to target cells by the means of lentiviral delivery. It has to be emphasized that the calculated RNA sequences are not limited to the use as solely shRNAs, but can also be introduced into target cells and tissue by other viral or non-viral delivery systems which use miRNA and siRNA as expression modulators instead of shRNAs. The experiments described in this application are used as examples of RNAi with these specific RNA sequences.

Three positive control shRNA (shRNA ctrl 1, shRNA ctrl 2 and shRNA2) that had previously published were taken along with experiments. The target sequence of shRNA ctrl 1 is located at 102-120 bp of the ORF of NM_000295.4 (sense strand SEQ ID NO: 5; anti-sense strand SEQ ID NO:

6). The sequences were integrated into the sense and antisense cloning oligonucleotides SEQ ID NO: 7 and SEQ ID NO: 8. The target sequence of shRNA ctrl 2 is located at 732-752 bp of ORF of NM_000295.4 (sense strand SEQ ID NO: 9, anti-sense SEQ ID NO: 10). The matching cloning oligonucleotides were SEQ ID NO: 11 and SEQ ID NO: 12. The target sequences for shRNA2 were 785-803 bp of the ORF of NM_000295.4 (sense SEQ ID NO: 17, anti-sense SEQ ID NO: 18; sense oligonucleotide SEQ ID NO: 19 and antisense SEQ ID NO: 20). The sense and anti-sense oligonucleotides were annealed and cloned into the linearized pLVTHM lentiviral transfer vector.

The target sequences were for shRNA 1 917-937 bp of the ORF of NM_000295.4 (sense SEQ ID NO: 13, anti-sense SEQ ID NO: 14; sense oligonucleotide SEQ ID NO:15 and antisense SEQ ID NO: 16), and for sRNA 3 981-1001 bp of the ORF of NM_000295.4 (sense SEQ ID NO: 21, anti-sense SEQ ID NO: 22; sense oligonucleotide SEQ ID NO: 23 and antisense SEQ ID NO: 24). The sense and anti-sense oligonucleotides were annealed and cloned into the linearized pLVTHM lentiviral transfer vector. In the original pLVTHM lentiviral transfer vector, shRNA expression is mediated by the H1 promoter in a unicistronic manner. In the newly designed multicistronic versions of pLVTHM, shRNAs were expressed each individually controlled by one specific RNA polymerase promoter. Theoretically, one could randomly combine any shRNA in these vectors to create the most the efficient RNAi knock-down tool.

Rescue Expression of Synthetic AAT (sAAT/sAAT2)

In this invention, synthetic AAT is expressed by lentiviral vectors to replace the AAT that has been subject to RNA interference mediated by shRNA and to replace defective AAT. However, expression of the synthetic proteins described in this invention is not limited to lentiviral vectors, but can be extended to all kinds of viral and non-viral expression systems. Expression of sAAT and sAAT2 does not have to be combined with the expression of shRNAs, but can be stand alone as well.

sAAT/sAAT2 were cloned into the lentiviral transfer vector pSFFV.IRES.dTomato in which shRNA and rescue expression of the recombinant sAAT/sAAT2 was not combined. When using this approach, target cells were first transduced with LV-shRNA introducing the essential elements for knock-down of endogenous M-AAT/Z-AAT. Subsequently, target cells were transduced with LV-sAAT to ensure replacement expression of sAAT. Double transduction of target cells is possible and this approach has been widely used to transduce cells with several recombinant proteins at a time. However, risks are lower transduction efficiency and increased cell toxicity.

The expression of the recombinant protein sAAT and sAAT2 was controlled by the spleen focus forming virus (SFFV) promoter. The SFFV promoter was chosen because of its strong eukaryotic expression ability in various cell types and its safety characteristics. Numerous publications use the SFFV promoter to mediate highly efficient expression of recombinant proteins. The high expressional activity of SSFV may be a crucial prerequisite to overcome the serum level therapeutic threshold of AAT needed to treat AATD related lung emphysema. Other eukaryotic promoters, including hepatocyte derived Albumin promoter may not exhibit expressional activity high enough to secure AAT serum levels above the 11 µM threshold.

The synthetic sAAT and sAAT2 were designed with integrated point mutations compared to wild-type NM_000295.4 to (i) eliminate one BamHI restriction site at position 75 nt of the ORF of NM_000295.4 and (ii) to render the synthetic AAT gene sequence and mRNA resistant against the introduced interfering RNAs. By deletion of the BamHI restriction site the recombinant gene sequence will be flanked by BamHI restriction sites to facilitate restriction analysis patterns and to be able easily excise the whole gene in subsequent cloning strategies. However, the BamHI site is not essential for the invention and does not have implications on expression levels of sAAT/sAAT2 or shRNA knockdown ability.

In order to test the application and to compare with suitable positive controls one designed sAAT. sAAT does contain the silent point mutations making it resistant to all shRNA described above including the control shRNAs. In contrast, sAAT2 does not contain the silent mutations within the target sequences of shRNA ctrl 1 and shRNA ctrl 2. Thus, sAAT2 equals the naturally occurring M-AAT to higher extent which may have beneficial effects on expression levels and sustainability in the blood stream.

The target sequences of all shRNAs are presented in the sequence of wild-type M-AAT (NM_000295.4 SEQ ID NO: 1). Z-AAT differs from M-AAT by only one amino acid exchange which is located outside the sequences targeted by the shRNAs. Therefore, in the context of RNA interference mediated by these specific shRNAs, Z-AAT can be considered as being equivalent to M-AAT in this application. Although shRNAs do not target sAAT or sAAT2, the sequences in sAAT/sAAT2 corresponding to the targeted sequences in M-AAT/Z-AAT are highlighted in the sAAT/sAAT2 genes (SEQ ID NO: 2 and SEQ ID NO: 3) for reasons of clarification.

Primers for Wild Type AAT and Synthetic sAAT

Knock-down efficiency and rescue expression of sAAT/sAAT2 was monitored mainly by the means of quantitative PCR. In order to distinguish M-AAT/Z-AAT from sAAT/sAAT2, primers were designed to specifically recognize and amplify either M-AAT/Z-AAT or sAAT/sAAT2. In the synthetic version of AAT, silent point mutations were integrated at short-stretched specific locations to render the sAAT/sAAT2 immune against shRNAs. These modified genetic stretches were approximately 19-21 bp long, representing the ideal template for sAAT/sAAT2 specific qPCR primers.

For M-AAT/Z-AAT detection, the primer pair 1/2 used the forward (sense) target sequence of shRNA 2 (prior art) (785-803 bp) of M-AAT/Z-AAT as a forward qPCR primer template (SEQ ID NO: 29) and the reverse (anti-sense) target sequence of shRNA 3 (981-1001 bp) of M-AAT/Z-AAT as a reverse qPCR primer template (SEQ ID NO: 30).

For detection of sAAT/sAAT2, the primer pair 3/4 used the forward (sense) sequence of sAAT/sAAT2 replacing the target sequence of shRNA 2 (prior art) (785-803 bp) as a forward qPCR primer template (SEQ ID NO: 31) and the reverse sequence (anti-sense) of sAAT/sAAT2 replacing the reverse target sequence of shRNA 3 (981-1001 bp) as a reverse qPCR primer template (SEQ ID NO: 32). The primer pair exclusively detected DNA template from sAAT/sAAT2, resulting in the amplification of sAAT/sAAT2 fragments only. The discrimination against M-AAT/Z-AAT made it a valuable asset in specifically detecting synthetic AAT.

In the qPCR experiments, the malate dehydrogenase (MDH) gene was used as reference gene. The MDH specific primers (SEQ ID NO: 33 and SEQ ID NO: 34) were previously published in Riedel et al (2013).

Sequencing Primers

In order to detect the insertion of the cloning oligonucleotides in pLVTHM.shRNA1, pLVTHM.shRNA1x3 or pLVTHM.shRNA1x3.sAAT2, sequencing primers were design to amplify the nucleotide template located between the EcoRI cloning site located upstream of the and the ClaI site at the 3' end of the insertion site. This allowed full length sequence analysis of short shRNA only insertions as well as extenden sAAT-multiple shRNA insertions.

Methods

The following section describes methods useful in working the present invention. The methods are exemplary and illustrative, and shall not be considered as limiting the scope of the invention, which is that of the appended claims. The skilled person will appreciate that materials and methods that are common general knowledge in the art may also be used to put the present invention into practice. Such materials and methods are disclosed i.a. in Molecular Cloning: A Laboratory Manual (Sambrook et al., CSH Laboratory Press, NY, USA), Gene Biotechnology (Wu et al., CRC Press) and Bioanalytik, (Lottspeich, 1998, Spektrum Akademischer Verlag, Heidelberg).

Cell Culture Maintenance

Lenti-X™ 293T Cell Line (ClonTech #632180) was used for lentiviral production. The cells cultures were thawed according to manufacturer's instructions and maintained in T-175 cm$^2$ flasks containing Dulbecco's Modified Earl's Medium (DMEM; Lonza #BE12-614F) supplemented with 100E/100E Penicillin/Streptomycin (PenStrep; Lonza #17-602E), 2 mM L-Glutamine (Lonza #17-605E), 1 mM sodium pyruvate (Lonza #BE13-115E) and 10% HyClone™ Fetal Bovine Serum (FBS; GE #SV30160.03) if not stated otherwise.

HepG2 cells (Sigma-Aldrich #85011430-1VL) were used for transduction experiments. The cells were thawed according to the manufacturer's instructions and maintained in T-175 cm$^2$ flasks containing Roswell Park Memorial Institute medium (RPMI; Lonza #BE12-115F) supplemented with Penicillin/Streptomycin and 10% FBS if not stated otherwise.

For sub-cultivation, cell cultures were washed with Dulbecco's phosphate buffered saline (DPBS, Lonza #17-512F), trypsinised with HyClone Trypsin 0.05% (GE SH40003.01), resuspended in medium and transferred into new cell culture flasks.

Generation of Lentiviral Transfer Plasmids

Cloning of Single shRNA into pLVTHM siRNA/shRNA sense nucleotide sequences were designed by the web based RNAi software Block-iT™ RNAi designer by Invitrogen, GeneAssist™ Custom siRNA Builder by Thermo Scientific and siRNA Wizard™ by Invivogen. The sense and anti-sense oligonucleotides were designed as described by Wiznerowicz and Trono. The paired sense and anti-sense oligonucleotides contained an overhang 5'-MluI restriction site, followed by a CCCC linker element, the 19-21 nucleotide (nt) sense siRNA sequence, the ACTCGAGA hairpin loop, the 19-21 nt anti-sense siRNA sequence, the TTTTT termination signal, a GGAA linker and an overhang 3'-ClaI restriction site. The overhang restriction sites were implemented to easily insert the oligonucleotide into the lentiviral transfer vector linearised with ClaI and MluI.

Sense and anti-sense oligonucleotides were acquired from Eurofins Genomics with high liquid pressure chromatography (HLPC)-purity and diluted to stock solutions with concentration around 2 μg/ml (~100 μM). 2 μg of sense and 2 μg anti-sense oligonucleotides of one oligonucleotide pair were transferred into a 1.5 ml centrifugation tube and diluted with 48 μl annealing buffer (10 mM Tris, 50 mM NaCl, 1 mM EDTA, pH 7.5-8.0). The oligo mixture was incubated at 95° C. and cooled down at RT for >45 min.

The annealed oligonucleotides were cloned into the pLVTHM (a gift from Didier Trono, Addgene plasmid #12247) shRNA expressing lentiviral transfer plasmid backbone using a standardized cloning protocol. In short, 2 μg of pLVTHM was digested with 1 μl/10 units MluI (New England Biolabs, NEB R0198S) and 2 μl/20 units ClaI (NEB R0197S) in NEB buffer 3.1 at 37° C. for 10 minutes. The restriction enzymes were heat-inactivated at 65° C. for 20 min and the digested plasmid was gel-purified using the Macherey & Nagel (M&N) Gel and PCR Clean-up kit (M&N #740609.250) following the manufacturer's instructions. The annealed oligonucleotides were diluted 1:10 and 1:100. 1 μl of diluted oligonucleotides were ligated into 200 ng of the linearised pLVTHM vector using 1 μl/400 u T4 ligase (NEB M0202S), 13.5 μl distilled water and 2 μl 10× ligase buffer (NEB B0202S). The ligation reaction was incubated at room temperature for 30 minutes and the ligase was heat-inactivated at 65° C. for 10 minutes. 1-5 μl of the ligation mixture was immediately transformed into One Shot STBL3 chemically competent E. coli (Invitrogen #C737303) following the manufacturer's instructions. Transformed STBL3 E. coli were transferred into LB-Agar plates containing 50 μg/ml Ampicillin and incubated overnight at 37° C. Bacterial colonies were transferred into LB-medium containing 50 μg/ml Ampicillin and incubated overnight at 37° C. in a rotating shaker. The high copy plasmids from the bacterial overnight cultures were purified in a mini-scale (NucleoSpin® Plasmid, M&N #740588.250), medium-scale (NucleoBond® PC 100, M&N #740573) or large-scale (NucleoBond® PC 2000, M&N #740576) format following the manufacturer's instructions. The purified plasmids were named pLVHTM.shRNActrl1, pLVTHM.shRNActrl2, pLVTHM.shRNA1, pLVTHM.shRNA2 or pLVTHM.shRNA3, respectively (common name as a group: pLVTHM.shRNA). The transfer plasmids were analysed for shRNA oligonucleotide insertion by restriction digest analysis and by sequencing using sequencing primers 100 and 101 upstream and downstream of the MluI/ClaI insertion site. Sequencing was performed using the Mix2Seq® sequencing services of Eurofins Genomics.

Design of Synthetic Alpha-1-Antitrypsin (sAAT)

There were several prerequisites for the recombinant synthetic alpha-1-antitrypsin. First, the recombinant synthetic alpha-1-antitrypsin should easily be cloned into a well-known lentiviral expression vector. Second, the newly designed sAAT should also be resistant to all shRNA/siRNA directed against naturally occurring alpha-1-antitrypsin (M-AAT and all MZ, ZZ isoforms) tested in this application. Third, it was required that the lentiviral expression vector had a high expressional activity in human hepatocytes in order to ensure sufficient rescue expression of the recombinant sAAT and to maintain therapeutical levels of alpha-1-antitrypsin in the blood stream.

In order to meet these prerequisites, a total of 39 nucleotides of the wild-type M-AAT (NM_000295.4) were manually identified as candidates for silent point mutations, thereby protecting the wild-type amino acid sequence and protein folding as seen in M-AAT. While 38 point mutations were introduced to render sAAT resistant to shRNA/siRNA knock-down, one single silent point mutation (G75A) was introduced to delete one BamHI restriction site within the open reading frame of M-AAT (Table 1). The deletion of the in-frame BamHI restriction site made it possible to flank the recombinant sAAT with BamHI restriction sites and to digest the recombinant sAAT gene with BamHI without interrupting the ORF. This way it was possible to easily introduce the full-length sAAT into the lentiviral expression vector pSFFV.IRES.dTom that uses BamHI restriction sites for insertion of recombinant genes. pSFFV.sAAT.IRES.dTom was a gift from Axel Schambach (Medizinische Hochschule Hannover, Germany).

Cloning of sAAT

Figure 3:
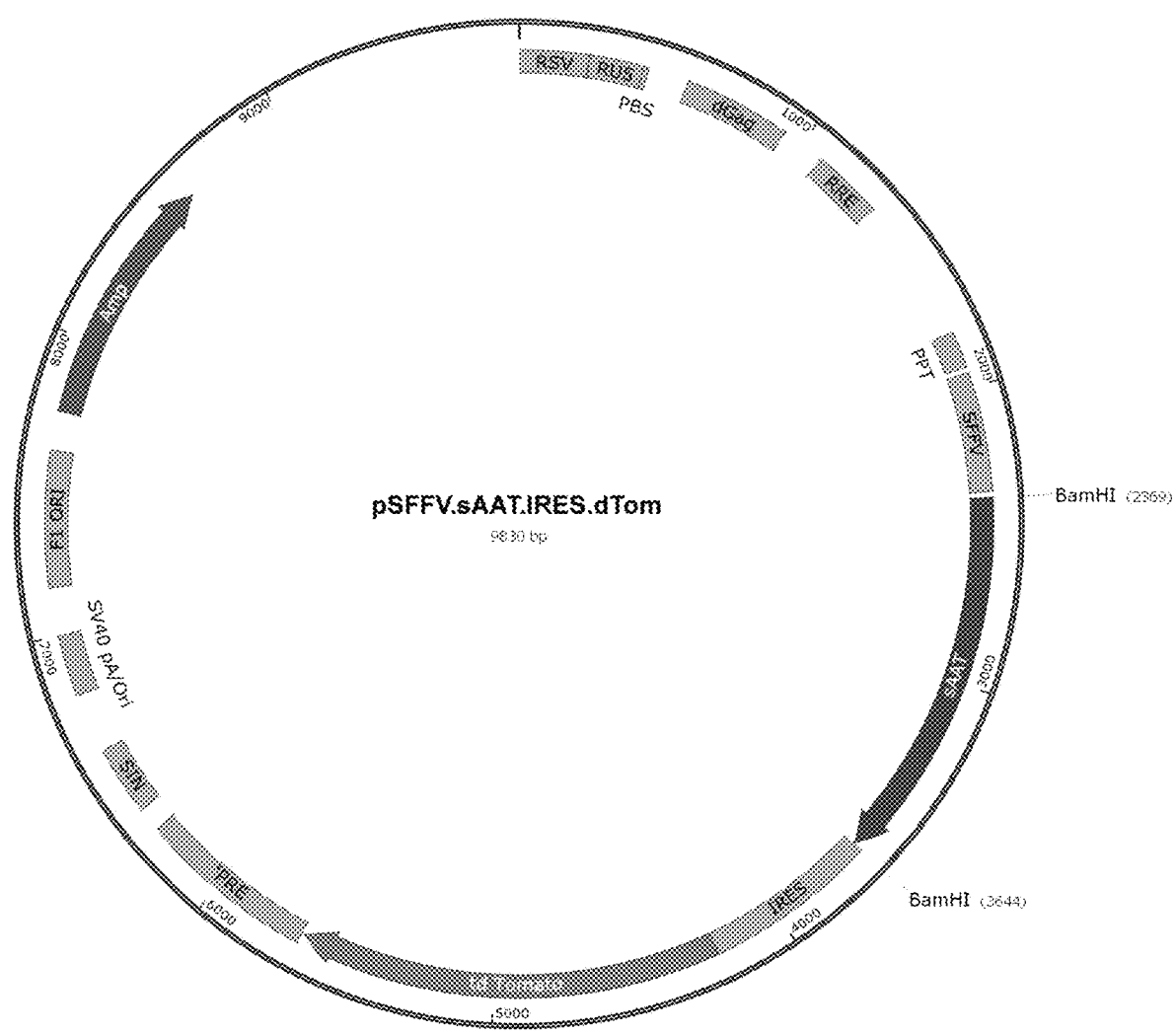
FIG. 3: pSFFV.sAAT.IRES.dTom: sAAT was cloned into the lentiviral transfer vector pSFFV.IRES.dTom using the BamHI restriction site to yield pSFFV.sAAT.IRES.dTom. Expression of sAAT is controlled by the strong eukaryotic promoter spleen focus forming virus (SFFV) promoter. The IRES element downstream of sAAT allows co-expression of the red fluorescence protein dTomato to easily identify transduced cells. Lentiviral production using the lentiviral transfer vector pSFFV.sAAT.IRES.dTom along with structural lentiviral plasmids yielded LV-sAAT.

Synthesis and cloning of sAAT into pSFFV.IRES.dTom was performed by GeneArt® gene synthesis and cloning services from ThermoFisher Scientific. The product was named pSFFV.sAAT.IRES.dTom (FIG. 3).

Design of Transfer Vector Containing Multiple shRNAs

Expression of shRNA is dependent on the promotional activity regulating the RNA Polymerases. In pLVTHM.shRNA, expression of the single shRNA is dependent of the H1 promoter (5398-5612) located upstream of the MluI/ClaI cloning site (5611-5681) for shRNA-oligonucleotides. One approach to maximize sRNA knockdown of native alpha-1-antitrypsin was to multiply the numbers of shRNA elements in the pLVTHM.shRNA vector. This could be achieved by insertion of additional shRNAs, each individually regulated by the promotional activity of specific RNA polymerase promoters such as the RNA polymerase III 7SK promoter and RNA polymerase II U1 promoter. An EcoRI restriction site (5392) was located upstream of the H1 promoter allowing insertion of such additional elements into pLVTHM.sRNA.

The design of the insert (SEQ ID NO: 37) containing additional RNA polymerase promoters and shRNAs included a 5' GCGC overhang, an EcoRI site (GAATTC) followed by a BsiWI site (CGTACG), the 7SK promoter sequence CTGCAGTATTTAGCATGCCCCACCCATCTGC AAGGCATTCTGGATAGTGTCAAAACAGCCGGAAATCAAGTCCGTTTATCTCAAAC TTTAGCATTTTGGGAATAAATGATATTTGCTATGCTGGTTAAATTAGATTTTAGTT AAATTTCCTGCTGAAGCTCTAGTACGATAAGTAACTTGACCTAAGTGTAAAGTTG AGATTTCCTTCAGGTTTATATAGCTTGTGCGCCGCCTGGGTACCTC, the shRNA sense-loop-antisense sequence CGCGTCCCCGGTCTGCCAGCTTACATTTAC ACTCGAGA GTAAATGTAAGCTGGCAGACC (for shRNA 1; sense and anti-sense in italique, hairpin loop underlined), a GGTCTTCACCTGAGG spacer, the 7SK terminations sequence TTTTT, a GCGCGCGC spacer, the U1 promoter sequence CTAAGGACCAGCTTCTTTGGGAGAGAACAGACGCAGGGGCGGGAGGGAAAAAG GGAGAGGCAGACGTCACTTCCCCTTGGCGGCTCTGGCAGCAGATTGGTCGGTTGA GTGGCAGAAAGGCAGACGGGGACTGGGCAAGGCACTGTCGGTGACATC ACGGAC AGGGCGACTTCTATGTAGATGAGGCAGCGCAGAGGCTGCTGCTTCGCCACTTGCT GCTTCACCACGAAGGAGTTCCCGTGCCCTGGGAGCGGGTTCAGGACCGCTGATCG GAAGTGAGAATCCCAGCTGTGTGTCAGGGCTGGAAAGGGCTCGGGAGTGCGCGG GGCAAGTGACCGTGTGTGTAAAGAGTGAGGCGTATGAGGCTGTGTCGGGGCAGA GGCCCAAGATCTC, a second shRNA sense-loop-antisense sequence CGCGTCCCC GGTCTGCCAGCTTACATTTAC ACTCGAGAGTAAATGTAAGCTGGCAGACC (for shRNA 1; sense and anti-sense in italique, hairpin loop underlined), a GCAGTCTGGAG spacer, the U1 termination sequence TTTCAAAAGTA GACTG, an 3' EcoRI site and a 3' GCGC overhang.

Synthesis of the newly designed insert and cloning into pLVTHM.shRNA was performed by GeneArt® gene synthesis and cloning services from ThermoFisher Scientific. The newly generated plasmids were purified as described earlier. Insertion was validated by sequencing and restriction analysis. The plasmids were named pLVTHM.shRNAYx3 (Y representing the character of the shRNA=shRNA1 shRNA2 or shRNA3) and allowed expression of triple shRNA controlled by three individual RNA polymerase promoters.

Design of Transfer Vector Containing Combined Expression of a Rescue Synthetic Alpha-1-Anitrypsin 2 (sAAT2) and Multiple shRNAs One major goal was to acquire simultaneous expression of multiple shRNA and recombinant synthetic alpha-1-antitrypsin resistant to shRNA from transduction with one lentiviral specimen. To achieve this, expressional elements needed for the rescue expression of a synthetic alpha-1-antitrypsin 2 (sAAT2) were integrated into one cloning oligonucleotide insert along with additional RNA polymerase promoters and shRNAs. The expressional elements were spleen focus forming virus (SFFV) promoter, a spacer and the ORF of sAAT2 and were flanked by a BsiWI restriction site. The SFFV promoter is characterized by high expressional activity in hepatocytes. sAAT2 (SEQ ID NO:3) was modified compared to sAAT by removing the silent point mutations causing resistance against shRNA ctrl 1 and shRNA ctrl2. The sequence of the entire insert containing sAAT2 expressional elements and multiple shRNAs1 can be viewed in sequences as SEQ ID NO: 38.

The insert was synthesized as a whole and cloned into pLVTHM.shRNA by GeneArt® gene synthesis and cloning services from ThermoFisher Scientific. The newly generated plasmids were purified as described earlier. Insertion was validated by sequencing and restriction analysis.

Lentivirus Production Using the Calcium Chloride Transfection Method

The procedures for lentiviral production were based on the calcium chloride transfection method described earlier (Dull et al., 1998). The following stock solutions were prepared in advance:

HBS (2×): 50 mM HEPES, 280 mM NaCl (16.36 g/L), 1.5 mM $Na_2HPO_4$ (0.21 g/L), adjust pH to 7.12 with 5 M NaOH.

Calcium Chloride (2.5 M): 27.75 g anhydrous $CaCl_2$ (Sigma #C5670) are dissolved in 100 ml $dH_2O$, sterile-filtered through a 0.22 μm filter and aliquoted into 1 ml aliquots.

Chloroquine (25 mM): 0.129 g chloroquine diphosphate salt (Sigma #C6628) were dissolved in 10 ml distilled water, sterile-filtered through a 0.22 μm filter and aliquoted into 500 μl aliquots.

Protamine sulfate (8 mg/ml): 80 mg protamine sulfate (Sigma #P4020) were dissolved in 10 ml distilled water, sterile-filtered through a 0.22 μm filter and aliquoted into 500 μl aliquots.

10-14 days before lentiviral production HEK293T were propagated frequently every 2-3 days in T175 $cm^2$ flasks. 24 hours before transfection, cells were harvested and 4.5*$10^6$ HEK293T cells were seeded into 10 cm Petri dishes containing DMEM+supplements. Two hours before transfection, cell confluency was determined and should have reached approximately 70%-80%. The cell medium was exchanged to DMEM containing Penicillin/Streptomycin, 1 mM L-glutamine, 1 mM sodium pyruvate 10% FCS, 10 mM chloroquine (Sigma #6628) and 10 mM HEPES (Gibco #15630-080).

Preparation of the transfection plasmids were started one hour before transfection. For a large-scale batch of lentiviral production of one specific lentivirus, ten Petri dishes were treated with transfection plasmids. The following numbers are stated as the required amounts for each Petri dish. For a medium-scale lentiviral production using ten Petri dishes the numbers have to be multiplied by ten. The plasmids pMD2.G, and psPax2 and were a gift from Didier Trono (Addgene plasmid #12259, and 12260, respectively).

10 µg of lentiviral transfer plasmid, 12 µg of psPax2 plasmid (containing the Gag-pol-rev genes) and 1.5 µg of the vesicular stomatitis virus (VSV) envelope expression plasmid pMD2.G plasmid were mixed in a 50 ml conical tube. The plasmids were diluted with sterile distilled water to a volume of 450 µl and 50 µl 2.5 M $CaCl_2$ were added. The mixture was transferred into 500 µl room temperature HBS (making it a total volume of 1000 µl), incubated at room temperature for 20 minutes. One ml of the mixture was added dropwise moving in circles above the Petri dish to cover the entire dish area. The transfected cells were incubated for 12 hours at 37° C. at 5% $CO_2$. The medium was exchanged 12 and 24 hours after transfection with DMEM containing supplements without chloroquine. The cell culture supernatant containing the lentiviral particles was collected 36 hours after transfection and sterile filtered through 0.22 µm Millex-GP filters (Millipore #SLGP033RS). The sterile filtered supernatant, approximately 70 ml in total volume, was transferred into the Centricon® Plus-70 Centrifugal Filter Units.

Concentration of the Lentivirus by Ultrafiltration

A 15-20-fold concentration of the lentivirus supernatant was achieved by ultrafiltration with the Centricon® Plus-70 Centrifugal Filter Units (Millipore #UFC710008). A total of 70 ml sterile filtered supernatant was transferred into the Centricon® Plus-70 Centrifugal Filter Unit container and placed into a refrigerated centrifuge. The supernatant was filtered by centrifugation at 3500 g at 4° C. for approximately 17-20 minutes until the retained supernatant reached a volume of about 3-4 ml. The container was placed into the collection cup and centrifuged at 1500 g, 4° C. for 2 min. The concentrated lentivirus was aliquoted into 1.5 ml centrifugation tubes and stored at −80° C.

Determination of Lentivirus Titers Using FACS

Titration of the lentivirus was performed using flow cytometry associated sorting (FACS)-based calculations of multiplicity of infection (MOI) and infective particles per volume. The concentrated lentiviral was diluted 1:10 with RPMI 1640+supplements. $1*10^5$ HepG2 cells were seeded into each well of a 24-well dish and maintained in RPMI 1640+supplements containing 4 g/ml protamine sulphate. For transduction, rising volumes (i.e. 1 µl, 2 µl, 5 µl, 10 µl, 20 µl and 40 µl) of the diluted lentivirus were added to the HepG2 cells and incubated at 37° C. 5% $CO_2$ for 24 hours. Medium was exchanged every two to three days. The HepG2 cells were harvested on day five for flow cytometry analysis. Cells were washed with PBS (GE, #) once and treated with 100 µl 0.05% trypsin acid (EDTA, GE, #) for 5 minutes at 37° C. Cells were detached by soft shaking of the wells and resuspended with 400 µl RPMI+supplements. The cells were centrifuged at 300 rcf for 5 min and resuspended with 300 µl FACS buffer (PBS+1% BSA+2 mM EDTA). The percentage of fluorescent cells was detected by flow cytometry and used to calculate the viral.

Lentivirus Infection of Target Cells

Concentrated lentivirus was thawed shortly before transduction of cells. HepG2 cells were seeded at a density of $0.45*10^5$ or $1*10^6$ cells into the wells of 12-well dishes or 6-well dishes, respectively, prior to transduction and maintained in RPMI 1640+supplements+protamine sulfate. Target HepG2 cells were transduced with a calculated amount of infective lentiviral particles equaling the desired MOI. Transduction was performed for 24 hours at 37 C, 5% $CO_2$. Medium was exchanged 24 hours after transduction and cells were maintained with RPMI supplemented with 10% FCS and Penicillin/Streptomycin. Medium was exchanged every two to three days. Cells were prepared for Western Blot, FACS or quantitative real-time PCR at least three days after transduction.

FACS and Sub-Cultivation

HepG2 cells were prepared and pelleted as mentioned in the protocol for determination of lentiviral titers by FACS. The cells were resuspended in PBS (+5 mM EDTA) and filtered through a cell strainer with 40 µm pores (Falcon 352340). The cells were sorted for eGFP fluorescent cells and sub-cultured in 6 well plates for analysis with FACS, qPCR and Western Blot once recovered.

mRNA Isolation

Total RNA from transduced and non-transduced cells was isolated using the RNA isolation kit from Macherey & Nagel (reference number 740955.250). All steps were performed on ice. In detail, cell medium was discarded, 250 µl Lysis Buffer RA1 supplemented with 1% (v/v) β-mercaptoethanol was added to the cells and incubated for 1 minute. The entire cell layer was repeatedly aspirated with a 3 ml syringe to disrupt the cell membrane and release RNA. The cell suspension was transferred into the NucleoSpin® filter units accompanying the RNA isolation kit. RNA isolation was performed using the manufacturer's instructions. RNA was eluted with 60 µl RNAse-free water. DNAse digestion of the RNA samples was repeated with the QIAGEN DNAse digestion kit to ensure minimal background DNA signals during qPCR.

Additional Digestion of RNA with DNAse and RNA Precipitation

Isolated mRNA was once again digested with QIAGEN RNAse-free DNAse set (50) (Qiagen #79254) following the manufacturer's instructions to ensure efficient removal of residual genomic DNA. In detail, 30 µl of isolated mRNA was treated with 10 µl Rx buffer RDD, 2.5 µl DNAse and 57.5 µl water and incubated for 30 min at room temperature. RNA was precipitated using the sodium acetate ethanol precipitation assay. For this, 10 µl (1/10 volume) of 3 M sodium acetate was added to the mRNA mixture treated with DNAse along with 2.5 times volume 100% Ethanol. The mixture was incubated at −20 for at least two hours and centrifuged at 4° C. for 60 min at 11000 g. The RNA pellet was washed with 200 µl 70% ethanol and air-dried for 15 min. The RNA pellet was resuspended with 50 µl RNAse-free water. The RNA concentration was determined using the Nanodrop 2000.

Reverse Transcription

Reverse transcription was performed with High Capacity cDNA Reverse Transcription Kit (ThermoFisher Scientific #4368814) following the manufacturer's instructions. In short, 500 ng RNA were mixed with 2 µl reverse transcriptase (RT) buffer, 0.8 µl dNTPs, 2 µl random primer, 1 µl RT (50 u) and distilled water was added up to a total volume of 20 µl. The reverse transcription reaction was performed at 25° C. for 10 min, at 37° C. for 120 min, at 85° C. for 5 min and kept on hold at 4° C. until further treatment.

qPCR cDNA samples were diluted 1:10 with distilled water. qPCR reactions were performed using iQ™ SYBR® Green Supermix (BioRad #170-8886) following the manufacturer's instructions. In short, 5 µl diluted cDNA was mixed with 0.5 µl forward qPCR primer, 0.5 µl reverse qPCR primer, 10 µl of SYBR Green mix and 4 µl distilled water per sample. qPCR cycles were one denaturation cycle at 95° C. for 2 min, then 39 cycles of 5 seconds denaturation at 95° C. and elongation at 60° C. for 30 seconds. At the end, a melting curve was determined. Gene expression analysis was performed using the ΔΔCT method (Livak and Schmittgen, 2001).

Western Blot

Medium supernatant of transduced and non-transduced HepG2 cells was collected in 1.5 ml 1.5 ml centrifugation tubes and protein was precipitated by trichloroacetic (Sigma #T6399) acid protein protocol.

The cell medium supernatant was treated with 100% trichloroacetic acid to a final volume of 20% trichloroacetic acid. The mixture was centrifuged at 4° C. for 30 minutes and the precipitate was resuspended in 300 µl treated with 10 mls T-PER Tissue Protein Extraction Reagent (Thermo #78510) containing one tablet Complete protease inhibitor (Sigma #000000011697498001) and one tablet Phosstop (Sigma #000000004906845001).

The protein concentration of the resuspended precipitate and the cell lysate was determined by Pierce 660 nm Protein Assay Reagent (Thermo #22860) following the manufacturer's instructions.

Each sample was treated with 2×SDS PAGE buffer and heated to 95° C. for 5 min Equal amounts of protein (for lysate and cell medium supernatant, respectively) were loaded on SDS-PAGE 10% and electrophoresed at 120 V for 1.5-2 hours. The proteins were transferred by wet blotting onto a nitrocellulose membrane at 100 mA for one hour. The membranes were washed three times with PBS-T (PBS containing 0.2% (v/v) Tween-20) and incubated with 5% skim milk (w/v in PBS-T). The membranes were washed three times with PBS-T, incubated with primary antibodies goat-anti-AAT (Bethyl #A80-122A, dilution 1:200) or rabbit anti-actin (Abcam ab8227, dilution 1:1000) overnight. The membranes were washed three times with PBS-T and incubated with secondary antibodies rabbit-anti-goat (Daco #P0160, dilution 1:2000) and donkey-anti-rabbit (GE #NA934V, dilution 1:2000), respectively, for one hour. The membranes were washed three times with PBS-T and prepared for chemolumiscence using Immobilon Western Chemiluminescent HRP Substrate (Millipore #WKBLS0500). HRP activity was measured by chemiluminescent detection.

Results

Lentiviral transfer plasmids pSFFV.dTom.sAAT, pLVTHM.shRNA1/2/3, pLVTHM.shRNA1x3 and pLVTHM.shRNA1x3.sAAT2 were generated by molecular cloning. Insertion of the shRNA oligonucleotides and transgenic synthetic alpha-1-antitrysin was confirmed by restriction analysis and sequencing. Lentivirus were produced by HEK293T cells using the calcium transfection method. Lentivirus titers for the SFFV-driven lentivirus ranged from $1.05*10^6$ to $6.75*10^6$ infectious particles/ml. Titers for the pLVTHM-based lentiviruses ranged from $1.5*10^6$ to $3.44\ 10^7$ infectious particles/ml. Lentiviral titers for LVTHM-based lentiviruses containing multicistronic expression of shRNAs and sAAT2 were determined to $2.09*10^6$ infectious particles/ml for LV-shRNA1x3 and $7.16*10^5$ infectious particles/ml for LV-shRNA 1x3.sAAT2.

For overexpression and RNAi knock-down experiments, HepG2 cells were transduced with a specified multiplicity of infection. RNA from transduced cells was isolated and gene expression was determined by the means of qPCR.

Knock-Down of Native AAT by Single shRNA Expression

Figure 7:
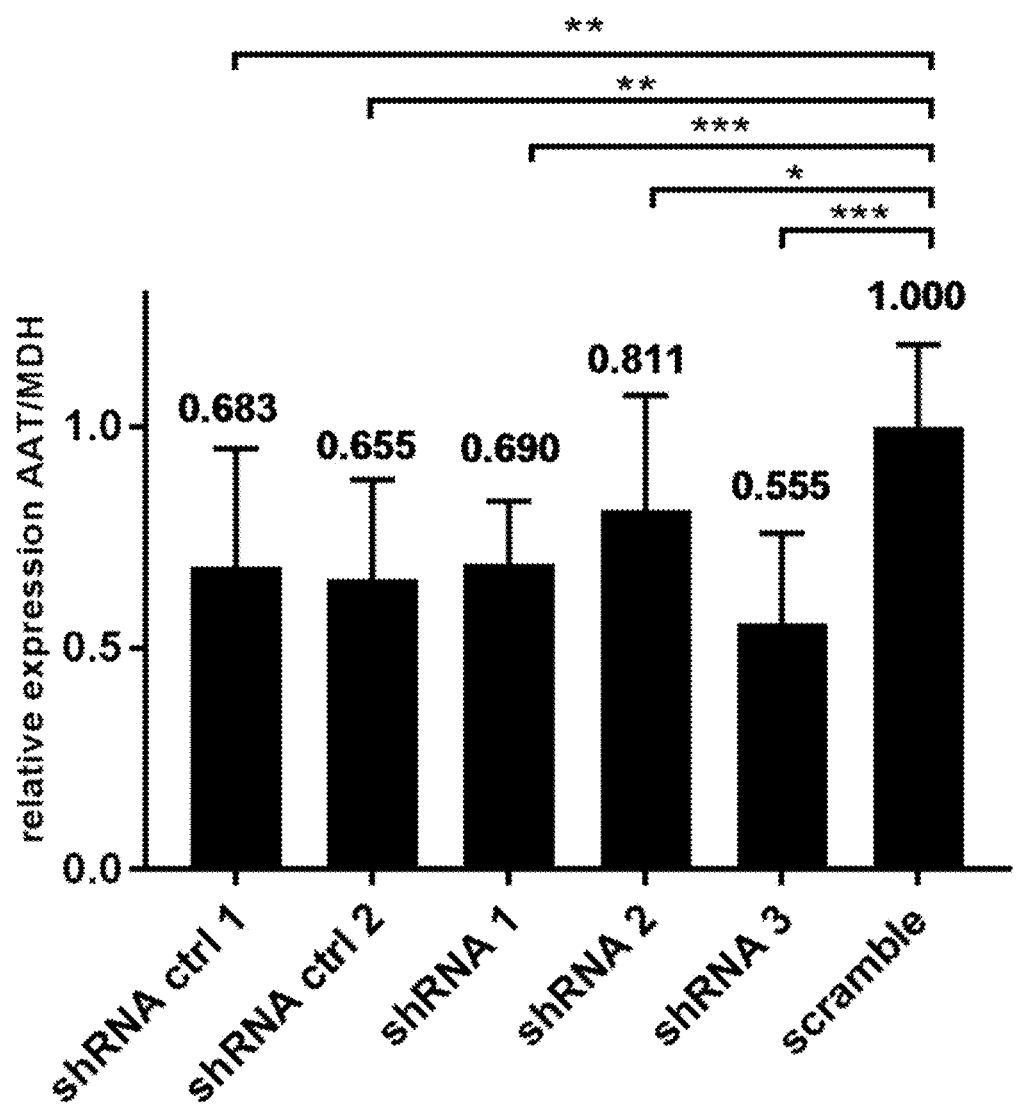
FIG. 7. Knock-down of native AAT. HepG2 cells were transduced with LV-shRNA ctrl 1/2, LV-shrNA1/2/3 or LV-scramble at on multiplicity of infection of 1. Expression of native AAT was determined by qPCR. Positive control shRNAs 1 and 2 was able to significantly knock-down expression of native AAT ($p_{shRNActrl1}$=0.014 and $p_{shRNActrl2}$=0.025). In addition, newly developed shRNA1 and shRNA3 demonstrated an effective and significant knock-down of the AAT target gene in HepG2 cells ($p_{shRNA1}$=0.001 and $p_{shRNA3}$=0.004). shRNA 2 (prior art) did not show a significant knock-down of native AAT compared to scrambled shRNA ($p_{shRNA2}$=0.099). The results are based on eight independent experiments. * p>0.05;  p<0.05; * p<0.005

HepG2 cells were transduced with LV-shRNA1/2/3, LV-shRNA ctrl 1/2 and LV-scramble with a MOI of 1. Expression of native AAT (M-AAT, Z-AAT and other native AAT isoforms) was determined after six days by the means of qPCR (FIG. 7). The results demonstrate that shRNA1 and shRNA 3 efficiently knock-down native AAT by the means of lentivirus mediated RNA interference. In these experiments shRNA 1 demonstrates a knock-down efficiency of 31% ($p_{shRNA1}$=0.001) compared to scrambled shRNA. ShRNA 3 exhibits a knock-down efficiency of 44.5% ($p_{shRNA3}$=0.004). The knock-down efficiency of the novel shRNAs 1 and 3 is similar to positive control shRNAs 1 and 2 and is statistically significant. On the contrary, shRNA 2 (prior art) (18.9%±26.%) was not able to knock-down native AAT in a statistically significant manner compared to scrambled shRNA in this specific experimental setting. Control shRNA ctrl 1 and shRNA ctrl 2 show knock-down efficiencies of 31.7% (±26.8%) and 34.5% (±22.5%), respectively ($p_{shRNA\ ctrl1}$<0.05; $p_{shRNA\ ctrl2}$<0.05).

Figure 8:
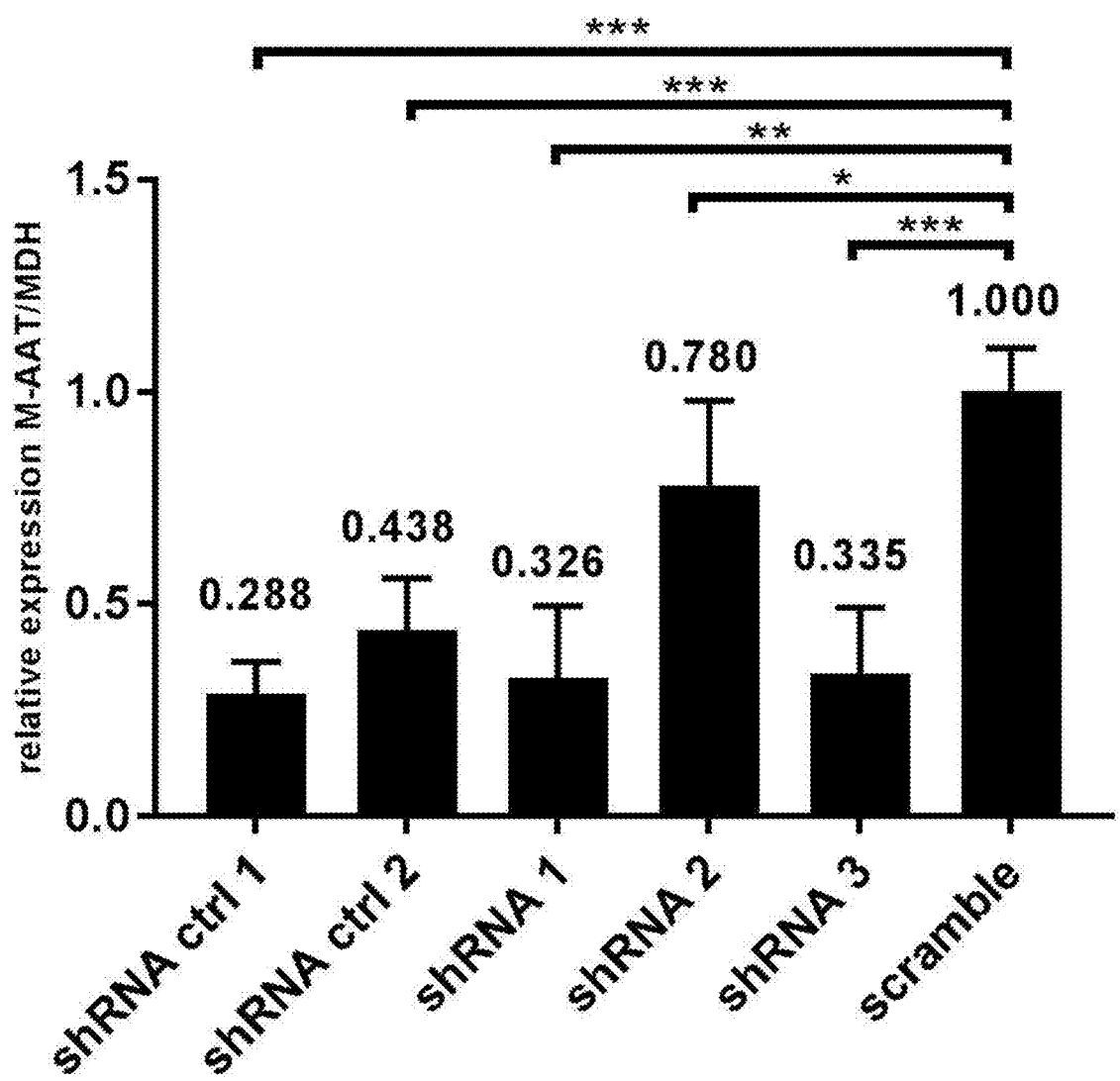
FIG. 8: Knock-down of native AAT in sorted HepG2 cells. HepG2 cells were transduced with LV-shRNA ctrl 1/2, LV-shrNA1/2/3 or LV-scramble at on multiplicity of infection of 0.5. The transduced cells were sorted by FACS to acquire pure cell cultures. Cell cultures were propagated for three weeks and RNA was isolated. Expression of native AAT was determined by qPCR. Positive control shRNAs 1 and 2 was able to significantly knock-down expression of native AAT ($p_{shRNActrl1}$=0.0015 and $p_{shRNActrl2}$=0.0018). In addition, newly developed shRNA1 and shRNA3 demonstrated an effective and significant knock-down of the AAT target gene in HepG2 cells ($p_{shRNA1}$=0.0155 and $p_{shRNA3}$=0.0042). shRNA 2 (prior art) did not show a significant knock-down of native AAT compared to scrambled shRNA ($p_{shRNA3}$=0.1014). The results are based on three independent experiments. * p>0.05;  p<0.05; * p<0.005

In a second attempt, HepG2 cells were treated with LV-shRNA1/2/3, LV-shRNA ctrl 1/2 and LV-scramble with a MOI of 0.5. Transduced eGFP positive cells underwent FACS processing to acquire pure cell cultures. Sorted cell cultures were cultured for three weeks until determination of MAAT expression by the means of qPCR (FIG. 8). The results show that shRNA 1 and shRNA 3 have knock-down efficiencies equivalent to control shRNAs that are significant compared to scramble shRNA. In pure cell cultures, shRNA 1 and shRNA 3 demonstrate a knock-down efficiency of 77.4% (±16.9%) and 76.5% (±15.7%), respectively ($p_{shRNA1}$=0.0155 and $p_{shRNA3}$=0.0042). Results from pure cell cultures confirm that the knock-down efficiency of 22% (±19.9%) of shRNA 2 (prior art) is non-significant in this experimental setting ($p_{shRNA2}$=0.1014). Control shRNA ctrl 1 and shRNA ctrl 2 show significant knock-down efficiencies of 81.2% (±7.6%) and 56.2% (±12.2%), respectively ($p_{shRNA\ ctrl1}$<0.005; $p_{shRNA\ ctrl2}$<0.005).

Overexpression of Synthetic AAT

Figure 9:
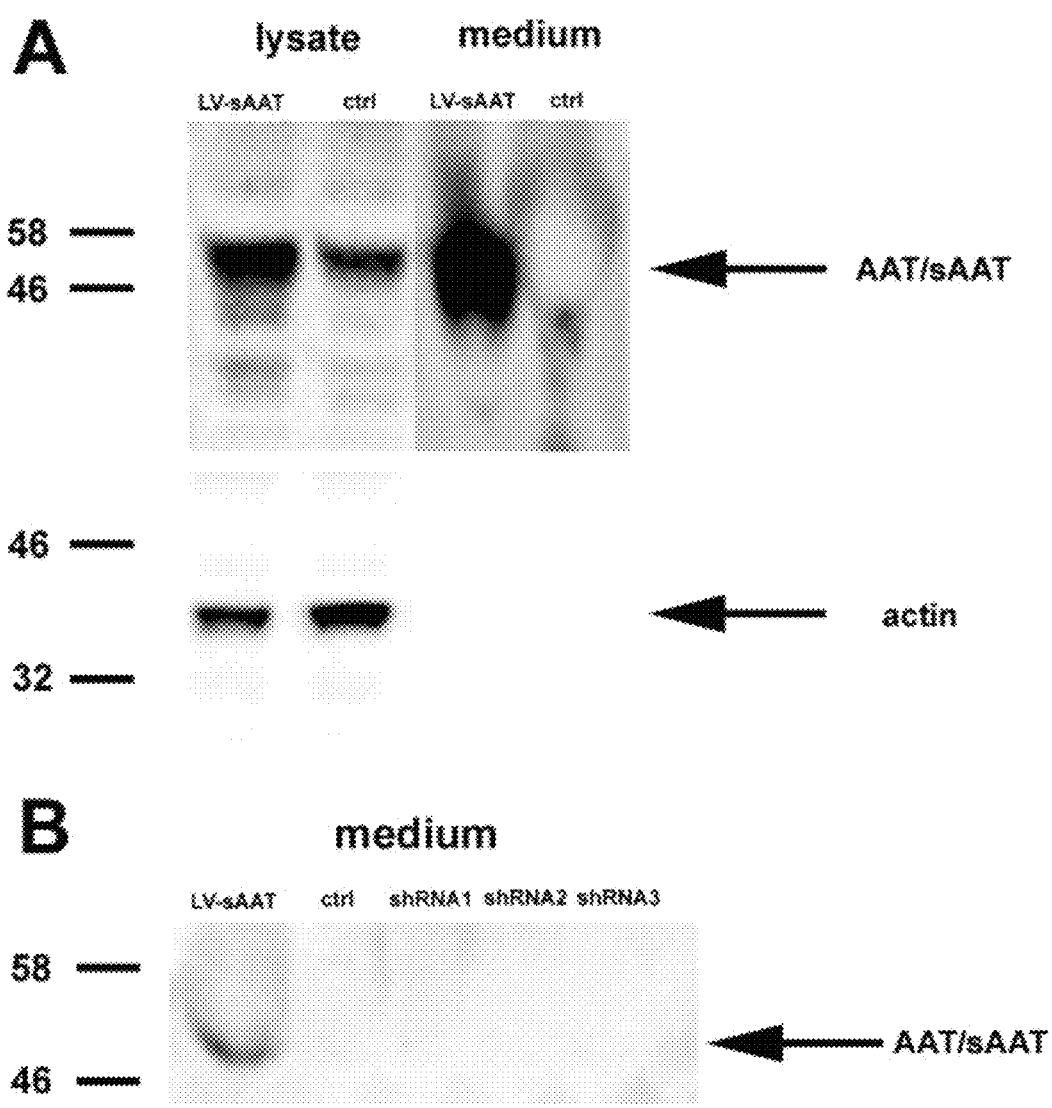
FIG. 9. Overexpression and secretion of synthetic AAT (sAAT). A HepG2 cells were transduced with LV-sAAT (LV-sAAT) or left untreated (ctrl). Five days after transduction the supernatant cell medium containing the secreted AAT/sAAT was collected and prepared for Western Blot analysis along with the cell lysates. In cell lysates, expression of AAT/sAAT is slightly elevated in treated cells compared to control cells. Levels of secreted AAT/sAAT is highly elevated in the cell medium of treated cells compared to untreated cells indicating a highly efficient production and secretion of synthetic sAAT from treated HepG2 cells. B HepG2 cells were transduced with LV-sAAT, LV-shRNA1/2/3 or left untreated. Five days after transduction the supernatant cell medium containing the secreted AAT/sAAT was collected and prepared for Western Blot analysis. AAT/sAAT is expressed in cells treated with LV-sAAT but cannot be detected in control cells or in cells treated with LV-shRNA1/2/3. Indicating that high level expression of AAT/sAAT is specific to cells treated with LV-sAAT. The picture is representative for three independent experiments.

HepG2 cells were transduced with LV-sAAT or LV-shRNA1x3.sAAT2 with a MOI of 1. Expression of AAT/sAAT in the cell lysate and of secreted AAT/sAAT accumulated in the cell culture medium was determined by the means of Western blot. Proteins in the supernatant cell medium was precipitated by trichloroacetic acid precipitation and protein concentrations were determined using Pierce protein assay. In cell lysates, expression of AAT/sAAT is slightly elevated in treated cells compared to control cells. Levels of secreted AAT/sAAT is highly elevated in the cell medium of treated cells compared to untreated cells indicating a highly efficient production and secretion of synthetic sAAT from treated HepG2 cells (FIG. 9A). HepG2 cells treated with LV-sAAT also demonstrate specific high level expression compared to HepG2 cells treated with knock-down LV-shRNA1/2/3 (FIG. 9B).

In addition, expression of synthetic AAT (sAAT or sAAT2) was determined by the means of qPCR. For this reason, primers specifically detecting the synthetic variants used in this application were designed based on the distinct point mutations integrated in sAAT and sAAT2. HepG2 cells were transduced with LV-sAAT or LV-shRNA1x3.sAAT2 and RNA was isolated after six days. qPCR was performed to detect expression of sAAT and sAAT2 and expression levels were expressed as absolute quantities (copy number of sAAT/sAAT2).

The results demonstrate that synthetic AAT (sAAT/sAAT2) are strongly expressed compared to non-treated control samples. HepG2 cells transduced with LV-sAAT contain 3191 (+/−689.6) copies of sAAT in the analysed sample while HepG2 cells transduced with LV-shRNA1.sAAT2 contain 2687 (+/−500) copies of sAAT2 (FIG. 10).

Knock-Down of Native AAT by Expression of Multiple shRNAs

Figure 11:
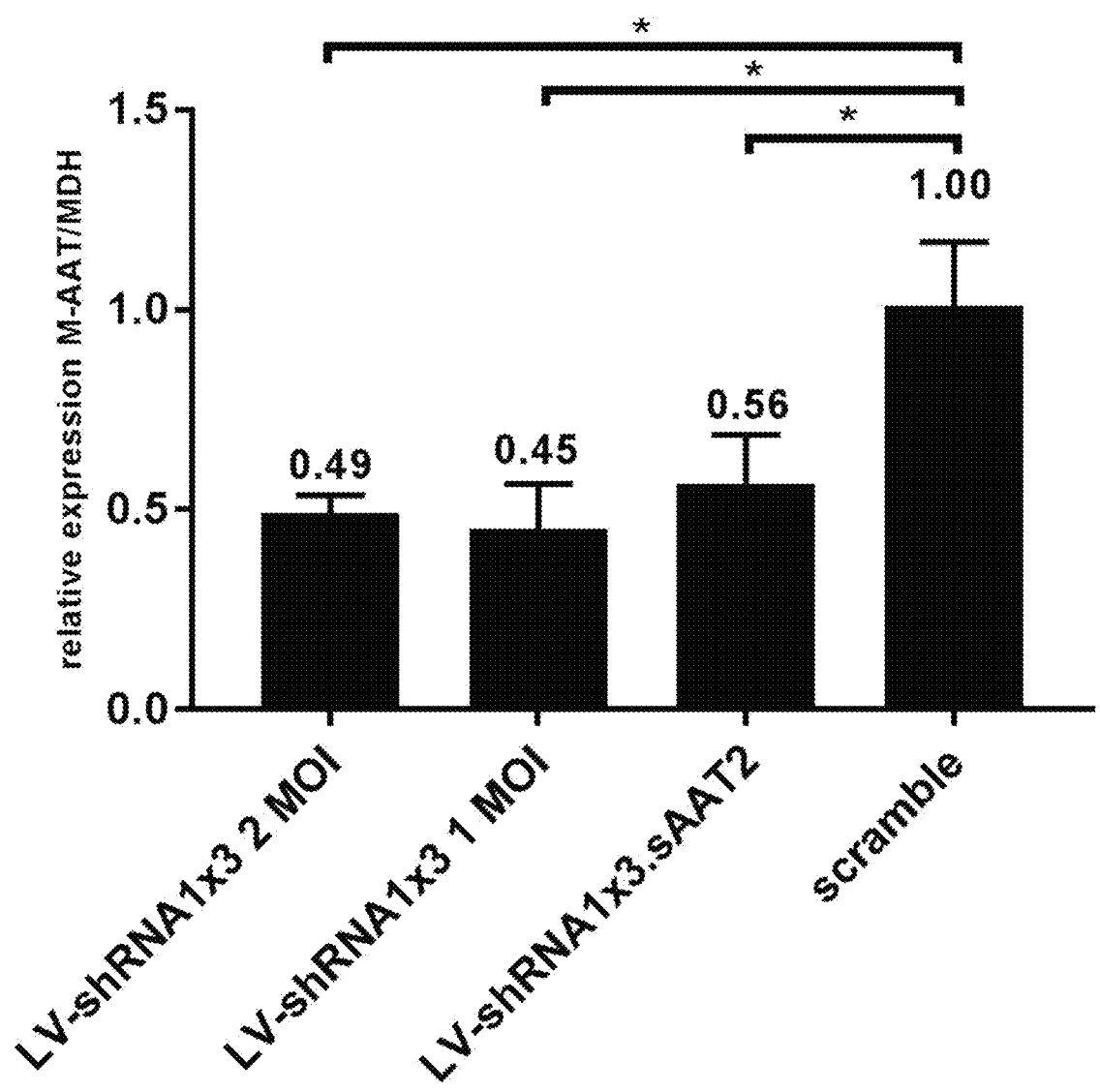
FIG. 11: Knock-down of M-AAT by multicistronic expression of shRNA 1. HepG2 cells were transduced with LV-shRNA1x3 (MOI 1 or 2) and LV-shRNA1x3.sAAT2 (MOI 1). RNA was isolated six days after transduction and expression of M-AAT was analysed by qPCR using M-AAT specific primers 1 and 2 (SEQ 29 and SEQ 30). All samples demonstrate significant knock-down of M-AAT ranging from 55% to 44% ($p_{shRNA1x3\ 1MOI}$=0.0262; $p_{shRNA1x3\ 2MOI}$=0.0056; $p_{shRNA1x3.sAAT2}$=0.0446). Despite the presence of 2687 copies of sAAT2 in the sample LV-shRNA1x3.sAAT2, no significant increase of AAT levels were detected, indicating the specificity of the M-AAT primers. The results are based on three independent experiments. * p<0.05

Knock-down of native AAT by multicistronic shRNA expression was achieved by transduction of HepG2 cells with LV-shRNA1x3 or LV-shRNA1x3.sAAT2. RNA was isolated six days after transduction and AAT expression was analysed by M-AAT specific primers. The results demonstrate that native AAT is knocked-down significantly by LV-shRNA1x3 and LV-shRNA1x3.sAAT2 ($p_{LV\text{-}shRNA1x3\ 1\ MOI}$=0.0057; $p_{LV\text{-}shRNA1x3\ 2\ MOI}$=0.0263; $p_{LV\text{-}shRNA1x3.sAAT2}$=0.0446). Native AAT is knock-downed by 55% (±11%) in cells treated with LV-shRNA1 at a MOI of 1, by 51% (±5%) at a MOI of 2 and 44% (±12%) in cells treated with LV-shRNA1x3.sAAT2 (FIG. 11).

Figure 10:
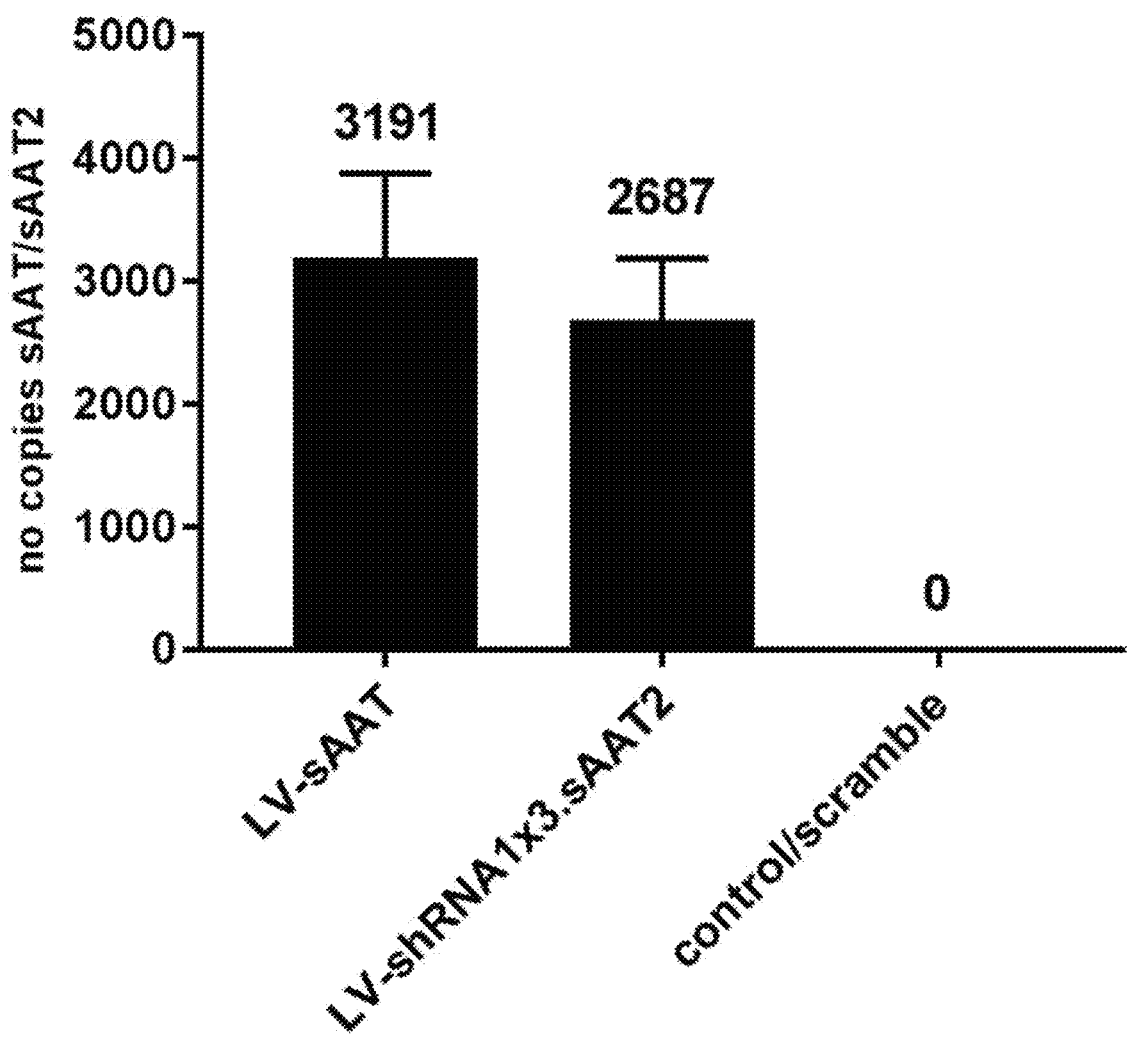
FIG. 10: Expression of synthetic AAT in transduced cells. HepG2 cells were treated with LV-sAAT, LV-shRNA1x3-sAAT or LV-scramble. RNA was isolated after six days and samples were prepared for qPCR using primers 3 and 4 (SEQ 31 and SEQ 32). A standard curve for sAAT and sAAT2 was determined. Synthetic AAT was specifically detected in cells transduced with LV-sAAT or LV-shRNA1x3-sAAT2. A total of 3191 and 2687 copies of sAAT and sAAT2 were determined in the analysed samples, respectively, while no copies of sAAT/sAAT2 were detected in control samples. The results are based on three independent experiments.

The primers specifically amplify native AAT as expression levels of M-AAT remain within range in HepG2 cells transduced with LV-shRNA1x3.sAAT2 despite strong expression of sAAT2 (FIG. 10). If the primers had amplified sAAT2, readings would have been elevated by 100-fold or more.

REFERENCES

Barnett V T, Sekosan M, Khurshid A. Wegener's granulomatosis and alpha1-antitrypsin-deficiency emphysema: proteinase-related diseases. Chest. 1999 July; 116(1):253-5.

Brummelkamp T R, Bernards R, Agami R. A system for stable expression of short interfering RNAs in mammalian cells. Science. 2002 Apr. 19; 296(5567):550-3

Cox D W. Alpha-1-Antitrypsin: a guardian of vascular tissue. Mayo Clinic Proc. 1994; 69:1123-4

Cox D W, Smyth S. Risk for liver disease in adults with alpha 1-antitrypsin deficiency. Am J Med. 1983 February; 74(2):221-7.

Dull T, Zufferey R, Kelly M, Mandel R J, Nguyen M, Trono D, Naldini L. A third-generation lentivirus vector with a conditional packaging system. J Virol. 1998 November; 72(11):8463-71.

Fearnley I R, Spalton D J, Ward A M, Slavin B, Muncey F. Alpha 1-antitrypsin phenotypes in acute anterior uveitis. Br J Ophthalmol. 1988 August; 72(8):636-9.

Mazodier P, Elzouki A N, Segelmark M, Eriksson S. Systemic necrotizing vasculitides in severe alpha1-antitrypsin deficiency. QJM. 1996 August; 89(8):599-611.

McBean J, Sable A, Maude J, Robinson-Bostom L. Alpha1-antitrypsin deficiency panniculitis. Cutis. 2003 March; 71(3):205-9.

Baum, C., Kustikova, O., Modlich, U., Li, Z. & Fehse, B. Mutagenesis and oncogenesis by chromosomal insertion of gene transfer vectors. Hum. Gene Ther. 17, 253-263 (2006).

Bessis, N., GarciaCozar, F. J. & Boissier, M. C. Immune responses to gene therapy vectors: influence on vector function and effector mechanisms. Gene Ther. 11 (Suppl. 1), S10-S17 (2004).

Burrows J A, Willis L K, Perlmutter D H. Chemical Chaperones mediate increased secretion of mutant alpha-1-antitrypsin (alpha-1-AT) Z: A potential pharmacological strategy for prevention of liver injury and emphysema in alpha 1-AT deficiency. Proc Natl Acad Sci USA. 2000; 97:1796-1801

Carrell R W, Lomas D A, Sidhar S, Foreman R. A1-Antitrypsin Deficiency. Chest 1996, 110; 6,243S-247S.

Cruz P E, Mueller C, Cossette T L, Golant A, Tang Q, Beattie S G, Brantly M, Campbell-Thompson M, Blomenkamp K S, Teckman J H, Flotte T R. In vivo post-transcriptional gene silencing of alpha-1 antitrypsin by adeno-associated virus vectors expressing siRNA. Lab Invest. 2007 September; 87(9):893-902.

Eriksson S. Studies in alpha 1-antitrypsin deficiency. Acta Med Scand Suppl. 1965; 432:1-85.

Hidvegi T, Ewing M, Hale P, Dippold C, Beckett C, Kemp C, Maurice N, Mukherjee A, Goldbach C, Watkins S, Michalopoulos G, Perlmutter D H. An autophagy-enhancing drug promotes degradation of mutant alpha1-antitrypsin Z and reduces hepatic fibrosis. Science. 2010; 329(5988):229-32.

Hidvegi T, Schmidt B Z, Hale P, Perlmutter D H. Accumulation of mutant alpha1-antitrypsin Z in the endoplasmic reticulum activates caspases-4 and -12, NFkappaB, and BAP31 but not the unfolded protein response. J Biol Chem. 2005 Nov. 25; 280(47):39002-15.

Hubbard R C, Crystal R G. Strategies for aerosol therapy of alpha-1-antitrypsin deficiency by the aerosol route. Lung 1990; 168 Suppl:567-578.

Karnaukhova E, Ophir Y, Golding B. Recombinant human alpha-1 proteinase inhibitor: towards therapeutic use. Amino Acids. 2006; 30(4):317-32.

Kramps J A, Bakker W, Dijkman J H: A matched-pair study of the leukocyte elastase-like activity in normal persons and in emphysematous patients with and without alpha1-antitrypsin deficiency. Am Rev Respir Dis 1980, 121:253-261.

Lawless M W, Greene C M, Mulgrew A, Taggart C C, O'Neill S J, McElvaney N G. Activation of endoplasmic reticulum-specific stress responses associated with the conformational disease Z alpha 1-antitrypsin deficiency. J Immunol. 2004 May 1; 172(9):5722-6.

Li Cl, Xiao P, Gray S J, Weinberg M S, Samulski R J. Combination therapy utilizing shRNA knockdown and an optimized resistant transgene for rescue of diseases caused by misfolded proteins. Proc Natl Acad Sci USA. 2011 Aug. 23; 108(34):14258-63

Livak K J, Schmittgen T D. Analysis of relative gene expression data using real-time quantitative PCR and the 2(-Delta Delta C(T)) Method. Methods. 2001 December; 25(4):402-8.

Mahadeva R, Dafforn T R, Carrell R W, Lomas D A. 6-mer peptide selectively anneals to a pathogenic serpin conformation and blocks polymerization. Implications for the prevention of Z alpha(1)-antitrypsin-related cirrhosis. J Biol Chem. 2002 Mar. 1; 277(9):6771-4. Epub 2001 Dec. 28.

Pack D W, Hoffman A S, Pun S, Stayton P S. Design and development of polymers for gene delivery. Nat Rev Drug Discov. 2005 July; 4(7):581-93.

Parfrey H, Dafforn T R, Belorgey D, Lomas D A, Mahadeva R. Inhibiting polymerization: new therapeutic strategies for Z alpha1-antitrypsin-related emphysema. Am J Respir Cell Mol Biol. 2004 August; 31(2):133-9. Epub 2004 Mar. 11.

Petrache I, Hajjar J, Campos M. Safety and efficiency of alpha-1-antitryspin augmentation therapy in the treatmedn of patients with alpha-1-antitryspin deficiency. Biologics 2009; 3:193-204.

Putnam, D. Polymers for gene delivery across length scales. Nature Mater 2006. 5, 439-451.

Ramarmooth M, Narvekar A, Non Viral Vectors in Gene Therapy—An Overview. Journal of Clinical and Diagnostic Research. 2015 January, Vol-9(1): GE01-GE06

Riedel G, Rüdrich U, Fekete-Drimusz N, Manns M P, Vondran F W, Bock M. An extended ΔCT-method facilitating normalisation with multiple reference genes suited for quantitative RT-PCR analyses of human hepatocyte-like cells. PLoS One. 2014 Mar. 21; 9(3):

Sandhaus R A. Alpha-1-Antitrypsin deficiency. 6: new and emerging treatments for alpha1-antitrypsin deficiency. Thorax. 2004 October; 59(10): 904-909.

Serres F, Blacno I. Role of alpha-1 antitrypsin in human health and disease. Journal of Internal Medicine, 2014, 276; 311-335

Spencer L T, Humphries J E, Brantly M L. Antibody response to aerosolized transgenic human alpha1-antitrypsin. N Engl J Med. 2005; 352(19):2030-1.

Stove V, Smits K, Naessens E, Plum J, Verhasselt B. Multiple gene knock-down by a single lentiviral vector expressing an array of short hairpin RNAs. Electronic Journal of Biotechnology 2006, 9(5): 572-579

Sveger T, Eriksson S. The liver in adolescents with alpha-1-antitrypsin deficiency. Hepatology 1995, 22:514-517

Ter Brake O, Hooft K, Liu Y, Centlivre M, von Eige K, Berkhout B, Lentiviral Vector Design for Multiple shRNA Expression and Durable HIV-1 Inhibition, Mol Ther 16(3):557-564

Teckman J H, Perlmutter D H. Retention of mutant alpha (1)-antitrypsin Z in endoplasmic reticulum is associated with an autophagic response. Am J Physiol Gastrointest Liver Physiol. 2000 November; 279(5):G961-74.

Vannucci L, Lai M, Chiuppesi F, Ceccherini-Nelli L, Pistello M. Viral vectors: a look back and ahead on gene transfer technology. New Microbiol. 2013 January; 36(1):1-22.

Wiznerowicz M, Trono D Conditional suppression of cellular genes: lentivirus vector-mediated drug-inducible RNA interference. J Virol. 2003 August 77(16):8957-61

Yin H, Kanasty R, Eltouky A, Vegas A, Darkin J R, Anderson D. Non-Viral vectors for gene based therapy Nature Rev. Genet. 2014, 15, 541-555.

The invention claimed is:

1. A chemically modified ribonucleic acid consisting of 21 nucleotides and having a sequence according to SEQ ID NO: 43.

2. The ribonucleic acid according to claim 1, wherein the chemically modified ribonucleic acid is modified in the phosphodiester backbone; or in the sugar backbone.

3. A DNA molecule comprising at least one nucleotide sequence complementary to the at RNA molecule according to claim 1, wherein the nucleotide sequence is operably linked to a single RNA polymerase promoter sequence.

4. The DNA molecule according to claim 3, wherein the RNA polymerase promoter is selected from RNA polymerase promoters H1, 7SK, and U1.

5. A virus particle comprising a recombinant viral genome, wherein said genome comprises a DNA molecule comprising the sequence of a DNA molecule according to claim 3.

6. A DNA molecule comprising at least two nucleotide sequences, each complementary to the RNA molecule according to claim 1, wherein each nucleotide sequence is independently operably linked to an RNA polymerase promoter sequence and wherein the RNA polymerase promoter sequence is the same for each nucleotide sequence.

7. A DNA molecule comprising at least two nucleotide sequences, each complementary to the RNA molecule according to claim 1, wherein each nucleotide sequence is independently operably linked to an RNA polymerase promoter sequence and wherein the RNA polymerase promoter sequence is different for each nucleotide sequence.

8. A virus particle comprising a recombinant viral genome, wherein said genome comprises an RNA molecule comprising a nucleotide sequence complementary to a DNA molecule comprising at least one nucleotide sequence complementary to at least one RNA molecule consisting of 46-100 nucleotides, comprising two sequences spaced 4-10 nucleotides apart, wherein the two sequences consist of the sequence pair: SEQ ID NO: 43 and 44.

9. A vehicle is selected from the group consisting of plasmid DNA, lipid-based vectors, and polymeric vectors, and comprising the DNA molecule according to claim 3.

10. A method for treatment of alpha-1-antitrypsin deficiency, said method comprising administering a nucleic acid molecule selected from the group consisting of a ribonucleic acid molecule consisting of 21 nucleotides and having a sequence selected from SEQ ID NO: 43 and 44, and a nucleic acid molecule consisting of 46-100 nucleotides, comprising two sequences spaced 4-10 nucleotides apart, wherein the two sequences consist of the sequence pair: SEQ ID NO: 43 and 44, to a subject in need thereof.

11. The method of treatment according to claim 10, wherein the nucleic acid molecule is administered using a vehicle delivered to the subject by way of gene gun/ballistic DNA, electroporation, sonoporation, hydroporation, magnetofection, needle injection and/or other methods facilitating the incorporation of DNA or RNA into the cell leading to a modified transcription and expression of target genes, wherein the vehicle is for delivery of nucleic acid material to a human cell in vivo.

12. The method for treatment according to claim 10, wherein the subject's genome is heterozygous or homozygous for a G342K mutation in a gene encoding alpha-1-antitrypsin.

13. The method for treatment according to claim 10, wherein the alpha-1-antitrypsin deficiency manifests as liver cirrhosis, pulmonary emphysema, necrotising panniculitis, systemic vasculitis, (intracranial) aneurysms, fibromuscular dysplasia, bleeding disorders, anterior uveitis, systemic necrotizing vasculitis and Wegener granulomatosis.

* * * * *

SEQUENCE LISTING

<160> NUMBER OF SEQ ID NOS: 46

<210> SEQ ID NO 1
<211> LENGTH: 1257
<212> TYPE: DNA
<213> ORGANISM: Homo sapiens

<400> SEQUENCE: 1

```
atgccgtctt ctgtctcgtg gggcatcctc ctgctggcag gcctgtgctg cctggtccct      60
gtctccctgg ctgaggatcc ccagggagat gctgcccaga agacagatac atcccaccat     120
gatcaggatc acccaacctt caacaagatc accccccaacc tggctgagtt cgccttcagc     180
ctataccgcc agctggcaca ccagtccaac agcaccaata tcttcttctc cccagtgagc     240
atcgctacag cctttgcaat gctctccctg gggaccaagg ctgacactca cgatgaaatc     300
ctggagggcc tgaatttcaa cctcacgag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcgggaca ccgaagaggc caagaaacag     540
atcaacgatt acgtggagaa gggtactcaa gggaaaattg tggatttggt caaggagctt     600
gacagagaca cagttttgc tctggtgaat tacatcttct ttaaaggcaa atgggagaga     660
ccctttgaag tcaaggacac cgaggaagag gacttccacg tggaccaggt gaccaccgtg     720
aaggtgccta tgatgaagcg tttaggcatg tttaacatcc agcactgtaa gaagctgtcc     780
agctgggtgc tgctgatgaa atacctgggc aatgccaccg ccatcttctt cctgcctgat     840 gagggaaac tacagcacct ggaaaatgaa ctcacccacg atatcatcac caagttcctg     900
gaaaatgaag acagaaggtc tgccagctta catttaccca aactgtccat tactggaacc     960
tatgatctga gagcgtcct gggtcaactg ggcatcacta aggtcttcag caatggggct    1020
gacctctccg gggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct ttgtcttctt aatgattgaa    1200
caaaatacca agtctcccct cttcatggga aaagtggtga atcccaccca aaaataa      1257
```

<210> SEQ ID NO 2
<211> LENGTH: 1257
<212> TYPE: DNA
<213> ORGANISM: Homo sapiens

<400> SEQUENCE: 2

```
atgccgtctt ctgtctcgtg gggcatcctc ctgctggcag gcctgtgctg cctggtccct      60
gtctccctgg ctgaagatcc ccagggagat gctgcccaga agaccgacac tagtcatcac     120
gatcaggatc acccaacctt caacaagatc accccccaac tggctgagtt cgccttcagc     180
ctataccgcc agctggcaca ccagtccaac agcaccaata tcttcttctc cccagtgagc     240
atcgctacag cctttgcaat gctctccctg gggaccaagg ctgacactca cgatgaaatc     300
ctggagggcc tgaatttcaa cctcacggag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcggggaca ccgaagaggc caagaaacag     540
atcaacgatt acgtggagaa gggtactcaa gggaaaattg tggatttggt caaggagctt     600
gacagagaca cagttttttgc tctggtgaat tacatcttct ttaaaggcaa atgggagaga     660
ccctttgaag tcaaggacac cgaggaagag gacttccacg tggaccaggt gaccaccgtg     720
aaggtgccta tgatgaaaag acttggtatg tttaacatcc agcactgtaa gaagctgtcc     780
agctgggttt tattgatgaa gtacctgggc aatgccaccg ccatcttctt cctgcctgat     840
gaggggaaac tacagcacct ggaaaatgaa ctcacccacg atatcatcac caagttcctg     900
gaaaatgaag acagaaggag cgcatctctg cacctcccca aactgtccat tactggaacc     960
tatgatctga gagcgtcctg ggccagtta ggtattacaa aggtcttcag caatggggct    1020
gacctctccg ggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct tgtcttctt aatgattgaa    1200
caaaatacca agtctcccct cttcatggga aaagtggtga atcccaccca aaaataa     1257
```

<210> SEQ ID NO 3
<211> LENGTH: 1257
<212> TYPE: DNA
<213> ORGANISM: Homo sapiens

<400> SEQUENCE: 3

```
atgccgtctt ctgtctcgtg gggcatcctc ctgctggcag gcctgtgctg cctggtccct      60
gtctccctgg ctgaagatcc ccagggagat gctgcccaga agacagatac atcccaccat     120
gatcaggatc acccaacctt caacaagatc accccccaac tggctgagtt cgccttcagc     180
ctataccgcc agctggcaca ccagtccaac agcaccaata tcttcttctc cccagtgagc     240
atcgctacag cctttgcaat gctctccctg gggaccaagg ctgacactca cgatgaaatc     300
ctggagggcc tgaatttcaa cctcacggag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcggggaca ccgaagaggc caagaaacag     540
atcaacgatt acgtggagaa gggtactcaa gggaaaattg tggatttggt caaggagctt     600
gacagagaca cagttttttgc tctggtgaat tacatcttct ttaaaggcaa atgggagaga     660
```

```
cccttttgaag tcaaggacac cgaggaagag gacttccacg tggaccaggt gaccaccgtg      720
aaggtgccta tgatgaagcg tttaggcatg tttaacatcc agcactgtaa gaagctgtcc      780
agctgggttt tattgatgaa gtacctgggc aatgccaccg ccatcttctt cctgcctgat      840
gaggggaaac tacagcacct ggaaaatgaa ctcacccacg atatcatcac caagttcctg      900
gaaaatgaag acagaaggag cgcatctctg cacctcccca aactgtccat tactggaacc      960
tatgatctga gagcgtcct gggccagtta ggtattacaa aggtcttcag caatggggct      1020
gacctctccg gggtcacaga ggaggcaccc ctgaagctct ccaaggccgt gcataaggct      1080
gtgctgacca tcgacgagaa agggactgaa gctgctgggg ccatgttttt agaggccata      1140
cccatgtcta tcccccccga ggtcaagttc aacaaaccct ttgtcttctt aatgattgaa      1200
caaaatacca agtctcccct cttcatggga aagtggtga atcccaccca aaaataa        1257
```

<210> SEQ ID NO 4
<211> LENGTH: 1257
<212> TYPE: DNA
<213> ORGANISM: Homo sapiens

<400> SEQUENCE: 4

```
atgccgtctt ctgtctcgtg gggcatcctc ctgctggcag gcctgtgctg cctggtccct       60
gtctccctgg ctgaggatcc ccagggagat gctgcccaga agacagatac atcccaccat      120
gatcaggatc acccaaccTT caacaagatc accccccaacc tggctgagtt cgccttcagc      180
ctataccgcc agctggcaca ccagtccaac agcaccaata tcttcttctc cccagtgagc      240
atcgctacag cctttgcaat gctctccctg gggaccaagg ctgacactca cgatgaaatc      300
ctggagggcc tgaatttcaa cctcacggag attccgagg ctcagatcca tgaaggcttc      360
caggaactcc tccgtaccct caaccagcca gacagccagc tccagctgac caccggcaat      420
ggcctgttcc tcagcgaggg cctgaagcta gtggataaat ttttggagga tgttaaaaag      480
ttgtaccact cagaagcctt cactgtcaac ttcggggaca ccgaagaggc caagaaacag      540
atcaacgatt acgtggagaa gggtactcaa gggaaaattg tggatttggt caaggagctt      600
gacagagaca cagttttgc tctggtgaat tacatcttct ttaaaggcaa atgggagaga      660 cccttttgaag tcaaggacac cgaggaagag gacttccacg tggaccaggc gaccaccgtg      720
aaggtgccta tgatgaagcg tttaggcatg tttaacatcc agcactgtaa gaagctgtcc      780
agctgggtgc tgctgatgaa atacctgggc aatgccaccg ccatcttctt cctgcctgat      840
gaggggaaac tacagcacct ggaaaatgaa ctcacccacg atatcatcac caagttcctg      900
gaaaatgaag acagaaggtc tgccagctta catttaccca aactgtccat tactggaacc      960
tatgatctga gagcgtcct gggtcaactg ggcatcacta aggtcttcag caatggggct      1020
gacctctccg gggtcacaga ggaggcaccc ctgaagctct ccaaggccgt gcataaggct      1080
gtgctgacca tcgacaagaa agggactgaa gctgctgggg ccatgttttt agaggccata      1140
cccatgtcta tcccccccga ggtcaagttc aacaaaccct ttgtcttctt aatgattgaa      1200
caaaatacca agtctcccct cttcatggga aagtggtga atcccaccca aaaataa        1257
```

<210> SEQ ID NO 5
<211> LENGTH: 19
<212> TYPE: DNA
<213> ORGANISM: Artificial Sequence
<220> FEATURE:
<223> OTHER INFORMATION: positive control shRNA published in Cruz et al., 2007, sense

```
<400> SEQUENCE: 5
gacagataca tcccaccat                                                19

<210> SEQ ID NO 6
<211> LENGTH: 19
<212> TYPE: DNA
<213> ORGANISM: Artificial Sequence
<220> FEATURE:
<223> OTHER INFORMATION: positive control shRNA published in Cruz et
      al., 2007, antisense

<400> SEQUENCE: 6
ctggtgggat gtatctgtc                                                19

<210> SEQ ID NO 7
<211> LENGTH: 66
<212> TYPE: DNA
<213> ORGANISM: Artificial Sequence
<220> FEATURE:
<223> OTHER INFORMATION: positive control shRNA published in Cruz et
      al., 2007, cloning oligo

<400> SEQUENCE: 7
cgcgtccccg acagatacat cccaccatac tcgagaatgg tgggatgtat ctgtcttttt    60
ggaaat                                                              66

<210> SEQ ID NO 8
<211> LENGTH: 64
<212> TYPE: DNA
<213> ORGANISM: Artificial Sequence
<220> FEATURE:
<223> OTHER INFORMATION: positive control shRNA published in Cruz et
      al., 2007, cloning oligo 2

<400> SEQUENCE: 8
cgatttccaa aaagacagat acatcccacc attctcgagt atggtgggat gtatctgtcg    60
ggga                                                                64

<210> SEQ ID NO 9
<211> LENGTH: 19
<212> TYPE: DNA
<213> ORGANISM: Artificial Sequence
<220> FEATURE:
<223> OTHER INFORMATION: positive control shRNA published in Li et al.,
      2011, sense

<400> SEQUENCE: 9
gatgaagcgt ttaggcatg                                                19

<210> SEQ ID NO 10
<211> LENGTH: 19
<212> TYPE: DNA
<213> ORGANISM: Artificial Sequence
<220> FEATURE:
<223> OTHER INFORMATION: positive control shRNA published in Li et al.,
      2011, antisense

<400> SEQUENCE: 10
catgcctaaa cgcttcatc                                                19

<210> SEQ ID NO 11
<211> LENGTH: 66
<212> TYPE: DNA
<213> ORGANISM: Artificial Sequence
```

```
<220> FEATURE:
<223> OTHER INFORMATION: positive control shRNA published in Li et al.,
      2011, oligo 3

<400> SEQUENCE: 11
cgcgtccccg atgaagcgtt taggcatgac tcgagacatg cctaaacgct tcatcttttt    60
ggaaat                                                               66

<210> SEQ ID NO 12
<211> LENGTH: 64
<212> TYPE: DNA
<213> ORGANISM: Artificial Sequence
<220> FEATURE:
<223> OTHER INFORMATION: positive control shRNA published in Li et al.,
      2011, oligo 4

<400> SEQUENCE: 12
cgatttccaa aaagatgaag cgtttaggca tgtctcgagt catgcctaaa cgcttcatcg    60
ggga                                                                 64

<210> SEQ ID NO 13
<211> LENGTH: 21
<212> TYPE: DNA
<213> ORGANISM: Artificial Sequence
<220> FEATURE:
<223> OTHER INFORMATION: shRNA1, sense

<400> SEQUENCE: 13
ggtctgccag cttacattta c                                              21

<210> SEQ ID NO 14
<211> LENGTH: 21
<212> TYPE: DNA
<213> ORGANISM: Artificial Sequence
<220> FEATURE:
<223> OTHER INFORMATION: shRNA 1, antisense

<400> SEQUENCE: 14
gtaaatgtaa gctggcagac c                                              21

<210> SEQ ID NO 15
<211> LENGTH: 70
<212> TYPE: DNA
<213> ORGANISM: Artificial Sequence
<220> FEATURE:
<223> OTHER INFORMATION: shRNA1, oligo5

<400> SEQUENCE: 15
cgcgtccccg gtctgccagc ttacatttac actcgagagt aaatgtaagc tggcagacct    60
ttttggaaat                                                           70

<210> SEQ ID NO 16
<211> LENGTH: 68
<212> TYPE: DNA
<213> ORGANISM: Artificial Sequence
<220> FEATURE:
<223> OTHER INFORMATION: shRNA1, oligo 6

<400> SEQUENCE: 16
cgatttccaa aaaggtctgc cagcttacat ttacactcga gagtaaatgt aagctggcag    60
accgggga                                                             68

<210> SEQ ID NO 17
```

```
<211> LENGTH: 19
<212> TYPE: DNA
<213> ORGANISM: Artificial Sequence
<220> FEATURE:
<223> OTHER INFORMATION: shRNA2, sense

<400> SEQUENCE: 17
gggtgctgct gatgaaata                                                  19

<210> SEQ ID NO 18
<211> LENGTH: 19
<212> TYPE: DNA
<213> ORGANISM: Artificial Sequence
<220> FEATURE:
<223> OTHER INFORMATION: shRNA2, antisense

<400> SEQUENCE: 18
tatttcatca gcagcaccc                                                  19

<210> SEQ ID NO 19
<211> LENGTH: 66
<212> TYPE: DNA
<213> ORGANISM: Artificial Sequence
<220> FEATURE:
<223> OTHER INFORMATION: shRNA2, oligo 7

<400> SEQUENCE: 19
cgcgtccccg ggtgctgctg atgaaataac tcgagatatt tcatcagcag cacccttttt     60
ggaaat                                                                66

<210> SEQ ID NO 20
<211> LENGTH: 64
<212> TYPE: DNA
<213> ORGANISM: Artificial Sequence
<220> FEATURE:
<223> OTHER INFORMATION: shRNA2, oligo 9

<400> SEQUENCE: 20
cgatttccaa aaagggtgct gctgatgaaa taactcgaga tatttcatca gcagcacccg     60
ggga                                                                  64

<210> SEQ ID NO 21
<211> LENGTH: 21
<212> TYPE: DNA
<213> ORGANISM: Artificial Sequence
<220> FEATURE:
<223> OTHER INFORMATION: shRNA3, sense

<400> SEQUENCE: 21
gggtcaactg ggcatcacta a                                               21

<210> SEQ ID NO 22
<211> LENGTH: 21
<212> TYPE: DNA
<213> ORGANISM: Artificial Sequence
<220> FEATURE:
<223> OTHER INFORMATION: shRNA3, antisense

<400> SEQUENCE: 22
ttagtgatgc ccagttgacc c                                               21

<210> SEQ ID NO 23
<211> LENGTH: 70
<212> TYPE: DNA
<213> ORGANISM: Artificial Sequence
```

```
<220> FEATURE:
<223> OTHER INFORMATION: shRNA3, oligo 9

<400> SEQUENCE: 23
cgcgtccccg ggtcaactgg gcatcactaa actcgagatt agtgatgccc agttgaccct    60
ttttggaaat                                                          70

<210> SEQ ID NO 24
<211> LENGTH: 68
<212> TYPE: DNA
<213> ORGANISM: Artificial Sequence
<220> FEATURE:
<223> OTHER INFORMATION: shRNA3, oligo 10

<400> SEQUENCE: 24
cgatttccaa aagggtcaa ctgggcatca ctaaactcga gattagtgat gcccagttga     60
cccgggga                                                            68

<210> SEQ ID NO 25
<211> LENGTH: 21
<212> TYPE: DNA
<213> ORGANISM: Artificial Sequence
<220> FEATURE:
<223> OTHER INFORMATION: scramble shRNA, sense

<400> SEQUENCE: 25
gtgatcgcgt caacgactag a                                             21

<210> SEQ ID NO 26
<211> LENGTH: 21
<212> TYPE: DNA
<213> ORGANISM: Artificial Sequence
<220> FEATURE:
<223> OTHER INFORMATION: scramble shRNA, antisense

<400> SEQUENCE: 26
tctagtcgtt gacgcgatca c                                             21

<210> SEQ ID NO 27
<211> LENGTH: 70
<212> TYPE: DNA
<213> ORGANISM: Artificial Sequence
<220> FEATURE:
<223> OTHER INFORMATION: scramble shRNA, oligo 11

<400> SEQUENCE: 27
cgcgtccccg tgatcgcgtc aacgactaga actcgagatc tagtcgttga cgcgatcact    60
ttttggaaat                                                          70

<210> SEQ ID NO 28
<211> LENGTH: 68
<212> TYPE: DNA
<213> ORGANISM: Artificial Sequence
<220> FEATURE:
<223> OTHER INFORMATION: scramble shRNA, oligo 12

<400> SEQUENCE: 28
cgatttccaa aaagtgatcg cgtcaacgac tagaactcga gatctagtcg ttgacgcgat    60
cacgggga                                                            68

<210> SEQ ID NO 29
<211> LENGTH: 20
<212> TYPE: DNA
```

<210> SEQ ID NO 29
<211> LENGTH: 20
<212> TYPE: DNA
<213> ORGANISM: Artificial Sequence
<220> FEATURE:
<223> OTHER INFORMATION: Forward primer M-AAT

<400> SEQUENCE: 29
gggtgctgct gatgaaatac                                                 20

<210> SEQ ID NO 30
<211> LENGTH: 20
<212> TYPE: DNA
<213> ORGANISM: Artificial Sequence
<220> FEATURE:
<223> OTHER INFORMATION: Reverse primer M-AAT

<400> SEQUENCE: 30
ttagtgatgc ccagttgacc                                                 20

<210> SEQ ID NO 31
<211> LENGTH: 24
<212> TYPE: DNA
<213> ORGANISM: Artificial Sequence
<220> FEATURE:
<223> OTHER INFORMATION: Forward primer sAAT/sAAT2

<400> SEQUENCE: 31 gggtttatt gatgaagtac ctgg                                             24

<210> SEQ ID NO 32
<211> LENGTH: 22
<212> TYPE: DNA
<213> ORGANISM: Artificial Sequence
<220> FEATURE:
<223> OTHER INFORMATION: Reverse primer sAAT/sAAT2

<400> SEQUENCE: 32
tttgtaatac ctaactggcc ca                                              22

<210> SEQ ID NO 33
<211> LENGTH: 21
<212> TYPE: DNA
<213> ORGANISM: Artificial Sequence
<220> FEATURE:
<223> OTHER INFORMATION: Forward primer MDH

<400> SEQUENCE: 33
gtcacgactg tgcagcagcg t                                               21

<210> SEQ ID NO 34
<211> LENGTH: 25
<212> TYPE: DNA
<213> ORGANISM: Artificial Sequence
<220> FEATURE:
<223> OTHER INFORMATION: Reverse primer MDH

<400> SEQUENCE: 34
tggggttcca aaccagatgt ccctg                                           25

<210> SEQ ID NO 35
<211> LENGTH: 25
<212> TYPE: DNA
<213> ORGANISM: Artificial Sequence
<220> FEATURE:
<223> OTHER INFORMATION: Forward sequencing primer on pLVTHM to check
      shRNA insert

<400> SEQUENCE: 35

```
tgatagagaa aagtgaaagt cgggg                                          25

<210> SEQ ID NO 36
<211> LENGTH: 25
<212> TYPE: DNA
<213> ORGANISM: Artificial Sequence
<220> FEATURE:
<223> OTHER INFORMATION: reverse sequencing primer on pLVTHM to check
      shRNA insert

<400> SEQUENCE: 36
gacccagtac aagcaaaaag cagca                                          25

<210> SEQ ID NO 37
<211> LENGTH: 835
<212> TYPE: DNA
<213> ORGANISM: Artificial Sequence
<220> FEATURE:
<223> OTHER INFORMATION: Sequence of insert for shRNA 1 x 3

<400> SEQUENCE: 37
gcgcgaattc cgtacgctgc agtatttagc atgccccacc catctgcaag gcattctgga    60
tagtgtcaaa acagccggaa atcaagtccg tttatctcaa actttagcat tttgggaata   120
aatgatattt gctatgctgg ttaaattaga ttttagttaa atttcctgct gaagctctag   180
tacgataagt aacttgacct aagtgtaaag ttgagatttc cttcaggttt atatagcttg   240
tgcgccgcct gggtacctcc gcgtcccggg tctgccagct tacatttaca ctcgagagta   300
aatgtaagct ggcagaccgg tcttcacctg aggtttttgc gcgcgcctaa ggaccagctt   360 cttttgggaga gaacagacgc aggggcggga gggaaaaagg gagaggcaga cgtcacttcc   420
ccttggcggc tctggcagca gattggtcgg ttgagtggca gaaaggcaga cggggactgg   480
gcaaggcact gtcggtgaca tcacggacag ggcgacttct atgtagatga ggcagcgcag   540
aggctgctgc ttcgccactt gctgcttcac cacgaaggag ttcccgtgcc ctgggagcgg   600
gttcaggacc gctgatcgga agtgagaatc ccagctgtgt gtcagggctg aaagggctc    660 gggagtgcgc ggggcaagtg accgtgtgtg taaagagtga ggcgtatgag gctgtgtcgg   720
ggcagaggcc caagatctcc gcgtcccggg tctgccagct tacatttaca ctcgagagta   780
aatgtaagct ggcagaccgc agtctggagt ttcaaaagta gactggaatt cgcgc        835

<210> SEQ ID NO 38
<211> LENGTH: 2518
<212> TYPE: DNA
<213> ORGANISM: Artificial Sequence
<220> FEATURE:
<223> OTHER INFORMATION: Sequence of insert for shRNA 1 x 3 containing
      sAAT2

<400> SEQUENCE: 38
gcgcgaattc cgtacgagct agctgcagta acgccatttt gcaaggcatg gaaaaatacc    60
aaaccaagaa tagagaagtt cagatcaagg gcgggtacat gaaaatagct aacgttgggc   120
caaacaggat atctgcggtg agcagtttcg gccccggccc ggggccaaga acagatggtc   180
accgcagttt cggccccggc ccgaggccaa gaacagatgg tccccagata tggcccaacc   240
ctcagcagtt tcttaagacc catcagatgt ttccaggctc ccccaaggac ctgaaatgac   300
cctgcgcctt atttgaatta accaatcagc ctgcttctcg cttctgttcg cgcgcttctg   360
cttcccgagc tctataaaag agctcacaac ccctcactcg gcgcgccagt cctccgacag   420
actgagtcgg ccggtgatgc cgtcttctgt ctcgtggggc atcctcctgc tggcaggcct   480
```

```
gtgctgcctg gtccctgtct ccctggctga agatccccag ggagatgctg cccagaagac      540
agatacatcc caccatgatc aggatcaccc aaccttcaac aagatcaccc ccaacctggc      600
tgagttcgcc ttcagcctat accgccagct ggcacaccag tccaacagca ccaatatctt      660
cttctcccca gtgagcatcg ctacagcctt tgcaatgctc tccctgggga ccaaggctga      720
cactcacgat gaaatcctgg agggcctgaa tttcaacctc acggagattc cggaggctca      780
gatccatgaa ggcttccagg aactcctccg taccctcaac cagccagaca ccagctcca      840 gctgaccacc ggcaatggcc tgttcctcag cgagggcctg aagctagtgg ataagttttt      900
ggaggatgtt aaaaagttgt accactcaga agccttcact gtcaacttcg ggacaccga      960 agaggccaag aaacagatca cgattacgt ggagaagggt actcaaggga aaattgtgga     1020
tttggtcaag gagcttgaca gagacacagt ttttgctctg gtgaattaca tcttctttaa     1080
aggcaaatgg gagagaccct ttgaagtcaa ggacaccgag aagaggact tccacgtgga     1140 ccaggtgacc accgtgaagg tgcctatgat gaagcgttta gcatgtttta acatccagca     1200
ctgtaagaag ctgtccagct gggttttatt gatgaagtac ctgggcaatg ccaccgccat     1260
cttcttcctg cctgatgagg ggaaactaca gcacctggaa aatgaactca cccacgatat     1320
catcaccaag ttcctggaaa atgaagacag aaggagcgca tctctgcacc tccccaaact     1380
gtccattact ggaacctatg atctgaagag cgtcctgggc cagttaggta ttacaaaggt     1440
cttcagcaat ggggctgacc tctccggggt cacagaggag gcaccctga agctctccaa     1500 ggccgtgcat aaggctgtgc tgaccatcga cgagaaaggg actgaagctg ctggggccat     1560
gtttttagag gccataccca tgtctatccc ccccgaggtc aagttcaaca aacccttgt     1620 cttcttaatg attgaacaaa ataccaagtc tccctcttc atgggaaaag tggtgaatcc     1680
cacccaaaaa taacgtacgc tgcagtattt agcatgcccc acccatctgc aaggcattct     1740
ggatagtgtc aaaacagccg gaaatcaagt ccgtttatct caaactttag cattttggga     1800
ataaatgata tttgctatgc tggttaaatt agattttagt taaatttcct gctgaagctc     1860
tagtacgata agtaacttga cctaagtgta aagttgagat ttccttcagg tttatatagc     1920
ttgtgcgccg cctgggtacc tccgcgtccc cggtctgcca gcttacattt acactcgaga     1980
gtaaatgtaa gctggcagac cggtcttcac ctgaggtttt tgcgcgcgcc taaggaccag     2040
cttctttggg agagaacaga cgcagggggcg ggagggaaaa agggagaggc agacgtcact     2100
tccccttggc ggctctggca gcagattggt cggttgagtg gcagaaaggc agacggggac     2160
tgggcaaggc actgtcggtg acatcacgga cagggcgact tctatgtaga tgaggcagcg     2220
cagaggctgc tgcttcgcca cttgctgctt caccacgaag gagttcccgt gccctgggag     2280
cgggttcagg accgctgatc ggaagtgaga atcccagctg tgtgtcaggg ctggaaaggg     2340
ctcgggagtg cgcggggcaa gtgaccgtgt gtgtaaagag tgaggcgtat gaggctgtgt     2400
cggggcagag gccaagatc tccgcgtccc cggtctgcca gcttacattt acactcgaga     2460
gtaaatgtaa gctggcagac cgcagtctgg agtttcaaaa gtagactgga attcgcgc     2518
```

<210> SEQ ID NO 39
<211> LENGTH: 21
<212> TYPE: RNA
<213> ORGANISM: Artificial Sequence
<220> FEATURE:
<223> OTHER INFORMATION: sense shRNA1

<400> SEQUENCE: 39

```
ggucugccag cuuacauuua c                                              21
```

<210> SEQ ID NO 40
<211> LENGTH: 21
<212> TYPE: RNA
<213> ORGANISM: Artificial Sequence
<220> FEATURE:
<223> OTHER INFORMATION: shRNA1, antisense

<400> SEQUENCE: 40

```
guaaauguaa gcuggcagac c                                              21
```

<210> SEQ ID NO 41
<211> LENGTH: 19
<212> TYPE: RNA
<213> ORGANISM: Artificial Sequence
<220> FEATURE:
<223> OTHER INFORMATION: shRNA2, sense RNA

<400> SEQUENCE: 41

```
gggugcugcu gaugaaaua                                                 19
```

<210> SEQ ID NO 42
<211> LENGTH: 19
<212> TYPE: RNA
<213> ORGANISM: Artificial Sequence
<220> FEATURE:
<223> OTHER INFORMATION: shRNA2, antisense RNA

<400> SEQUENCE: 42

```
uauuucauca gcagcaccc                                                 19
```

<210> SEQ ID NO 43
<211> LENGTH: 21
<212> TYPE: RNA
<213> ORGANISM: Artificial Sequence
<220> FEATURE:
<223> OTHER INFORMATION: shRNA3, sense RNA

<400> SEQUENCE: 43

```
gggucaacug gcaucacua a                                               21
```

<210> SEQ ID NO 44
<211> LENGTH: 21
<212> TYPE: RNA
<213> ORGANISM: Artificial Sequence
<220> FEATURE:
<223> OTHER INFORMATION: shRNA3, antisense RNA

<400> SEQUENCE: 44

```
uuagugaugc ccaguugacc c                                              21
```

<210> SEQ ID NO 45
<211> LENGTH: 418
<212> TYPE: PRT
<213> ORGANISM: Homo sapiens
<220> FEATURE:
<221> NAME/KEY: SIGNAL
<222> LOCATION: (1)..(24)
<300> PUBLICATION INFORMATION:
<308> DATABASE ACCESSION NUMBER: NP_000286
<309> DATABASE ENTRY DATE: 2004-07-19
<313> RELEVANT RESIDUES IN SEQ ID NO: (1)..(418)

<400> SEQUENCE: 45

```
Met Pro Ser Ser Val Ser Trp Gly Ile Leu Leu Leu Ala Gly Leu Cys
1               5                   10                  15
```

-continued

```
Cys Leu Val Pro Val Ser Leu Ala Glu Asp Pro Gln Gly Asp Ala Ala
             20                  25                  30
Gln Lys Thr Asp Thr Ser His His Asp Gln Asp His Pro Thr Phe Asn
         35                  40                  45
Lys Ile Thr Pro Asn Leu Ala Glu Phe Ala Phe Ser Leu Tyr Arg Gln
 50                  55                  60
Leu Ala His Gln Ser Asn Ser Thr Asn Ile Phe Phe Ser Pro Val Ser
 65                  70                  75                  80
Ile Ala Thr Ala Phe Ala Met Leu Ser Leu Gly Thr Lys Ala Asp Thr
                 85                  90                  95
His Asp Glu Ile Leu Glu Gly Leu Asn Phe Asn Leu Thr Glu Ile Pro
            100                 105                 110
Glu Ala Gln Ile His Glu Gly Phe Gln Glu Leu Leu Arg Thr Leu Asn
            115                 120                 125
Gln Pro Asp Ser Gln Leu Gln Leu Thr Thr Gly Asn Gly Leu Phe Leu
130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
            275                 280                 285
Asn Glu Leu Thr His Asp Ile Ile Thr Lys Phe Leu Glu Asn Glu Asp
290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415

Gln Lys
```

```
<210> SEQ ID NO 46
<211> LENGTH: 480
<212> TYPE: DNA
<213> ORGANISM: Artificial Sequence
<220> FEATURE:
<223> OTHER INFORMATION: Nucleotides 5281 - 5760 of pLVTHM.shRNA1

<400> SEQUENCE: 46
agagaaaagt gaaagtcgag tttaccactc cctatcagtg atagagaaaa gtgaaagtcg      60
agtttaccac tccctatcag tgatagagaa aagtgaaagt cggggctgca ggaattcgaa     120
cgctgacgtc atcaacccgc tccaaggaat cgcgggccca gtgtcactag gcgggaacac     180
ccagcgcgcg tgcgccctgg caggaagatg gctgtgaggg acaggggagt ggcgccctgc     240
aatatttgca tgtcgctatg tgttctggga aatcaccata aacgtgaaat gtctttggat     300
ttgggaatct tataagttct gtatgagacc acgcgtcccc ggtctgccag cttacattta     360
cactcgagag taaatgtaag ctggcagacc tttttggaaa tcgataccgt cgcatgggaa     420
taacttcgta tagcatacat tatacgaagt tatgctgctt tttgcttgta ctgggtctct     480
```